(12) United States Patent
Grace et al.

(10) Patent No.: US 10,898,213 B2
(45) Date of Patent: Jan. 26, 2021

(54) ELECTRICALLY-INDUCED PRESSURE WAVE EMITTING CATHETER SHEATH

(71) Applicant: The Spectranetics Corporation, Colorado Springs, CO (US)

(72) Inventors: Kenneth P. Grace, Woodland Park, CO (US); Thomas Triffo, Colorado Springs, CO (US); James Cezo, Colorado Springs, CO (US)

(73) Assignee: THE SPECTRANETICS CORPORATION, Colorado Springs, CO (US)

( * ) Notice: Subject to any disclaimer, the term of this patent is extended or adjusted under 35 U.S.C. 154(b) by 238 days.

(21) Appl. No.: 14/984,710

(22) Filed: Dec. 30, 2015

(65) Prior Publication Data

US 2016/0262784 A1    Sep. 15, 2016

Related U.S. Application Data

(60) Provisional application No. 62/098,242, filed on Dec. 30, 2014, provisional application No. 62/209,691, (Continued)

(51) Int. Cl.
*A61B 17/22*    (2006.01)
*A61B 18/26*    (2006.01)
*A61B 18/24*    (2006.01)

(52) U.S. Cl.
CPC .. *A61B 17/22004* (2013.01); *A61B 17/22022* (2013.01); *A61B 18/245* (2013.01); *A61B 18/26* (2013.01); *A61B 2017/22025* (2013.01); *A61B 2017/22038* (2013.01); *A61B 2017/22049* (2013.01); *A61B 2018/263* (2013.01)

(58) Field of Classification Search
CPC ...... A61B 17/00234; A61B 17/320068; A61B 18/26; A61B 18/245; A61B 2017/00292; A61B 17/3201; A61B 2017/00778; A61B 2017/32032; A61B 2018/263; A61B 17/3203

See application file for complete search history.

(56) References Cited

U.S. PATENT DOCUMENTS 4,770,653 A    9/1988  Shturman
4,785,806 A    11/1988 Deckelbaum
(Continued)

FOREIGN PATENT DOCUMENTS

CN    103462688 A    12/2013
DE    2517019 A    10/1976
(Continued)

OTHER PUBLICATIONS

International Preliminary Report on Patentability issued in PCT/US2014/019268, dated Sep. 24, 2015, 9 pages.
(Continued)

*Primary Examiner* — Kathleen S Holwerda
*Assistant Examiner* — Brooke Labranche

(57) ABSTRACT

The present disclosure relates generally to the use of medical devices for the treatment of vascular conditions. In particular, the present disclosure provides devices and methods for using electrically-induced pressure waves created within a sheath to disrupt vascular blockages via the sheath and/or a tip at the end of the sheath.

16 Claims, 42 Drawing Sheets

Related U.S. Application Data filed on Aug. 25, 2015, provisional application No. 62/212,242, filed on Aug. 31, 2015, provisional application No. 62/248,753, filed on Oct. 30, 2015, provisional application No. 62/248,936, filed on Oct. 30, 2015, provisional application No. 62/264,725, filed on Dec. 8, 2015, provisional application No. 62/268,797, filed on Dec. 17, 2015.

(56) References Cited

U.S. PATENT DOCUMENTS

| | | |
|---|---|---|
| 4,793,359 A | 12/1988 | Sharrow |
| 4,832,023 A | 5/1989 | Murphy-Chutorian et al. |
| 4,862,886 A | 9/1989 | Clarke et al. |
| 4,878,492 A | 11/1989 | Sinofsky et al. |
| 4,966,596 A | 10/1990 | Kuntz et al. |
| 4,993,412 A | 2/1991 | Murphy-Chutorian |
| 5,010,886 A | 4/1991 | Passafaro et al. |
| 5,026,366 A | 6/1991 | Leckrone |
| 5,026,367 A | 6/1991 | Leckrone et al. |
| 5,029,588 A | 7/1991 | Yock et al. |
| 5,041,108 A | 8/1991 | Fox et al. |
| 5,053,033 A | 10/1991 | Clarke |
| 5,055,109 A | 10/1991 | Gould et al. |
| 5,176,674 A | 1/1993 | Hofmann |
| 5,192,278 A | 3/1993 | Hayes et al. |
| 5,281,212 A | 1/1994 | Savage et al. |
| 5,304,171 A | 4/1994 | Gregory et al. |
| 5,334,207 A | 8/1994 | Gay et al. |
| 5,350,375 A | 9/1994 | Deckelbaum et al. |
| 5,354,324 A | 10/1994 | Gregory |
| 5,395,361 A | 3/1995 | Fox et al. |
| 5,423,805 A | 6/1995 | Brucker et al. |
| 5,468,239 A | 11/1995 | Tanner et al. |
| 5,470,330 A | 11/1995 | Goldenberg et al. |
| 5,573,531 A | 11/1996 | Gregory |
| 5,649,923 A | 7/1997 | Gregory et al. |
| 5,709,653 A * | 1/1998 | Leone ............. A61M 25/1027 604/103.01 |
| 5,722,972 A | 3/1998 | Power et al. |
| 5,722,979 A | 3/1998 | Kusleika |
| 5,733,301 A | 3/1998 | Forman |
| 5,741,246 A | 4/1998 | Prescott |
| 5,769,843 A | 6/1998 | Abela et al. |
| 5,876,373 A | 3/1999 | Giba et al. |
| 5,876,397 A | 3/1999 | Edelman et al. |
| 5,944,687 A | 8/1999 | Benett et al. |
| 6,022,309 A | 2/2000 | Celliers et al. |
| 6,024,738 A | 2/2000 | Daikuzono et al. |
| 6,123,718 A | 9/2000 | Tu et al. |
| 6,132,423 A | 10/2000 | Aita et al. |
| 6,210,404 B1 | 4/2001 | Shadduck |
| 6,283,958 B1 | 9/2001 | Vogl et al. |
| 6,379,325 B1 | 4/2002 | Benett et al. |
| 6,551,302 B1 | 4/2003 | Rosinko et al. |
| 6,561,998 B1 | 5/2003 | Roth et al. |
| 6,592,612 B1 | 7/2003 | Samson et al. |
| 6,660,001 B2 | 12/2003 | Gregory |
| 6,752,800 B1 | 6/2004 | Winston et al. |
| 7,125,404 B2 | 10/2006 | Levatter |
| 7,144,248 B2 | 12/2006 | Irwin |
| 7,226,470 B2 | 6/2007 | Kemény et al. |
| 7,238,178 B2 | 7/2007 | Maschke |
| 7,306,585 B2 | 12/2007 | Ross |
| 7,818,053 B2 | 10/2010 | Kassab |
| 7,891,361 B2 | 2/2011 | Irwin |
| 8,104,483 B2 | 1/2012 | Taylor |
| 8,162,964 B2 | 4/2012 | Piippo et al. |
| 8,167,810 B2 | 5/2012 | Maschke |
| 8,396,548 B2 | 3/2013 | Perry |
| 8,454,669 B2 | 6/2013 | Irwin |
| 8,465,452 B2 | 6/2013 | Kassab |
| 8,551,096 B2 | 10/2013 | Perry et al. |
| 8,574,247 B2 | 11/2013 | Adams et al. |
| 8,684,970 B1 | 4/2014 | Koyfman et al. |
| 8,702,773 B2 | 4/2014 | Keeler |
| 8,709,075 B2 | 4/2014 | Adams et al. |
| 8,728,091 B2 | 5/2014 | Hakala et al. |
| 8,747,416 B2 | 6/2014 | Hakala et al. |
| 8,790,386 B2 | 7/2014 | Dwork |
| 8,888,788 B2 | 11/2014 | Hakala et al. |
| 8,956,371 B2 | 2/2015 | Hawkins et al. |
| 8,956,374 B2 | 2/2015 | Hawkins et al. |
| 9,005,216 B2 | 4/2015 | Hakala et al. |
| 9,011,462 B2 | 4/2015 | Adams et al. |
| 9,011,463 B2 | 4/2015 | Adams et al. |
| 9,044,618 B2 | 6/2015 | Hawkins et al. |
| 9,044,619 B2 | 6/2015 | Hawkins et al. |
| 9,072,534 B2 | 7/2015 | Adams et al. |
| 9,138,249 B2 | 9/2015 | Adams et al. |
| 9,180,280 B2 | 11/2015 | Hawkins et al. |
| 9,220,521 B2 | 12/2015 | Hawkins et al. |
| 9,237,984 B2 | 1/2016 | Hawkins et al. |
| 9,320,530 B2 | 4/2016 | Grace |
| 2001/0027310 A1 | 10/2001 | Parisi et al. |
| 2003/0009157 A1 | 1/2003 | Levine |
| 2003/0181938 A1 | 9/2003 | Roth et al. |
| 2003/0229370 A1 | 12/2003 | Miller |
| 2004/0143287 A1 | 7/2004 | Konstantino |
| 2005/0021071 A1 | 1/2005 | Konstantino |
| 2005/0216044 A1 | 9/2005 | Hong |
| 2005/0240212 A1 | 10/2005 | McAuley |
| 2005/0251116 A1 | 11/2005 | Steinke et al. |
| 2006/0189930 A1 | 8/2006 | Lary et al. |
| 2006/0190022 A1 | 8/2006 | Beyar et al. |
| 2007/0078500 A1 | 4/2007 | Ryan et al. |
| 2007/0093745 A1 | 4/2007 | Steward et al. |
| 2007/0198047 A1 | 8/2007 | Schon et al. |
| 2007/0270897 A1 * | 11/2007 | Skerven ............. A61B 1/00082 606/192 |
| 2008/0103575 A1 | 5/2008 | Gerber |
| 2008/0249515 A1 | 10/2008 | Taylor |
| 2009/0112198 A1 | 4/2009 | Khanna et al. |
| 2009/0112239 A1 | 4/2009 | To |
| 2009/0270846 A1 | 10/2009 | Okada et al. |
| 2009/0270850 A1 | 10/2009 | Zhou et al. |
| 2010/0016862 A1 | 1/2010 | Hawkins et al. |
| 2010/0049182 A1 | 2/2010 | Ryan et al. |
| 2010/0152720 A1 | 6/2010 | Sauro et al. |
| 2010/0222786 A1 | 9/2010 | Kassab |
| 2011/0152683 A1 | 6/2011 | Gerrans et al. |
| 2011/0208185 A1 * | 8/2011 | Diamant ............. A61B 18/1492 606/42 |
| 2012/0116289 A1 | 5/2012 | Hawkins et al. |
| 2012/0203255 A1 | 8/2012 | Hawkins et al. |
| 2012/0221013 A1 | 8/2012 | Hawkins |
| 2012/0303011 A1 | 11/2012 | Schaeffer |
| 2013/0030431 A1 | 1/2013 | Adams |
| 2013/0030447 A1 * | 1/2013 | Adams ............... A61B 17/2202 606/128 |
| 2013/0046293 A1 | 2/2013 | Arai et al. |
| 2013/0096545 A1 | 4/2013 | Laudenslager et al. |
| 2013/0197555 A1 | 8/2013 | Schaer |
| 2014/0005576 A1 | 1/2014 | Adams et al. |
| 2014/0039513 A1 | 2/2014 | Hakala |
| 2014/0046229 A1 | 2/2014 | Hawkins et al. |
| 2014/0046353 A1 | 2/2014 | Adams |
| 2014/0052114 A1 | 2/2014 | Ben-Oren et al. |
| 2014/0052145 A1 | 2/2014 | Adams et al. |
| 2014/0074113 A1 | 3/2014 | Hakala et al. |
| 2014/0133814 A1 | 5/2014 | Stevens |
| 2014/0163592 A1 | 6/2014 | Hawkins et al. |
| 2014/0214061 A1 | 7/2014 | Adams |
| 2014/0276682 A1 | 9/2014 | Hendrick et al. |
| 2014/0288570 A1 | 9/2014 | Adams |
| 2015/0039002 A1 | 2/2015 | Hawkins |
| 2015/0073430 A1 | 3/2015 | Hakala et al. |
| 2015/0105714 A1 | 4/2015 | Laudenslager et al. |
| 2015/0238208 A1 | 8/2015 | Adams et al. |
| 2015/0238209 A1 | 8/2015 | Hawkins et al. |
| 2015/0320432 A1 | 11/2015 | Adams |
| 2016/0184022 A1 | 6/2016 | Grace et al. |
| 2016/0184023 A1 | 6/2016 | Grace et al. |
| 2016/0184570 A1 | 6/2016 | Grace et al. |

(56) References Cited

U.S. PATENT DOCUMENTS

| | | |
|---|---|---|
| 2017/0265942 A1 | 9/2017 | Grace et al. |
| 2017/0333132 A1 | 11/2017 | Grace et al. |
| 2018/0008348 A1 | 1/2018 | Grace et al. |

FOREIGN PATENT DOCUMENTS

| | | |
|---|---|---|
| DE | 4240182 C2 | 6/1994 |
| DE | 4437578 A1 | 5/1996 |
| EP | 0182689 B1 | 5/1986 |
| EP | 0189329 A2 | 7/1986 |
| EP | 0355200 A1 | 2/1990 |
| EP | 0820786 A2 | 1/1998 |
| EP | 0902654 B1 | 3/1999 |
| EP | 1200002 B1 | 5/2002 |
| JP | H01148278 A | 6/1989 |
| JP | 2004215862 A | 8/2004 |
| JP | 2009061083 A | 3/2009 |
| KR | 100996733 B1 | 11/2010 |
| WO | WO199006087 A | 6/1990 |
| WO | 1991010403 A1 | 7/1991 |
| WO | WO199745157 A | 12/1997 |
| WO | WO2000012168 A1 | 3/2000 |
| WO | 2003057060 A1 | 7/2003 |
| WO | WO2004060460 A2 | 7/2004 |
| WO | 2006006169 A2 | 1/2006 |
| WO | 2010054048 A2 | 5/2010 |
| WO | 2009152352 A2 | 12/2010 |
| WO | 2011006017 A1 | 1/2011 |
| WO | 2013070750 A1 | 5/2013 |
| WO | 2013169807 A1 | 11/2013 |
| WO | 2014004887 A1 | 1/2014 |
| WO | 2014025397 A1 | 2/2014 |
| WO | 2014025620 A1 | 2/2014 |
| WO | 2014025981 A1 | 2/2014 |
| WO | 2014028885 A1 | 2/2014 |
| WO | 2014043400 A1 | 3/2014 |
| WO | 2014163955 A1 | 10/2014 |
| WO | 2015017499 A1 | 2/2015 |
| WO | 2015034840 A1 | 5/2015 |
| WO | 2015171515 A1 | 11/2015 |

OTHER PUBLICATIONS

International Search Report and Written Opinion issued in PCT/US2014/019268 dated Jun. 13, 2014, 13 pages.
International Search Report and Written Opinion issued in PCT/US2015/068173, dated Apr. 19, 2016, 16 pages.
U.S. Appl. No. 14/984,050 entitled Laser-Induced Fluid Filled Balloon Catheter, filed Dec. 30, 2015.
U.S. Appl. No. 14/984,294 entitled Electrically-Induced Fluid Filled Balloon Catheter, filed Dec. 30, 2015.
U.S. Appl. No. 14/984,308 entitled Laser-Induced Pressure Wave Emitting Catheter Sheath, filed Dec. 30, 2015.
U.S. Appl. No. 15/090,736 entitled "Apparatus and Method for Balloon Angioplasty," filed Apr. 5, 2016.
International Search Report and Written Opinion issued in PCT/US2015/068161, dated May 4, 2016, 19 pages.
International Search Report and Written Opinion issued in PCT/US2015/068169, dated May 13, 2016, 28 pages.
International Search Report and Written Opinion issued in PCT/US2015/068170, dated May 13, 2016, 13 pages.
Supplemental European Search Report issued in EP Application 14778867, dated Aug. 10, 2016, 7 pages.
International Preliminary Report on Patentability issued in PCT/US2015/068161, dated Jul. 13, 2017, 15 pages.
International Search Report and Written Opinion issued in PCT/US2015/068169, dated Jul. 13, 2017, 21 pages.
International Search Report and Written Opinion issued in PCT/US2017/043680, dated Oct. 31, 2017, 14 pages.
International Search Report and Written Opinion issued in PCT/US2017/043762, dated Oct. 31, 2017, 14 pages.

\* cited by examiner

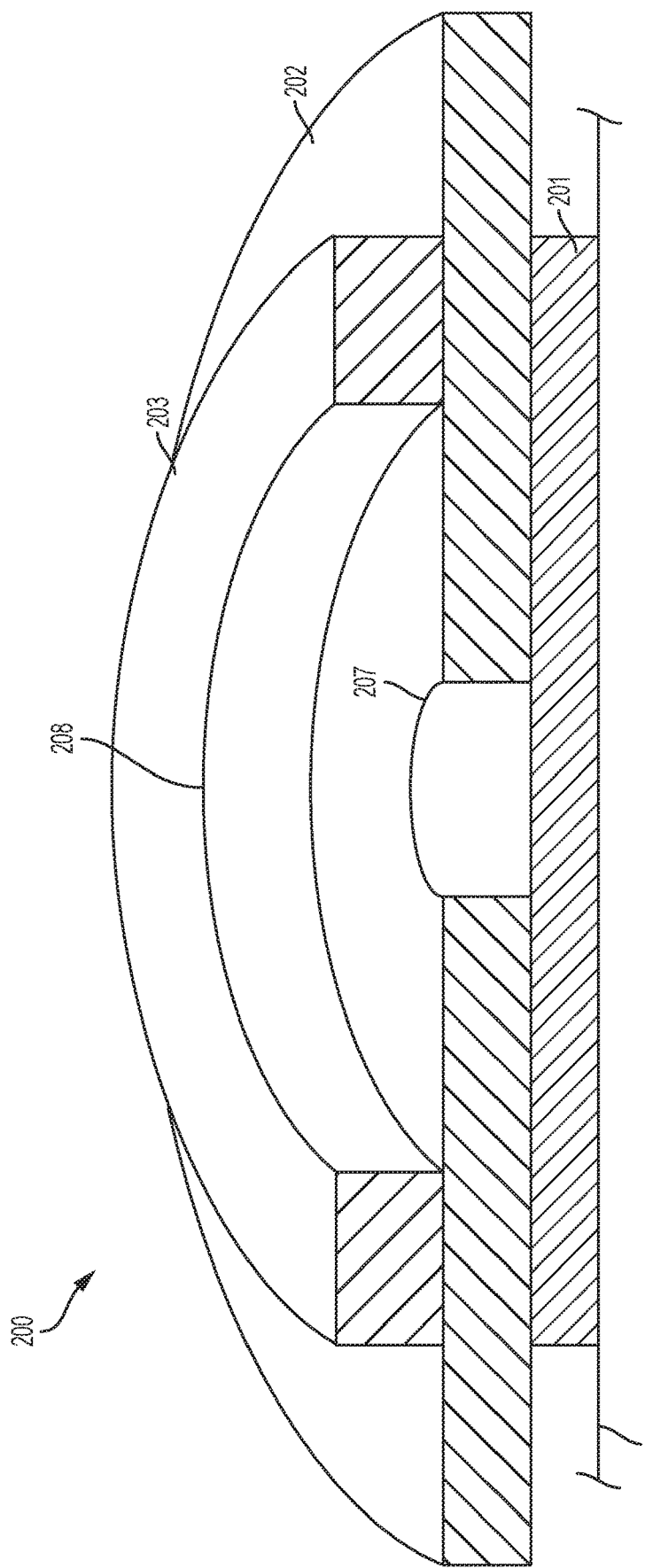

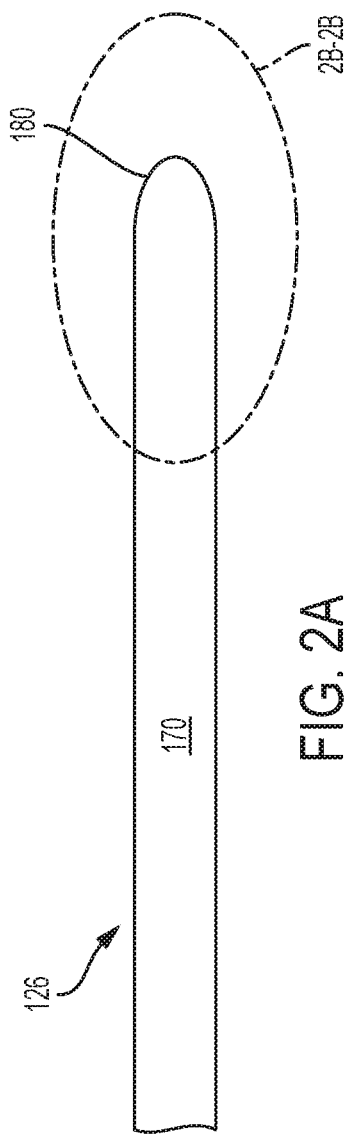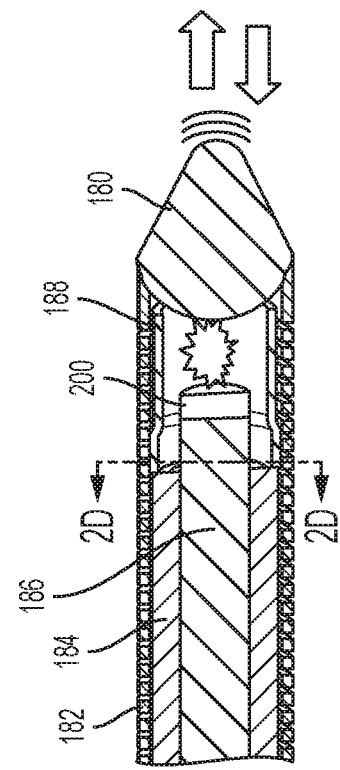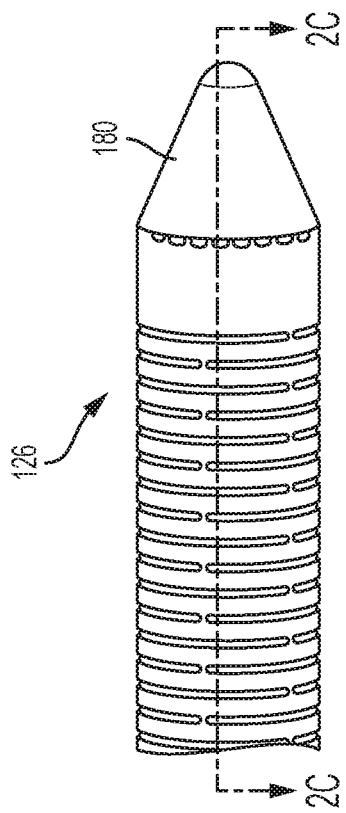
FIG. 2A
FIG. 2B
FIG. 2C

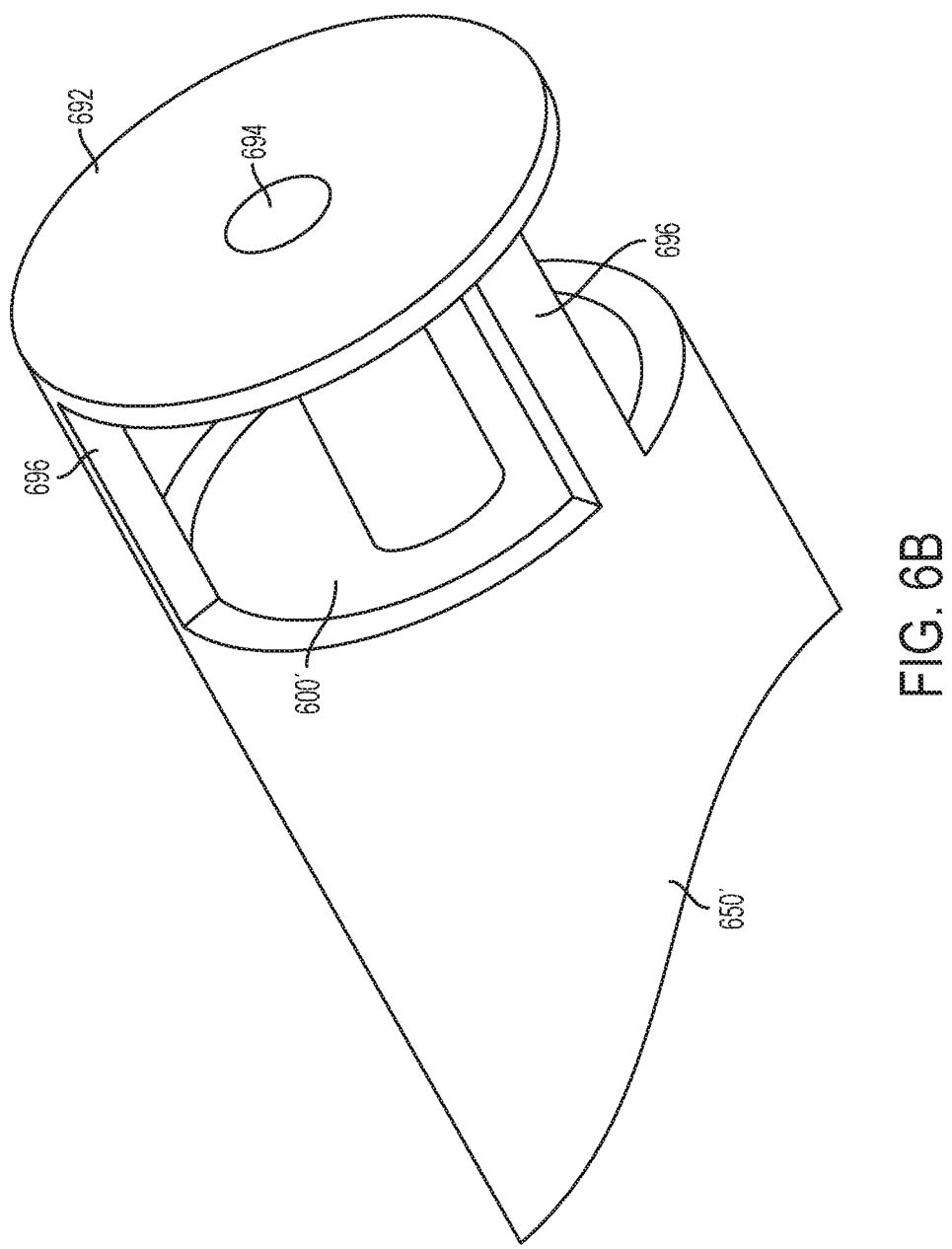

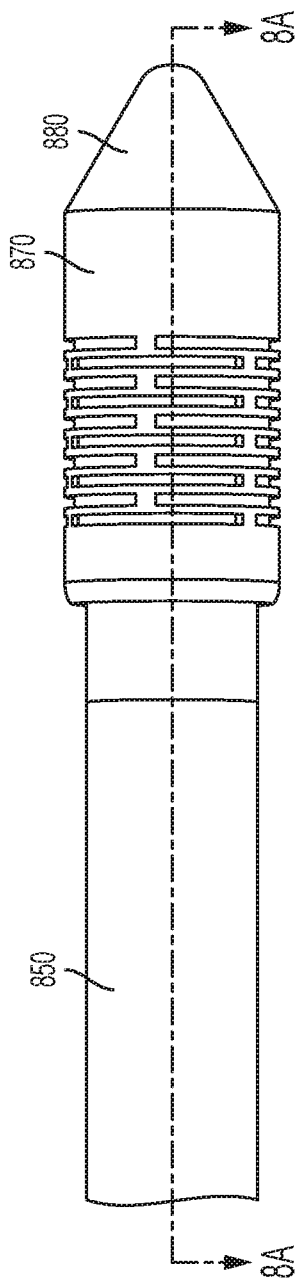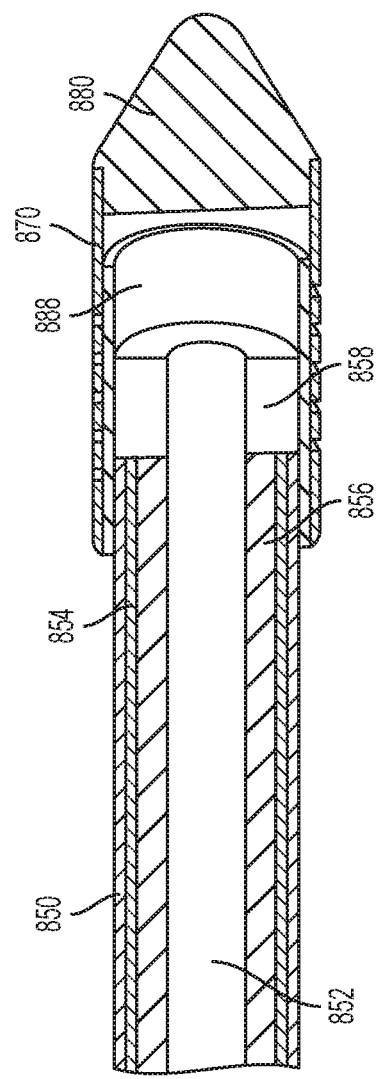
FIG. 8
FIG. 8A

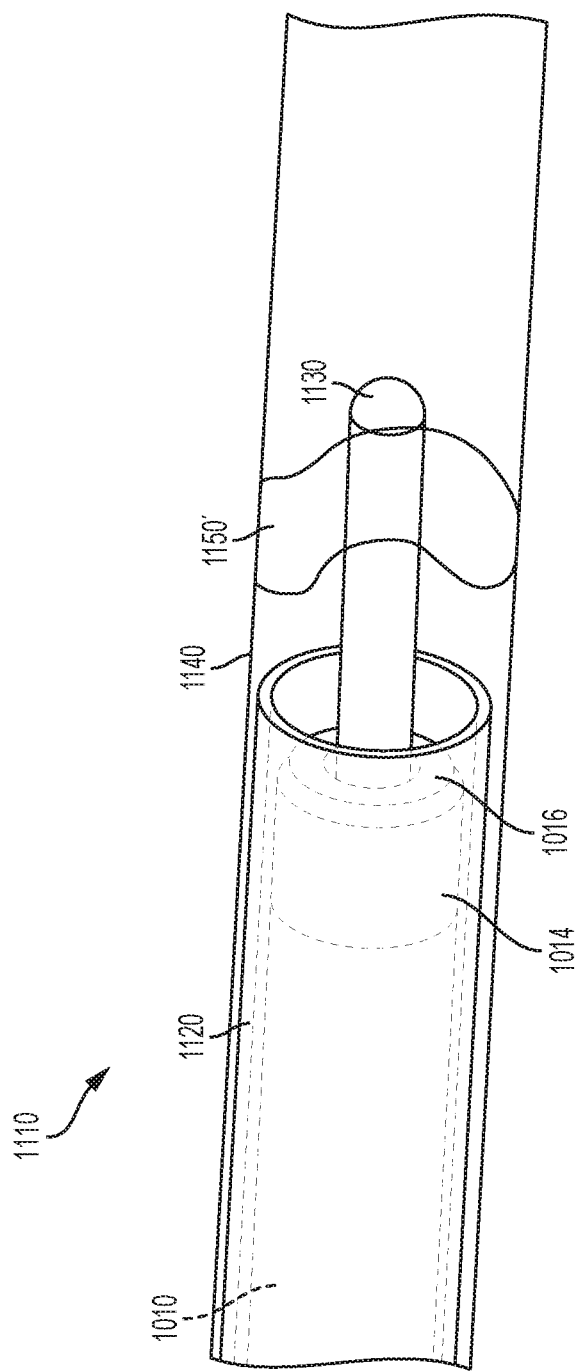

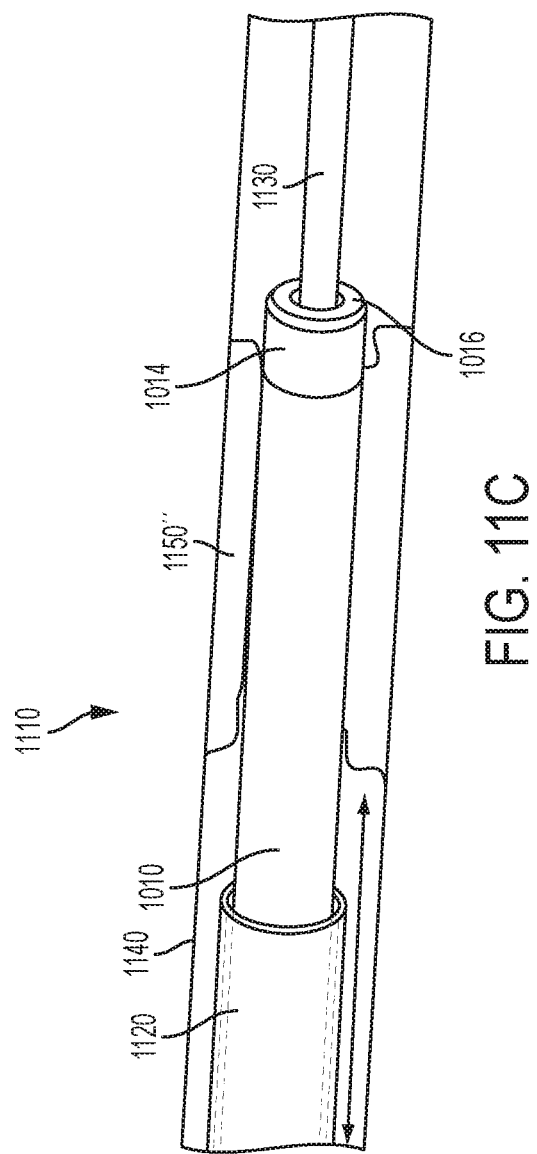

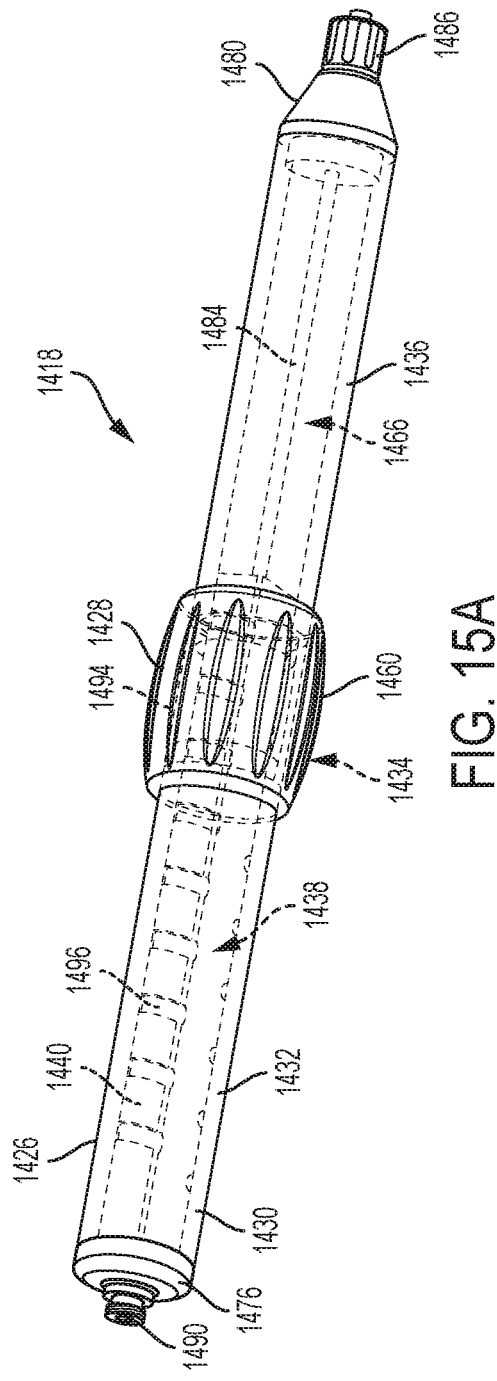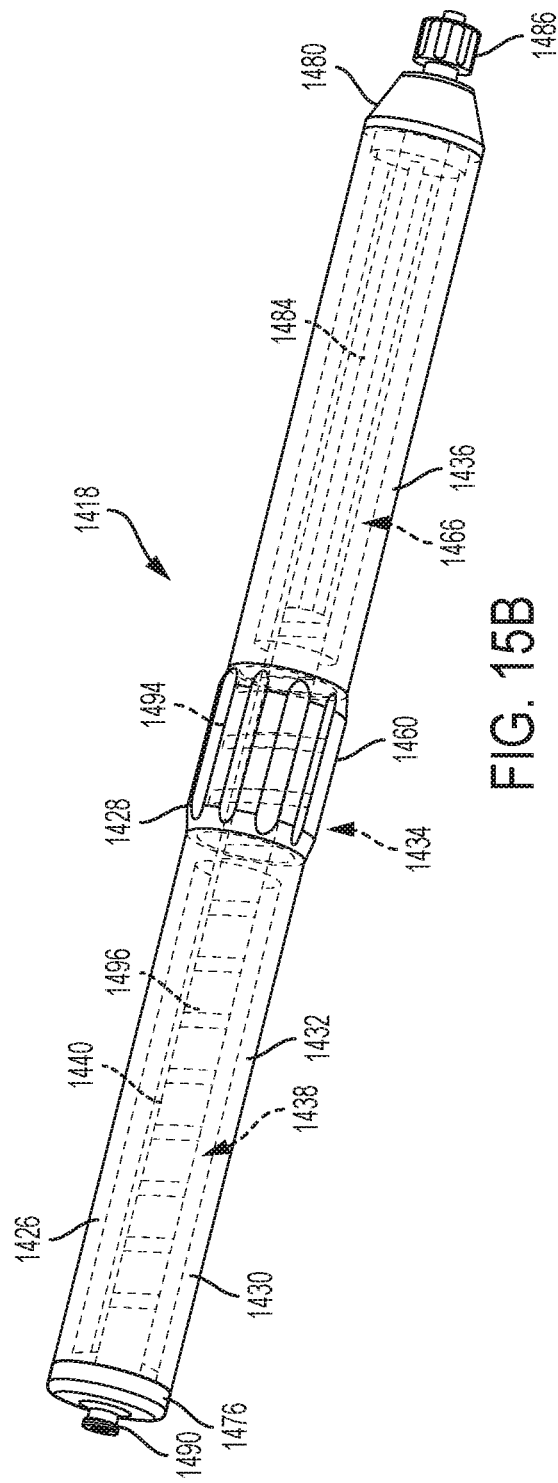
FIG. 15A
FIG. 15B

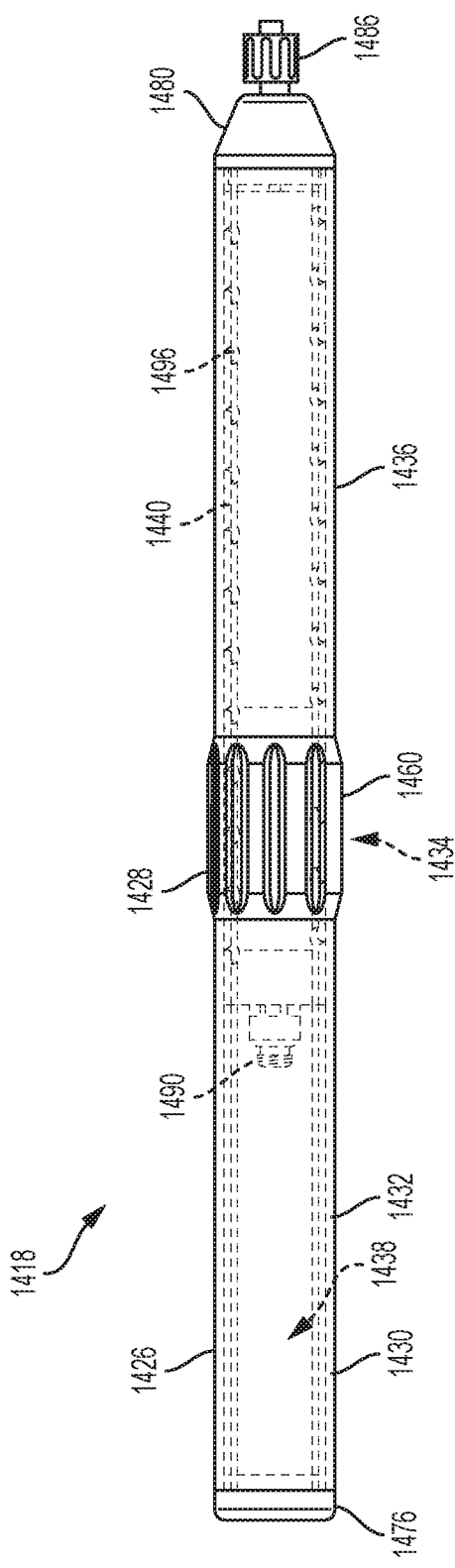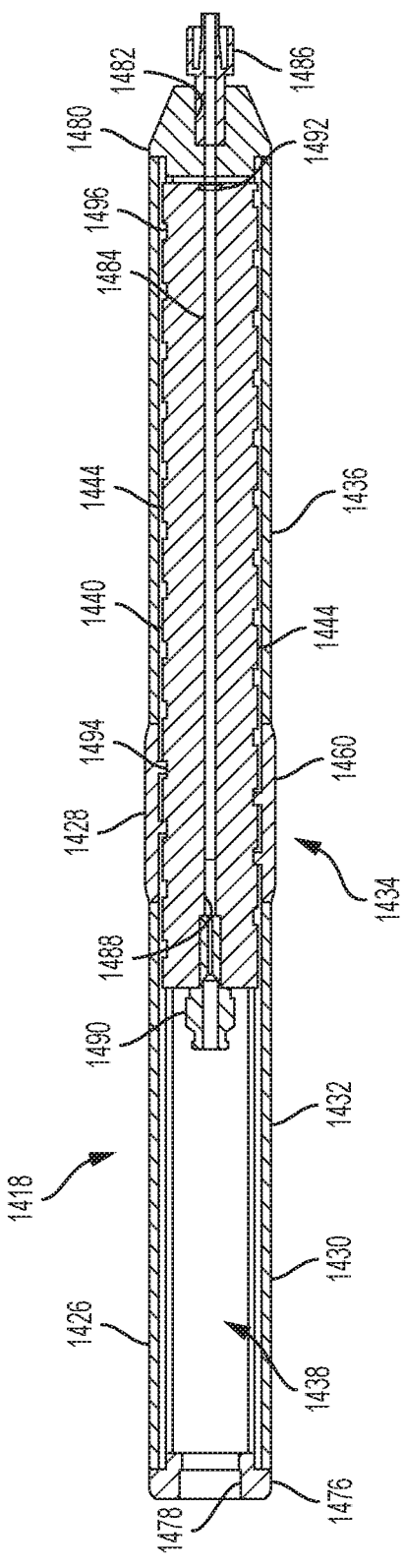
FIG. 15E
FIG. 15F

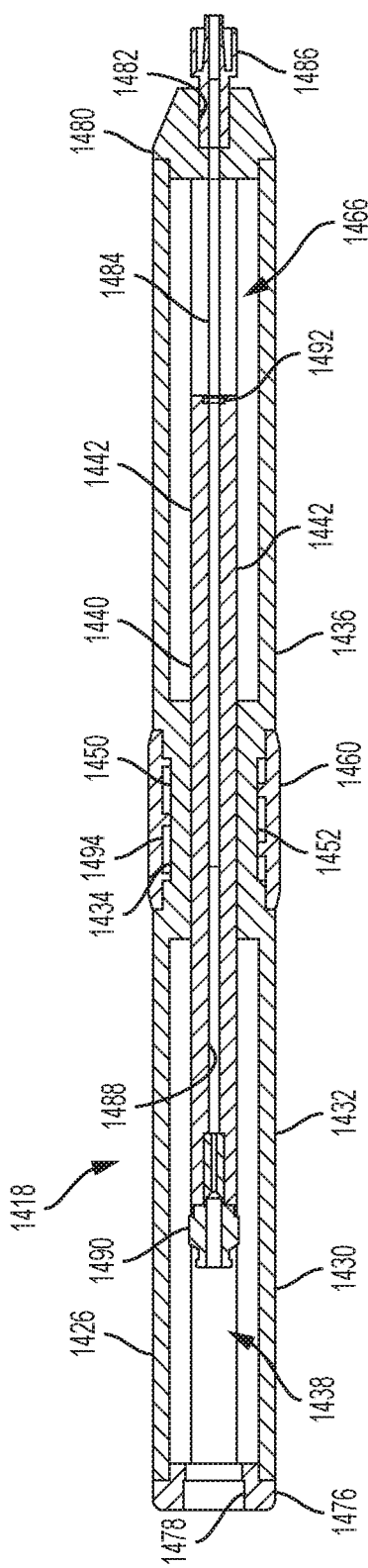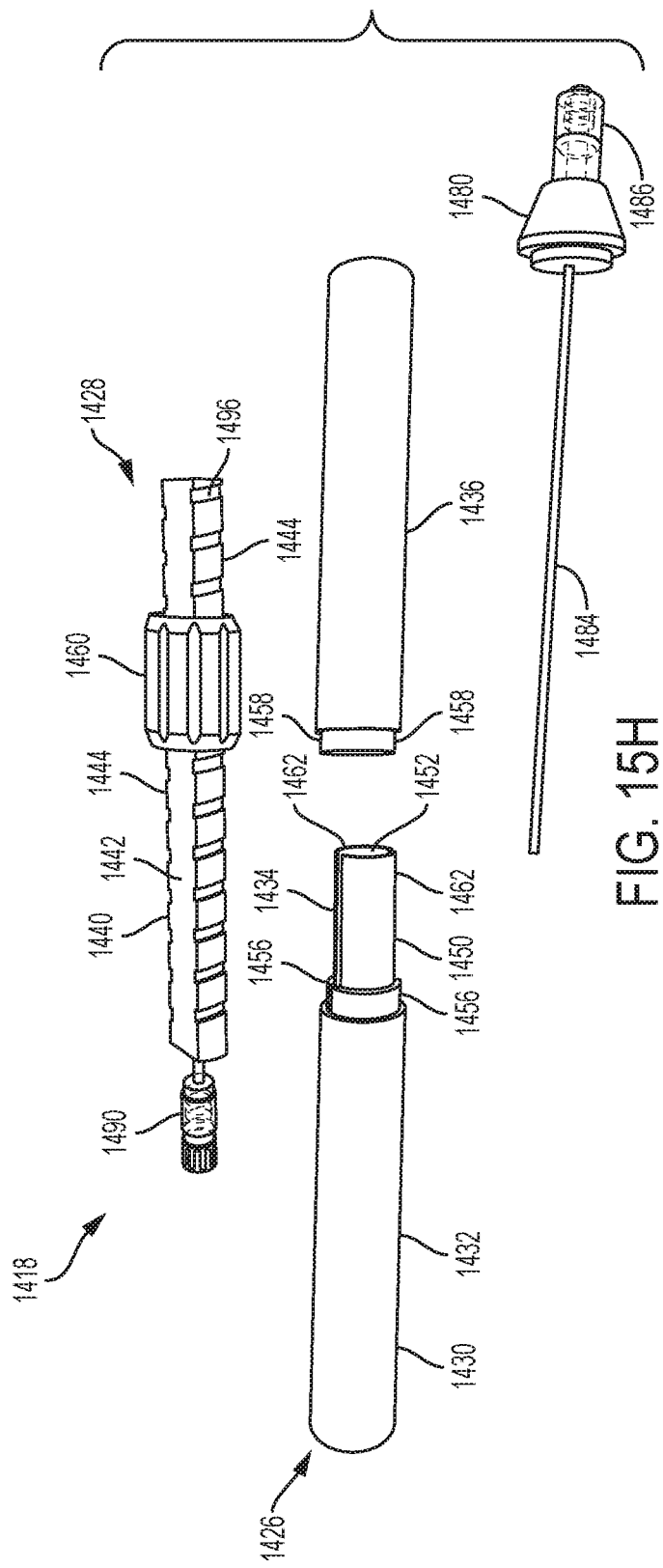
FIG. 15G
FIG. 15H

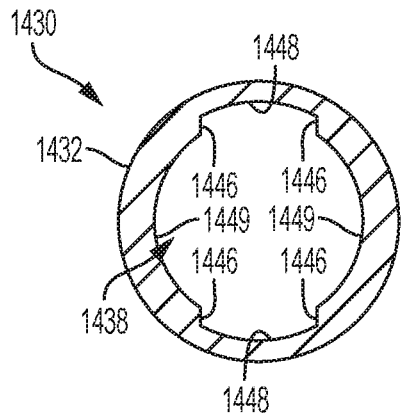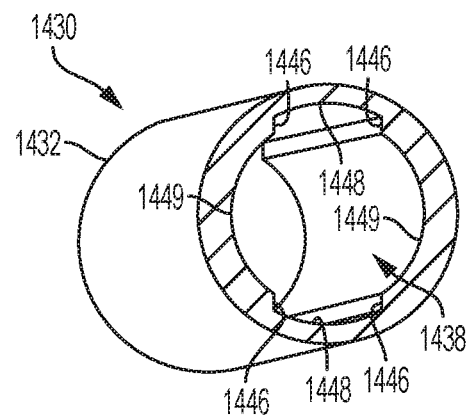
FIG. 16B　　　　　　　FIG. 16C
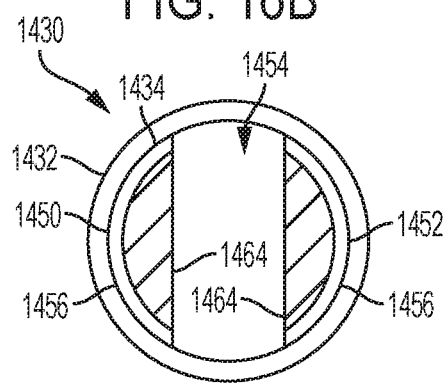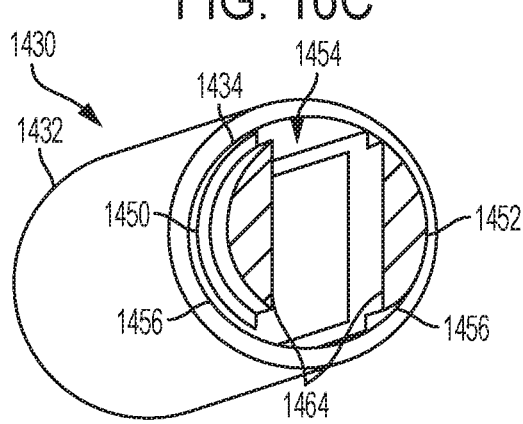
FIG. 16D　　　　　　　FIG. 16E
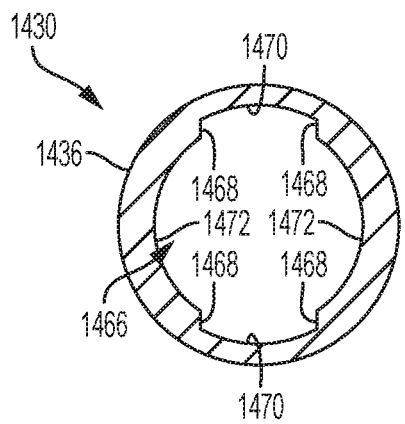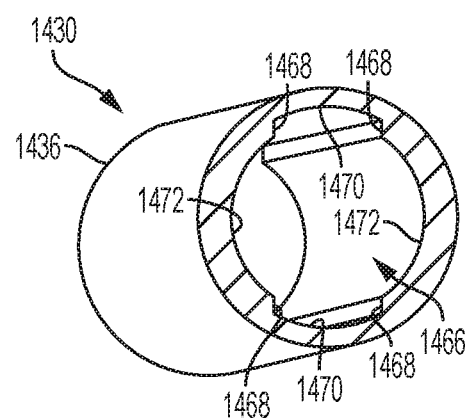
FIG. 16F　　　　　　　FIG. 16G

ELECTRICALLY-INDUCED PRESSURE WAVE EMITTING CATHETER SHEATH

CROSS REFERENCE TO RELATED APPLICATIONS

The present application claims the benefit of and priority, under 35 U.S.C. § 119(e), to commonly assigned, U.S. Application Ser. No. 62/098,242, filed on Dec. 30, 2014 which is hereby incorporated herein by reference in its entirety for all that it teaches and for all purposes. The present application claims the benefit of and priority, under 35 U.S.C. § 119(e), to commonly assigned, U.S. Application Ser. No. 62/209,691, filed on Aug. 25, 2015 which is hereby incorporated herein by reference in its entirety for all that it teaches and for all purposes. The present application claims the benefit of and priority, under 35 U.S.C. § 119(e), to commonly assigned, U.S. Application Ser. No. 62/212,242, filed on Aug. 31, 2015 which is hereby incorporated herein by reference in its entirety for all that it teaches and for all purposes. The present application claims the benefit of and priority, under 35 U.S.C. § 119(e), to commonly assigned, U.S. Application Ser. No. 62/248,753, filed on Oct. 30, 2015 which is hereby incorporated herein by reference in its entirety for all that it teaches and for all purposes. The present application claims the benefit of and priority, under 35 U.S.C. § 119(e), to commonly assigned, U.S. Application Ser. No. 62/248,936, filed on Oct. 30, 2015 which is hereby incorporated herein by reference in its entirety for all that it teaches and for all purposes. The present application claims the benefit of and priority, under 35 U.S.C. § 119(e), to commonly assigned, U.S. Application Ser. No. 62/264,725, filed on Dec. 8, 2015 which is hereby incorporated herein by reference in its entirety for all that it teaches and for all purposes. The present application claims the benefit of and priority, under 35 U.S.C. § 119(e), to commonly assigned, U.S. Application Ser. No. 62/268,797, filed on Dec. 17, 2015 which is hereby incorporated herein by reference in its entirety for all that it teaches and for all purposes.

FIELD

The present disclosure relates generally to the use of medical devices for the treatment of vascular conditions. In particular, the present disclosure provides materials and methods for using electrically-induced pressure waves to disrupt vascular blockages and to deliver therapeutic agents to the blockage area.

BACKGROUND

Arterial disease is a common disease that affects millions of Americans. Coronary artery disease (CAD) most often results from a condition known as atherosclerosis, which generally manifests as the accumulation of a waxy substance on the inside of a subject's coronary arteries. This substance, called plaque, is made of cholesterol, fatty compounds, calcium, and a blood-clotting material called fibrin. Similarly, peripheral artery disease (PAD) often results from the accumulation of plaque on the inside of a subject's peripheral arteries, such as the arteries in a patient's arms, hands, legs and/or feet. As the plaque builds up, the artery narrows, or becomes stenotic, making it more difficult for blood to flow through the arteries. As the size of the stenosis increases and the blockage worsens, blood flow slows and upon the formation of a total occlusion, blood flow through the corresponding artery completely stops, which in turn may cause pain in the extremities and, in severe cases, gangrene, which may ultimately require amputation.

Balloon angioplasty and other transluminal medical treatments are well-known and have been proven efficacious in the treatment of stenotic lesions at the core of CAD and/or PAD, as long as the artery is only partially blocked and not totally blocked. In a typical angioplasty procedure to treat CAD, a catheter is inserted into the groin or arm of a subject and guided forward through the aorta and into the coronary arteries of the heart. The angioplasty catheter includes a balloon, which when placed within the partial occlusion, can be inflated, thereby dilating the occlusion and increasing the size of the diameter of the artery to provides more typical blood flow therethrough.

Over time, an occlusion, particularly a total occlusion, may calcify and/or becomes fibrous, thereby increasing the balloon's ability to dilate the occlusion. Certain types of catheters, such as electrically-induced shockwave balloon catheters, may be used to break the calcified tissue. An electrically-induced shockwave balloon catheter may include a liquid filled balloon and a one or more pairs of electrodes within the balloon. Upon creating a discharge across the electrodes, plasma is produced, which results in the formation of one or more cavitation bubbles. The cavitation bubbles created within the balloon cause the balloon to expand and contract. The expansion and contraction of the balloon creates a hydraulic force that transfers energy to the vascular occlusion and/or to the walls of the vessel in an amount sufficient to disrupt intraluminal as well as medial (within the tissue layer of the vascular wall) vascular obstructions (for example, calcium deposits). In addition to producing cavitation bubbles being upon the formation of plasma generated by the electrical reaction in the liquid, shockwaves are also produced. The shockwaves are transferred through the balloon and to the calcified occlusion, and the shockwaves break the calcified occlusion.

In the event a total stenotic occlusion forms, it may be difficult for the balloon to enter the stenosis. Additionally, if total occlusion calcifies and/or become fibrous, thereby increasing the hardness of occlusion, it may become even more difficult, if not impossible, to penetrate the occlusion and insert a balloon catheter. For example, the proximal and/or distal ends of the occlusion may become calcified to the point that "caps" or "calcified caps" are created, such that even an electrically-induced shockwave balloon catheter may be unable to penetrate the calcified total occlusion because the balloon must be within and adjacent the occlusion in order to operate. And because the balloon within an electrically-induced shockwave balloon catheter is typically proximal the distal end of the electrically-induced shockwave balloon catheter, it is unable to be inserted into or through the calcified cap of the total occlusion.

SUMMARY

What is needed is a device, system, kit and/or method that is capable of penetrating a calcified and/or fibrous total occlusion, particularly a calcified cap(s), and destroying at least a portion of the occlusion as the device penetrates and traverses the total occlusion. What is also needed is a device, system, kit and/or method that is capable of utilizing pressure waves to treat the vascular occlusion by disrupting the calcified and/or fibrous portions without applying a hydraulic force thereto. These and other needs are addressed by the various aspects, embodiments, and configurations of the present disclosure.

The present disclosure provides a catheter comprising an outer sheath having a proximal end and a distal end, a closed tip coupled to the distal end of the outer sheath, an inner sheath having a proximal end and a distal end, wherein the inner sheath is disposed radially within the outer sheath, wherein the distal end of the inner sheath is disposed proximate the closed tip, thereby creating a cavity among the outer sheath, the inner sheath and the tip, at least one electrode assembly coupled to the inner sheath, wherein the electrode assembly comprises a positive electrode and a negative electrode, wherein the electrode assembly is coupled to an electrical pulse generator.

A catheter, wherein the outer sheath is capable of expanding and contracting in the axial direction.

A catheter, wherein the outer sheath is a hypotube.

A catheter further comprising a shield axially disposed within the cavity between the distal end of the inner sheath and the distal end of the outer sheath, wherein the shield comprises a proximal end and a distal end, wherein the shield concentrates pressure waves from the proximal end to the distal end of the shield.

A catheter, wherein the closed tip comprises a proximal end and a distal end, wherein the tip has a solid construction along its longitudinal axis from its proximal end to its distal end.

A catheter, wherein the closed tip comprises a proximal end and a distal end, wherein the tip has a hollow construction along its longitudinal axis from its proximal end to its distal end.

A catheter, wherein the liquid medium is contrast medium or contrast solution.

A catheter, wherein the liquid medium is any one of iodine-containing contrast medium or gadolinium contrast medium.

A catheter, wherein the inners sheath and the at least one electrode is configured to translate within the outer sheath.

A catheter, wherein the closed tip comprises a distal end and a flexible membrane at its distal end.

A catheter, wherein the inner sheath further comprises a first guidewire lumen, and further comprising a sealable valve coupled to the outer sheath, the sealable valve having a second guidewire lumen and a seal, whereupon introducing a guidewire into the first guidewire lumen and the second guidewire lumen and introducing liquid medium to the cavity, the liquid medium actuates the seal within the valve and closes an opening between the valve and the guidewire.

A catheter, wherein the sealable valve further comprises an exterior wall and a flange disposed radially therein, wherein a gap exists between the exterior wall and the flange.

A catheter, wherein the sealable valve comprises a proximal portion and a distal portion, and wherein the flange is disposed toward the proximal portion of the sealable valve.

A catheter, wherein the proximal portion of the sealable valve is tubular.

A catheter, wherein the distal portion of the sealable valve is tapered radially inward from the exterior wall towards the second guidewire lumen.

A catheter, wherein the sealable valve further comprises openings within the exterior wall extending toward the proximal portion.

A catheter, wherein the flange is tapered radially inward towards the second guidewire lumen as the flange progresses from the distal portion toward the proximal portion.

The present disclosure provides a method for treating an obstruction within vasculature of a subject, the method comprising positioning a catheter within vasculature of a subject, the catheter comprising an outer sheath having a proximal end and a distal end, a closed tip coupled to the distal end of the outer sheath, an inner sheath having a proximal end and a distal end, wherein the inner sheath is disposed radially within the outer sheath, wherein the distal end of the inner sheath is disposed proximate the closed tip, thereby creating a cavity among the outer sheath, the inner sheath and the closed tip, a shield axially disposed within the cavity between the distal end of the inner sheath and the tip, at least one electrode assembly coupled to the inner sheath, wherein the electrode assembly comprises a positive electrode and a negative electrode, wherein the electrode assembly is coupled to an electrical pulse generator, and one or more liquid medium ports fluidly coupled to the cavity, positioning the closed tip adjacent an obstruction within the vasculature, introducing a liquid medium into the cavity through the one or more liquid medium ports, activating the at least one electrode assembly within the cavity to transmit pulses of electrical energy into the liquid medium, wherein transmitting the pulses of electrical energy from the electrode assembly into the liquid medium generates a plurality of propagating pressure waves that cause the closed tip to engage and disrupt at least a portion of the vascular obstruction.

A method, wherein the outer sheath is a hypotube capable of expanding and contracting in the axial direction.

A method, wherein the liquid medium is any one of iodine-containing contrast medium or gadolinium contrast medium.

The present disclosure provides a catheter system comprising a sheath having a proximal end and a distal end and a lumen therein, an electrode catheter comprising a proximal end capable of coupling to an electrical pulse generator, a distal end, one or more electrical cables extending from a proximal portion of the electrode catheter to the distal end of the electrode, and at least electrode assembly coupled to the one or more electrical cables, wherein the electrode catheter is configured to be disposed within the sheath, whereupon the distal end of the electrode catheter being disposed proximate the distal end of the sheath, a cavity between the distal end of the electrode catheter and the distal end of the sheath is created, and a means for introducing a liquid medium into the cavity.

The present disclosure provides a catheter comprising a sheath having a proximal end and a distal end and a lumen therein an electrode catheter comprising a proximal end capable of coupling to an electrical pulse generator, a distal end, one or more electrical cables extending from a proximal portion of the electrode catheter to the distal end of the electrode catheter, and at least electrode assembly coupled to the one or more electrical cables, wherein the electrode catheter is disposed within the sheath, whereupon the distal end of the electrode catheter being disposed proximate the distal end of the sheath, a cavity between the distal end of the electrode catheter and the distal end of the sheath is created, a means for introducing a liquid medium into the cavity, a handle comprising a base coupled to the proximal end of the sheath, and a drive mechanism translatably coupled to the base, the drive mechanism coupled to the electrode catheter such that translation of the drive mechanism relative to the base causes translation of the electrode catheter within the lumen of the sheath.

The catheter system, wherein the drive mechanism comprises a control element movably coupled to the base, and a coupling translatably coupled to the base and driven by the control element, the coupling coupled to the electrode catheter such that movement of the control element relative to the base causes translation of the electrode catheter within the lumen of the sheath.

The catheter system, wherein the control element is rotatably coupled to the base, and rotation of the control element relative to the base causes translation of the electrode catheter within the lumen of the sheath.

The catheter system, wherein the control element includes a first threaded surface, and the drive mechanism further includes a shaft that is translatable within the base and coupled to the coupling, the shaft including a second threaded surface, and the second threaded surface coupling to the first threaded surface such that rotation of the control element relative to the base causes translation of the shaft within the base and translation of the electrode catheter within the lumen of the sheath.

The catheter system, wherein the handle further comprises a tube coupled to the base, the tube receiving the electrode catheter, and wherein the shaft includes an inner lumen that translatably receives the tube as the shaft translates within the base.

The catheter system, wherein the drive mechanism further comprises a seal coupled to the shaft, the seal translatably engaging the tube.

The catheter system, wherein the tube is a hypotube.

The catheter system, wherein the base includes a first key feature, the shaft includes a second key feature that couples to the first key feature to inhibit rotation of the shaft relative to the base.

The catheter system, wherein the base includes an opening disposed within the control element, the second threaded surface extending through the opening to couple to the first threaded surface.

The present disclosure provides a handle for coupling to a sheath and an electrode catheter, the handle comprising a base configured to couple to a proximal end of the sheath, and a drive mechanism translatably coupled to the base, the drive mechanism configured to couple to the electrode catheter such that translation of the drive mechanism relative to the base causes translation of the electrode catheter within a lumen of the sheath.

The handle, wherein the drive mechanism comprises a control element movably coupled to the base, and a coupling translatably coupled to the base and driven by the control element, the coupling being configured to couple to the electrode catheter such that movement of the control element relative to the base causes translation of the electrode catheter within the lumen of the sheath.

The handle, wherein the control element is rotatably coupled to the base, and rotation of the control element relative to the base causes translation of the electrode catheter within the lumen of the sheath.

The handle, wherein the control element includes a first threaded surface, and the drive mechanism further includes a shaft that is translatable within the base and coupled to the coupling, the shaft including a second threaded surface, and the second threaded surface coupling to the first threaded surface such that rotation of the control element relative to the base causes translation of the shaft within the base and translation of the electrode catheter within the lumen of the sheath.

The handle, wherein the handle further comprises a tube coupled to the base, the tube receiving the electrode catheter, and wherein the shaft includes a passageway that translatably receives the tube as the shaft translates within the base.

The handle, wherein the drive mechanism further comprises a seal coupled to the shaft, the seal translatably engaging the tube.

The handle, wherein the tube is a hypotube.

The handle, wherein the base includes a first key feature, the shaft includes a second key feature that couples to the first key feature to inhibit rotation of the shaft relative to the base.

The handle, wherein the base includes an opening disposed within the control element, the second threaded surface extending through the opening to couple to the first threaded surface.

The present disclosure provides a catheter comprising an outer sheath having a proximal end, a distal end and a porous attenuating member disposed adjacent the distal end, wherein the porous attenuating member comprises a plurality of openings, an inner sheath having a proximal end and a distal end, wherein the inner sheath is disposed radially within the outer sheath, and at least one electrode assembly coupled to the inner sheath, wherein the electrode assembly comprises a positive electrode and a negative electrode, wherein the at least electrode assembly is coupled to an electrical pulse generator, and wherein the at least one electrode assembly is disposed radially within the outer sheath such that the at least one electrode assembly is disposed radially within the porous attenuating member.

The catheter, wherein the porous attenuating member is constructed to form a semi-rigid biocompatible structure.

The catheter, wherein the porous attenuating member is constructed to form a rigid biocompatible structure.

The catheter, wherein the outer sheath comprises a non-porous biocompatible layer.

The catheter, wherein the porous attenuating member is integrally disposed within the solid biocompatible layer.

The catheter, wherein the porous attenuating member is disposed on the exterior of the solid biocompatible layer.

The catheter, wherein the porous attenuating member is disposed on the interior of the solid biocompatible layer.

The catheter, wherein the plurality of openings comprise at least one of the following shapes: circle; oval; triangle; square; rectangle; polygon; diamond; pentagon; hexagon; heptagon; octagon; nonagon; and decagon.

The catheter, wherein the liquid medium is contrast medium or contrast solution.

The catheter, wherein the liquid medium is any one of iodine-containing contrast medium or gadolinium contrast medium.

The catheter, wherein the at least electrode is configured to translate within the outer sheath.

The catheter, wherein the distal end of the outer sheath comprises an open configuration.

The catheter, wherein the distal end of the outer sheath comprises a closed configuration.

The present disclosure provides a method for treating an obstruction within vasculature of a subject, the method comprising introducing a catheter within vasculature of a subject, the catheter comprising an outer sheath having a proximal end, a distal end and a porous attenuating member disposed adjacent the distal end, wherein the porous attenuating member comprises a plurality of openings, an inner sheath having a proximal end and a distal end, wherein the inner sheath is disposed radially within the outer sheath, at least one electrode assembly coupled to the inner sheath, wherein the electrode assembly is coupled to an electrical generator, wherein the electrode assembly is disposed radially within the outer sheath, one or more liquid medium ports coupled to the at least one lumen, positioning the outer sheath at a location such that the porous attenuating member is adjacent an obstruction within the vasculature, positioning the at least one the electrode assembly the such that the at least one the electrode assembly is disposed radially within the porous attenuating member, introducing a liquid medium into the outer sheath, energizing the at least one the electrode assembly to produce pulses of electrical energy in the liquid medium, wherein producing the pulses of electrical energy from the electrode assembly in the liquid medium generates a plurality of propagating pressure waves that pass through the outer sheath and the openings in the porous attenuating member and disrupt at least a portion of the obstruction.

The present disclosure provides a kit comprising an outer sheath having a proximal end, a distal end and a porous attenuating member disposed adjacent the distal end, wherein the porous attenuating member comprises a plurality of openings, and an electrode catheter configured to be disposed within the porous attenuating member, the electrode catheter comprising an inner sheath having a proximal end and a distal end, wherein the inner sheath is configured to be disposed radially within the outer sheath, one or more electrical cables disposed within the inner sheath extending from a proximal portion of the inner sheath to the distal end of the inner sheath, wherein a proximal end of the one or more electrical cables is configured to be coupled to an electrical pulse generator, and at least one electrode assembly coupled to the one or more electrical cables, wherein the at least one electrode assembly is configured to be disposed radially within the outer sheath such that the at least one electrode assembly is disposed radially within the porous attenuating member.

The present disclosure provides a method for treating an obstruction within vasculature of a subject, the method comprising introducing an outer sheath within vasculature of a subject, wherein the outer sheath comprises a proximal end, a distal end and a porous attenuating member disposed adjacent the distal end, wherein the porous attenuating member comprises a plurality of openings, introducing an electrode catheter within the vasculature of the subject, wherein the electrode catheter is configured to be disposed within the porous attenuating member, wherein the electrode catheter comprises an inner sheath having a proximal end and a distal end, wherein the inner sheath is configured to be disposed radially within the outer sheath, one or more electrical cables disposed within the inner sheath extending from a proximal portion of the inner sheath to the distal end of the inner sheath, wherein a proximal end of the one or more electrical cables is configured to be coupled to an electrical pulse generator, and at least one electrode assembly coupled to the one or more electrical cables, wherein the at least one electrode assembly is configured to be disposed radially within the outer sheath such that the at least one electrode assembly is disposed radially within the porous attenuating member positioning the outer sheath at a location such that the porous attenuating member is adjacent a portion of an obstruction within the vasculature, positioning the at least one electrode assembly such that the at least one electrode assembly is disposed radially within the porous attenuating member, introducing a liquid medium into the outer sheath, activating the at least electrode assembly to produce pulses of electrical energy in the liquid medium, wherein producing the pulses of electrical energy from the electrode assembly in the liquid medium generates a plurality of propagating pressure waves that pass through the outer sheath and the openings in the porous attenuating member and disrupt at least a portion of the obstruction.

The method further comprising the step of re-positioning the outer sheath such that the porous attenuating member is adjacent another portion of the obstruction.

The method further comprising the step of re-positioning the electrode catheter within outer sheath.

The method, wherein the within the electrode catheter is re-positioned within the porous attenuating member.

The method further comprising the step of re-positioning the electrode catheter within outer sheath.

The method, wherein the within the electrode catheter is re-positioned within the porous attenuating member.

The method further comprising the steps of removing the electrode catheter from the vasculature and removing the outer sheath from the vasculature.

The method further comprising the step of inserting a drug-coated balloon into the vasculature such that the drug-coated balloon is disposed adjacent a remaining portion of the occlusion.

The method further comprising the step of inflating the drug-coated balloon and applying a drug disposed on the drug-coated balloon to the remaining portion of the occlusion.

The present disclosure provides a catheter comprising a sheath having a guidewire lumen, a proximal end, and a distal end, at least one electrode assembly disposed adjacent to the guidewire lumen, wherein the at least one electrode assembly produced electrical energy, and means for directing electrical energy produced by the at least one electrode assembly towards the guidewire lumen or a guidewire within the guidewire lumen.

The catheter, wherein the means for directing electrical energy produced by the at least one electrode assembly towards the guidewire lumen or a guidewire within the guidewire lumen comprises an outer band coupled to the distal end of the sheath, wherein the outer band comprises a distal end, and the at least one electrode assembly is disposed proximate the distal end of the outer band.

The catheter, wherein the at least one electrode assembly is directed at the guidewire lumen or a guidewire within the guidewire lumen.

The catheter, wherein the means for electrical energy produced by the at least one electrode assembly towards the guidewire lumen or a guidewire comprises a cap coupled to the distal end of the sheath.

The catheter, wherein the cap comprises an interior side and an exterior side, wherein the interior side is tapered to direct electrical energy produced by the at least one electrode assembly towards the guidewire lumen or a guidewire within the guidewire lumen.

The catheter, wherein the at least one electrode assembly is disposed proximate the interior side of the cap.

The catheter, wherein the sheath is an inner sheath, and further comprising an outer sheath translatably receiving the inner sheath.

The catheter, wherein the outer sheath comprises a sleeve, and wherein the means for directing electrical energy produced by the at least one electrode assembly towards the guidewire lumen or a guidewire within the guidewire lumen comprises an attenuating member of the outer sheath coupled to the sleeve.

The catheter, wherein the attenuating member comprises an inner surface, an outer surface, and a plurality of openings extending from the inner surface to the outer surface.

The catheter, wherein the plurality of openings comprise at least one of the following shapes: circle; oval; triangle; square; rectangle; polygon; diamond; pentagon; hexagon; heptagon; octagon; nonagon; and decagon.

The present disclosure provides a method for treating an obstruction within vasculature of a subject, the method comprising positioning a catheter within the vasculature of the subject, the catheter comprising a sheath having a guidewire lumen, a proximal end, and a distal end, at least one electrode assembly coupled to the sheath, means for directing electrical energy produced by the at least one electrode assembly towards the guidewire lumen or a guidewire within the guidewire lumen, positioning the distal end of the sheath adjacent the obstruction within the vasculature, delivering a liquid medium to the distal end of the sheath, activating the at least one electrode assembly to produces pulses of electrical energy in the liquid medium, wherein producing the pulses of electrical energy from the at least one electrode in the liquid medium generates a plurality of propagating pressure waves that disrupt at least a portion of the obstruction, and wherein the means for directing electrical energy produced by the at least one electrode assembly towards the guidewire lumen or a guidewire within the guidewire lumen induces vibrations within the guidewire.

The method, wherein the means for directing electrical energy produced by the at least one electrode assembly towards the guidewire lumen or a guidewire within the guidewire lumen comprises an outer band coupled to the distal end of the sheath, wherein the outer band comprises a distal end, and the at least one electrode assembly is disposed proximate the distal end of the outer band.

The method, wherein the at least one electrode assembly is directed at the guidewire lumen or a guidewire in the guidewire lumen.

The method, wherein the means for directing electrical energy produced by the at least one electrode assembly towards the guidewire lumen or a guidewire comprises a cap coupled to the distal end of the sheath.

The method, wherein the cap comprises an interior side and an exterior side, wherein the interior side is tapered to direct electrical energy produced by the at least one electrode assembly towards the guidewire lumen or a guidewire within the guidewire lumen.

The method, wherein the at least one electrode assembly is disposed proximate the interior side of the cap.

The method, wherein the sheath is an inner sheath, and wherein the catheter further comprises an outer sheath translatably receiving the inner sheath.

The method, wherein the outer sheath comprises a sleeve, and wherein the means for directing electrical energy produced by the at least one electrode assembly towards the guidewire lumen or a guidewire within the guidewire lumen comprises an attenuating member of the outer sheath coupled to the sleeve.

The method, wherein the attenuating member comprises an inner surface, an outer surface, and a plurality of openings extending from the inner surface to the outer surface, and wherein transmitting the pulses of electrical energy produced by the at least one electrode assembly in the liquid medium generates a plurality of propagating pressure waves that pass through the plurality of openings.

The method, wherein the plurality of openings comprise at least one of the following shapes: circle; oval; triangle; square; rectangle; polygon; diamond; pentagon; hexagon; heptagon; octagon; nonagon; and decagon.

As used herein, "at least one," "one or more," and "and/or" are open-ended expressions that are both conjunctive and disjunctive in operation. For example, each of the expressions "at least one of A, B and C," "at least one of A, B, or C," "one or more of A, B, and C," "one or more of A, B, or C," and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (for example, $X_1$ and $X_2$) as well as a combination of elements selected from two or more classes (for example, $Y_1$ and $Z_o$).

It is to be noted that the term "a" or "an" entity refers to one or more of that entity. As such, the terms "a" (or "an"), "one or more" and "at least one" can be used interchangeably herein. It is also to be noted that the terms "comprising," "including," and "having" can be used interchangeably.

The term "catheter" as used herein generally refers to a tube that can be inserted into a body cavity, duct, lumen, or vessel, such as the vasculature system. In most uses, a catheter is a relatively thin, flexible tube ("soft" catheter), though in some uses, it may be a larger, solid-less flexible—but possibly still flexible—catheter ("hard" catheter).

The term "electrically-induced pressure wave" as used herein is a pressure wave caused by an explosion due to the interaction of electrical energy, such as an electrical and/or plasma arc, and a fluid. The electrically-induced pressure wave may be produced in air or liquid, such as saline that includes a contrast medium.

The term "means" as used herein shall be given its broadest possible interpretation in accordance with 35 U.S.C. § 112(f). Accordingly, a claim incorporating the term "means" shall cover all structures, materials, or acts set forth herein, and all of the equivalents thereof. Further, the structures, materials or acts and the equivalents thereof shall include all those described in the summary, brief description of the drawings, detailed description, abstract, and claims themselves.

The term "porous attenuating member" as used herein shall mean a rigid member or semi-rigid member having openings therein. Examples of a rigid member and a semi-rigid member include a member constructed of coils, braids, laser-cut tubing, reinforced polymer extrusions, patterned plastics, metals and ceramics. Specific materials used to construct such rigid member and a semi-rigid member may include nitinol, stainless steel, titanium, silver, aluminum, cobalt, chromium, pebax, silicone, urethane, polyethylene and derivatives, nylons, polytetrafluoroethylene and derivatives, polyethylene terephthalate, polypropylene, poly(ether ether ketone), hydroxyapatite, alumina, tricalcium phosphate, silicates or other biocompatible metals, ceramics or polymers. Possible configurations for the porous attenuating member include, but are not limited to, spiral cuts, interrupted spiral cut, honeycomb, lattice structures as found commonly in vascular stents, slots, offset slots, helices, slits that are either longitudinal, radial, circumferential, or a combination thereof, openings that are shaped cutouts.

The term "pressure wave" as used herein includes both a shock wave and a sound wave, wherein the shock wave is a pressure wave that moves above the velocity of sound, and the sound wave is a pressure wave that moves at or below the speed of sound.

The term "rigid structure" as used herein shall mean a structure that is able to bend or otherwise conform to the shape of the vasculature as it passes therethrough but is substantially unable to expand and/or contract in the radial direction upon a pressure wave passing therethrough.

The term "semi-rigid structure" as used herein shall mean a structure that is partly rigid with an additional degree of flexibility as it passes through the vasculature but is substantially unable to expand and/or contract in the radial direction upon a pressure wave passing therethrough.

The term "shock wave" as used herein shall mean a region of abrupt change of pressure moving as a wave front above the velocity of sound.

The term "sound wave" as used herein is pressure wave of audible or inaudible sound. That is, a sound wave is a pressure wave that moves at or below the speed of sound. An "acoustic wave" may also be referred to as a sound wave.

The term "therapeutic agent" as used herein generally refers to any known or hereafter discovered pharmacologically active agent that provides therapy to a subject through the alleviation of one or more of the subject's physiological symptoms. A therapeutic agent may be a compound that occurs in nature, a chemically modified naturally occurring compound, or a compound that is chemically synthesized. The agent will typically be chosen from the generally recognized classes of pharmacologically active agents, including, but not necessarily limited to, the following: analgesic agents; anesthetic agents; antiarthritic agents; respiratory drugs, including antiasthmatic agents; anticancer agents, including antineoplastic drugs; anticholinergics; anticonvulsants; antidepressants; antidiabetic agents; antidiarrheal s; antihelminthics; antihistamines; antihyperlipidemic agents; antihypertensive agents; anti-infective agents such as antibiotics and antiviral agents; antiinflammatory agents; antimigraine preparations; antinauseants; antiparkinsonism drugs; antipruritics; antipsychotics; antipyretics; antispasmodics; antitubercular agents; antiulcer agents; antiviral agents; anxiolytics; appetite suppressants; attention deficit disorder (ADD) and attention deficit hyperactivity disorder (ADHD) drugs; cardiovascular preparations including calcium channel blockers, CNS agents; beta-blockers and antiarrhythmic agents; central nervous system stimulants; cough and cold preparations, including decongestants; diuretics; genetic materials; herbal remedies; hormonolytics; hypnotics; hypoglycemic agents; immunosuppressive agents; leukotriene inhibitors; mitotic inhibitors; restenosis inhibitors; muscle relaxants; narcotic antagonists; nicotine; nutritional agents, such as vitamins, essential amino acids and fatty acids; ophthalmic drugs such as antiglaucoma agents; parasympatholytics; psychostimulants; sedatives; steroids; sympathomimetics; tranquilizers; and vasodilators including general coronary, peripheral and cerebral.

The terms "vasculature" and "vascular" as used herein refer to any part of the circulatory system of a subject, including peripheral and non-peripheral arteries and veins. Vascular material found within the vasculature can be comprised of both biological material (for example, nucleic acids, amino acids, carbohydrates, polysaccharides, lipids and the like) and non-biological material (for example, fat deposits, fibrous tissue, calcium deposits, remnants of dead cells, cellular debris and the like).

It should be understood that every maximum numerical limitation given throughout this disclosure is deemed to include each and every lower numerical limitation as an alternative, as if such lower numerical limitations were expressly written herein. Every minimum numerical limitation given throughout this disclosure is deemed to include each and every higher numerical limitation as an alternative, as if such higher numerical limitations were expressly written herein. Every numerical range given throughout this disclosure is deemed to include each and every narrower numerical range that falls within such broader numerical range, as if such narrower numerical ranges were all expressly written herein.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

FIG. 1C is a cut away perspective view of one variation of an electrode assembly for inclusion in an electrode catheter that can be in the electrically-induced pressure wave emitting catheter sheath system of FIGS. 1, 1A and 1B;

FIG. 1I is an elevation view of an enlarged portion an electrode catheter depicted in FIG. 1G with the inclusion of a deflector;

FIG. 2A is a schematic view of a distal portion of the electrically-induced pressure wave emitting catheter sheath of FIG. 1, according to one embodiment of the present disclosure;

FIG. 2C' is a cross-sectional view (along line 2C'-2C' in FIG. 2B') of the distal portion of the electrically-induced pressure wave emitting catheter, according to one embodiment of the present disclosure;

FIG. 6B is an enlarged partial perspective view of the distal portion of an alternative electrode catheter including a deflector coupled to the distal end of the electrode catheter;

FIG. 8 is an elevation view of a removable tip for an electrode catheter, according to one embodiment of the present disclosure;

FIG. 8A is a cross-sectional view (along line 8A-8A in FIG. 8) of a removable tip for an electrode catheter;

FIG. 15A is a perspective view of the handle of FIG. 14A, wherein several external components are partially transparent to illustrate internal components, and a shaft of the handle is shown in a proximal position;

FIG. 15B is another perspective view of the handle of FIG. 14A, wherein several external components are partially transparent to illustrate internal components, and the shaft is shown in the proximal position;

FIG. 15E is an elevation view of the handle of FIG. 14A, wherein several external components are partially transparent to illustrate internal components, and the shaft is shown in a distal position;

FIG. 15F is a cross-sectional view of the handle of FIG. 14A, wherein the shaft is shown in the proximal position;

FIG. 15G is a cross-sectional view of the handle of FIG. 14A, wherein the shaft is shown in an intermediate position;

FIG. 15H is an exploded view of the handle of FIG. 14A;

FIG. 16B is an elevation cross-sectional view of the frame along line 16B-16B of FIG. 16A;

FIG. 16C is a perspective cross-sectional view of the frame along line 16B-16B of FIG. 16A;

FIG. 16D is an elevation cross-sectional view of the frame along line 16D-16D of FIG. 16A;

FIG. 16E is a perspective cross-sectional view of the frame along line 16D-16D of FIG. 16A;

FIG. 16F is an elevation cross-sectional view of the frame along line 16F-16F of FIG. 16A;

FIG. 16G is a perspective cross-sectional view of the frame along line 16F-16F of FIG. 16A.

FIG. 20' is a representative cross-sectional view of the distal end of the catheter illustrated in FIG. 20, according to an alternate embodiment of the present disclosure.

FIG. 20" is a representative cross-sectional view of the distal end of the catheter illustrated in FIG. 20, according to another alternate embodiment of the present disclosure.

DETAILED DESCRIPTION

The present disclosure relates generally to the use of medical devices for the treatment of vascular conditions. In particular, the present disclosure provides materials and methods for using electrically-induced pressure waves to disrupt vascular blockages and to deliver therapeutic agents to the blockage area.

Figure 1:
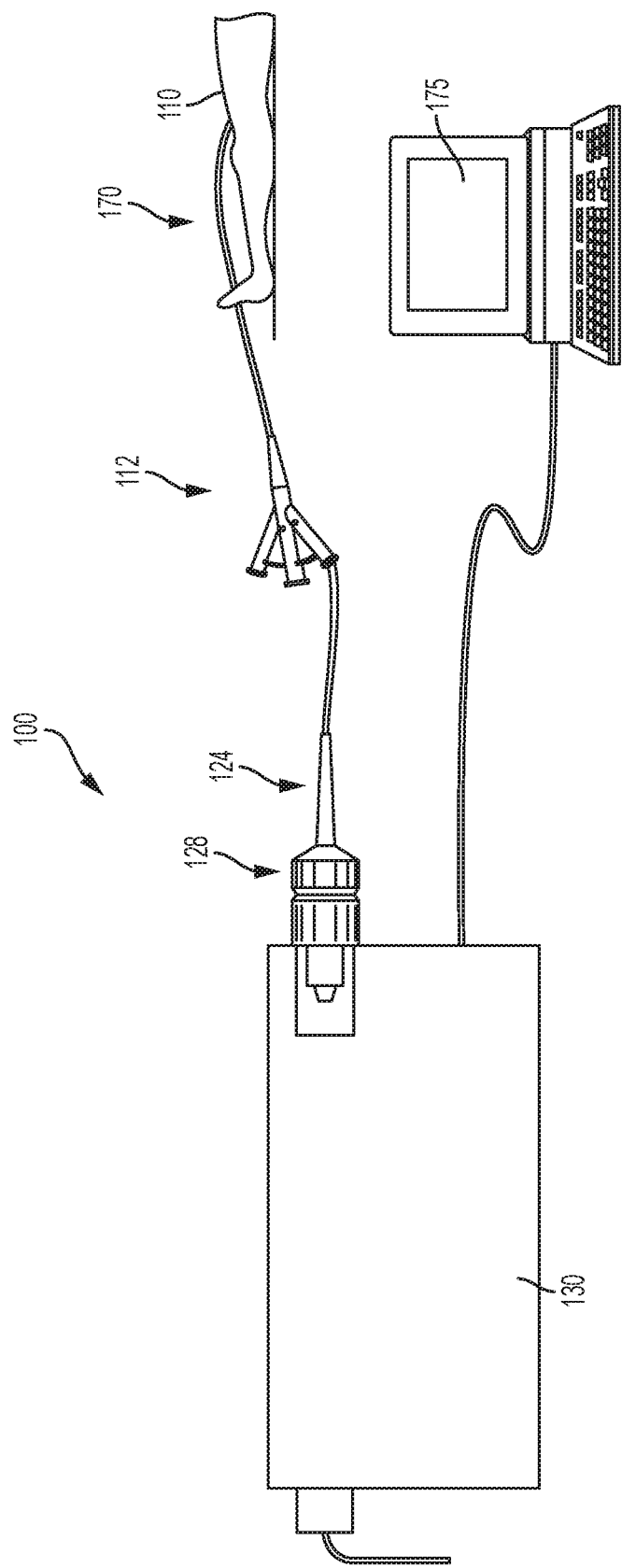
FIG. 1 illustrates an exemplary electrically-induced angioplasty catheter system, including a high voltage pulse generator and an electrically-induced pressure wave emitting catheter sheath system.

Referring to FIG. 1, there is depicted an exemplary electrically-induced angioplasty catheter sheath system 100, including a high voltage pulse generator 130 and an electrically-induced pressure wave emitting catheter 170 coupled to the high voltage pulse generator 130 of the present disclosure. The catheter sheath system 100 includes a high voltage pulse generator 130 coupled to a generator controller 175. Controller 175 includes one or more computing devices programmed to control high voltage pulse generator 130. Controller 175 may be internal or external to generator 130.

The high voltage pulse generator 130 is connected with the proximal end of an electrode catheter 170 via a coupler 128. Electrode catheter 170 includes one or more wires which receive electrical energy from high voltage pulse generator 130 and transports the received electrical energy from a first, proximal end 124 of electrode energy catheter 170 towards a second, distal end 126 of electrode catheter 170. The distal end of catheter 170 may be inserted into a vessel or tissue of a human body 110.

The high voltage pulse generator controller 175 of FIG. 1 includes a non-transitory computer-readable medium (for example, memory) that includes instructions that, when executed, cause one or more processors to control generator 130 and/or other components of the electrically-induced catheter sheath system 100. Controller 175 includes one or more input devices to receive input from an operator. Exemplary input devices include keys, buttons, touch screens, dials, switches, mouse, and trackballs which providing user control of generator 130. Controller 175 further includes one or more output devices to provide feedback or information to an operator. Exemplary output devices include a display, lights, audio devices which provide user feedback or information.

FIG. 1 depicts the catheter 170 entering the leg, preferably through the femoral artery, of the human body. As discussed above, it may be desirable to treat either CAD or PAD. After entering the femoral artery, it the catheter 170 is intended to treat CAD, the catheter 170 will be directed through the patient's vasculature system and to the coronary arteries. Alternatively, if the catheter 170 is intended to treat PAD, the catheter 170 will be directed through the patient's vasculature system and to the peripheral arteries, such as the vasculature below the knee, particularly the vasculature in the patient's legs and/or feet. Unlike balloon catheters, the catheter 170 of the present disclosure is able to more easily navigate and enter smaller sized vasculature because the overall diameter of the sheath is smaller in comparison to balloon catheters, thereby allowing the catheter 170 of the present disclosure more easily treat PAD. That is, the increased size of a balloon of an electrically-induced pressure wave balloon catheter and/or a typical dilation balloon catheter (in comparison to the catheter 170 of the present disclosure) may prevent or increase the difficulty of the balloon-type catheter from entering, penetrating and/or treating the peripheral vasculature, such the vasculature below the knee in the legs and/or feet.

Figure 1A:
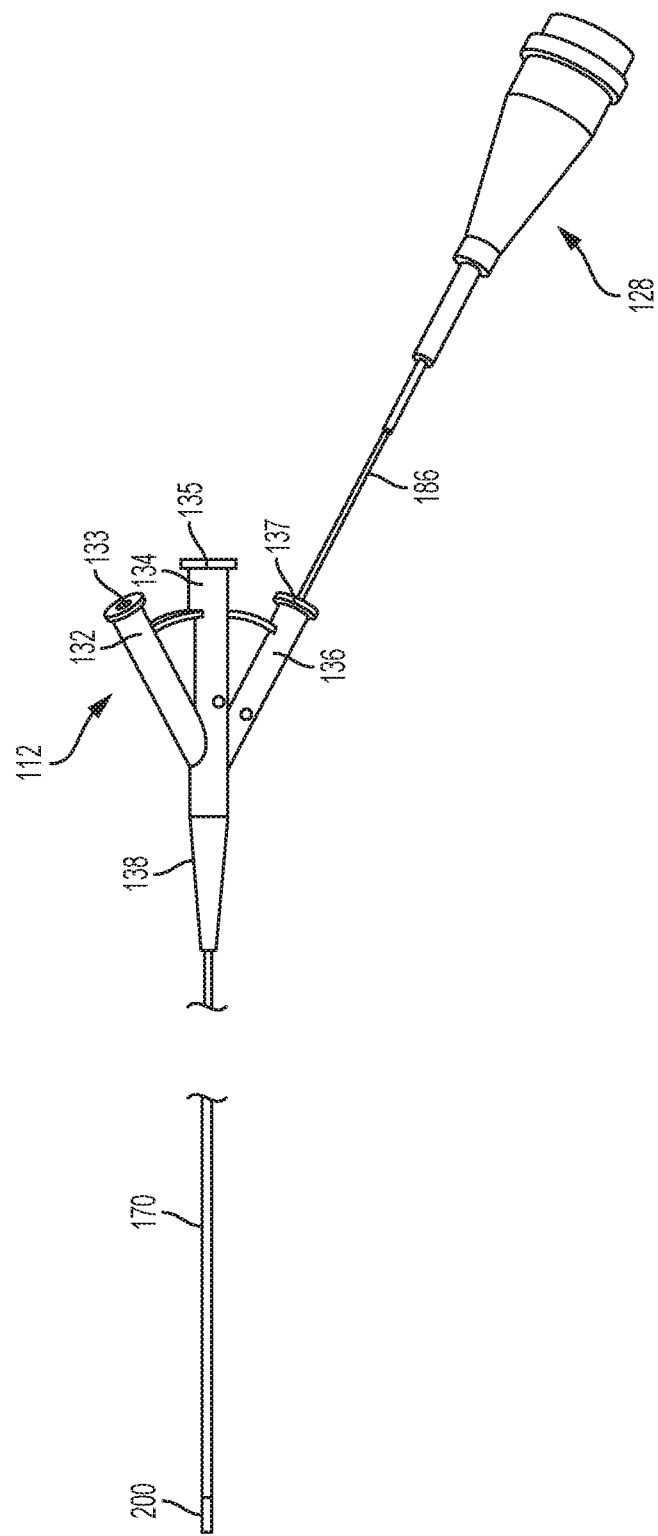
FIG. 1A is an elevation view of one variation of an electrically-induced angioplasty catheter sheath system of FIG. 1.

Referring to FIG. 1A, the electrically-induced angioplasty catheter sheath system 100 may comprise a catheter 170 and one or more stationary or slidable electrode assemblies 200 coupled to an electrode catheter 186. The catheter 170 comprises a shaft or sheath having a lumen therethrough, a proximal hub 112 coupled to the proximal end of the shaft.

The electrode catheter 186, which may include the one or more electrode assemblies 200 at its distal end and a high-voltage connector 128 at its proximal end. Upon inserting the electrode catheter 124 into the balloon catheter, the electrode assemblies 120 will be disposed within the distal portion of the shaft of the catheter 170.

The proximal hub 112 may be a bifurcate design or a trifurcate design. FIG. 1A illustrates the proximal hub 112 having a trifurcate design, which includes a central shaft 134, a first side shaft 132 and a second side shaft 136. The first and second side shafts are attached to either side of the central shaft 134. The central shaft 134 may have a proximal opening 135 that is connected to an inner lumen (not shown) of the proximal hub 112. The inner lumen extends through the length of the central shaft 134 and terminates at a distal opening (not shown) of the proximal hub 112. The proximal hub 112 may optionally comprises a strain relief portion 138, and if so, the inner lumen will pass through and exit the strain relief 138 member, thereby allowing the proximal hub 112 to be in fluid communication with the catheter 108.

The inner lumen may also be in communication and/or continuous with the guide wire lumen (not shown) of the catheter 170. The first side shaft 132 may have an opening 133 that is coupled to the inner lumen or a separate lumen within the proximal hub 112, and the second side shaft 136 may have an opening 137 that is coupled to the inner lumen or a separate lumen within the proximal hub 112. For example, the central shaft 134, the first side shaft 132 and the second side shaft 136 may all be coupled with and in fluid communication with the same inner lumen of the proximal hub 112, or the central shaft 134, the first side shaft 132 and the second side shaft 136 may be coupled with and in fluid communication with three separate lumens within the proximal hub 112. That is, the first side shaft 132 may serve as an input port for a fluid, which may include saline and/or imaging contrast agent, for delivery to the location of the electrode assemblies 200. If so, the fluid will travel through a lumen in the proximal hub 112 and a corresponding lumen within the catheter 108 which opens into the distal portion of the catheter 170. The central shaft 134 may serve as a guidewire port for guidewire to be inserted through the inner lumen of the proximal hub 112, and a corresponding guidewire lumen that travels through and beyond the catheter 104 and the balloon 116. The second side shaft 136 may serve as a port the electrode catheter 124. If so, the electrode catheter 186 will enter the opening 137 and travel through a separate lumen that corresponds with a separate lumen in the catheter 108 at least to and potentially beyond its distal portion. The inner lumens may each have a wider proximal region and a narrower distal region, which may act as a stop for the devices inserted into the shafts. In some variations, the proximal hub 112 may be made of injection molded polycarbonate.

Figure 1B:
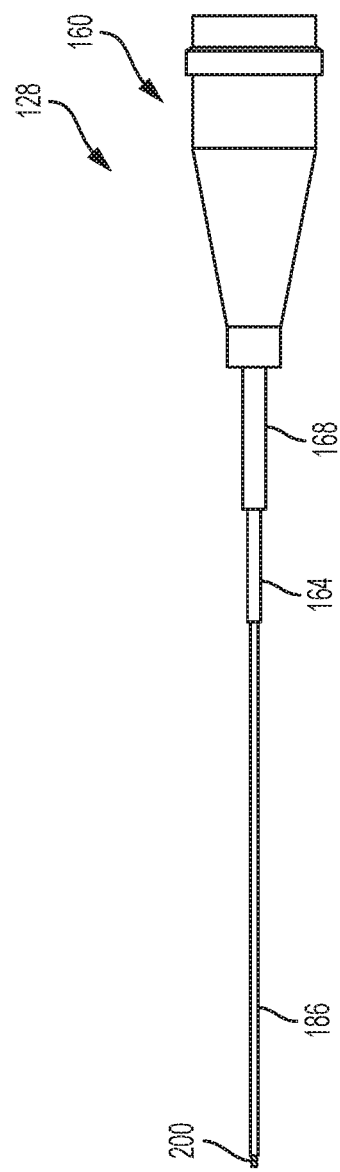
FIG. 1B is an elevation view of one variation of an electrode catheter that can be inserted into and slidable within an electrically-induced pressure wave emitting catheter sheath system of FIG. 1A.

Referring to FIG. 1B, the high-voltage connector 128, which may be inserted through at least one of the central shaft 134, the first side shaft 132 and the second side shaft 136 of the proximal hub 112, may be configured to connect the electrode assemblies 120 to a high voltage pulse generator (not shown). The high voltage connector 128 may also include a cable 250 that may be enclosed in a jacket. The high voltage connector 128 may also include a first shaft region 168 and a second shaft region 164 that is narrower than the first shaft region 168, and both the first shaft region 168 and the second shaft region 164 surround the cable 250, which connects to the proximal hub 112. The first shaft region 168 may have a diameter that is greater than the diameter of the narrower portion of an inner lumen 133, 135, 137 of the proximal hub 112, but smaller than the diameter of the wider portion of the inner lumen. The second shaft region 164 distal to the first shaft region 168 may be configured for strain relief.

The cable 250 may comprise one or more wires that are enclosed along the length of the electrode catheter 186 are coupled to corresponding electrode assemblies 200. The proximal end of the cable 250 extends to and connects with the high voltage connector 160, and the distal end of the cable 250 extends to and connects with the electrode assemblies 200. For example, the cable 250 may provide connections for both the high voltage pulse(s) and the return path between the voltage pulse generator and the electrode assemblies 200. In some variations, the cable 250 may provide one or more high voltage supply connections to the electrode assemblies 200, with one or more return connections. For example, the cable may provide for a single high voltage supply connection and a single return connection to the electrode assemblies. Alternatively, the cable 250 may provide for a plurality of high voltage supply connections (for example, four) and one or more return connections to the electrode assemblies 200.

The high voltage connector 160 electrically connects and couples to a high voltage pulse generator, thereby providing to the electrode assemblies 200 at the distal end of the catheter 170. Pins within the high-voltage connector 160 may connect each of the wires from the electrode assemblies 200 to the appropriate channel on a high voltage pulse generator 130. The cable 250 may be bonded to the high-voltage connector 160 and/or the proximal hub 112. As discussed above, the cable 250 may extend from a lumen of the proximal hub 112 and connect to the high-voltage connector 160. Pins within the high-voltage connector 160 may connect each of the wires from the electrode assemblies 120 to the appropriate channel on a high voltage pulse generator.

Referring to FIG. 1C, there is depicted an example of a variation of an electrode assembly 200 for inclusion in an electrode catheter 170. The electrode assembly 200 may comprise a first electrode 201, an insulating layer 202 overlaying the first electrode, and a second electrode 203. The first electrode 201 may be a positive electrode and the second electrode 203 may be a negative electrode (or vice versa). The elongate member 220, which is similar to one of the shaft regions 164, 168 of FIG. 1B (including the cable 250), may have a guide wire lumen extending along a length of its longitudinal axis. The insulating layer 202 may be made of any material with a high breakdown voltage, such as Kapton, ceramic, polyimide or Teflon. The insulating layer 202 may have an opening 207 that is aligned over the first electrode 201. Although the second electrode 203 is depicted as having a ring shape, it should be understood that the second electrode 203 may be a planar sheet or layer. The second electrode 203 may have a central opening 208 and stacked over the insulating layer 202 such that the second electrode opening 208 is coaxially aligned with the insulating layer opening 207. The openings 207, 208 may be in the shape of a circle, oval, ellipse, rectangular, or any desired shape.

Layering and stacking the first electrode 201, insulating layer 202 and second electrode 203 as depicted in FIG. 1C maintains a substantially flat profile against the outer surface of the elongate member 202, while maintaining a coaxial electrode configuration for arc production. That is, such a configuration may be electrically similar to a traditional coaxial lithotripsy assembly having an inner electrode and an outer electrode surrounding the inner electrode, but without substantially increasing the crossing profile of the elongate member. A more detailed description of this variation of the electrode assemblies is included in U.S. Pat. No. 8,888,788 which is hereby incorporated herein by reference in its entirety for all that it teaches and for all purposes.

Figure 1D:
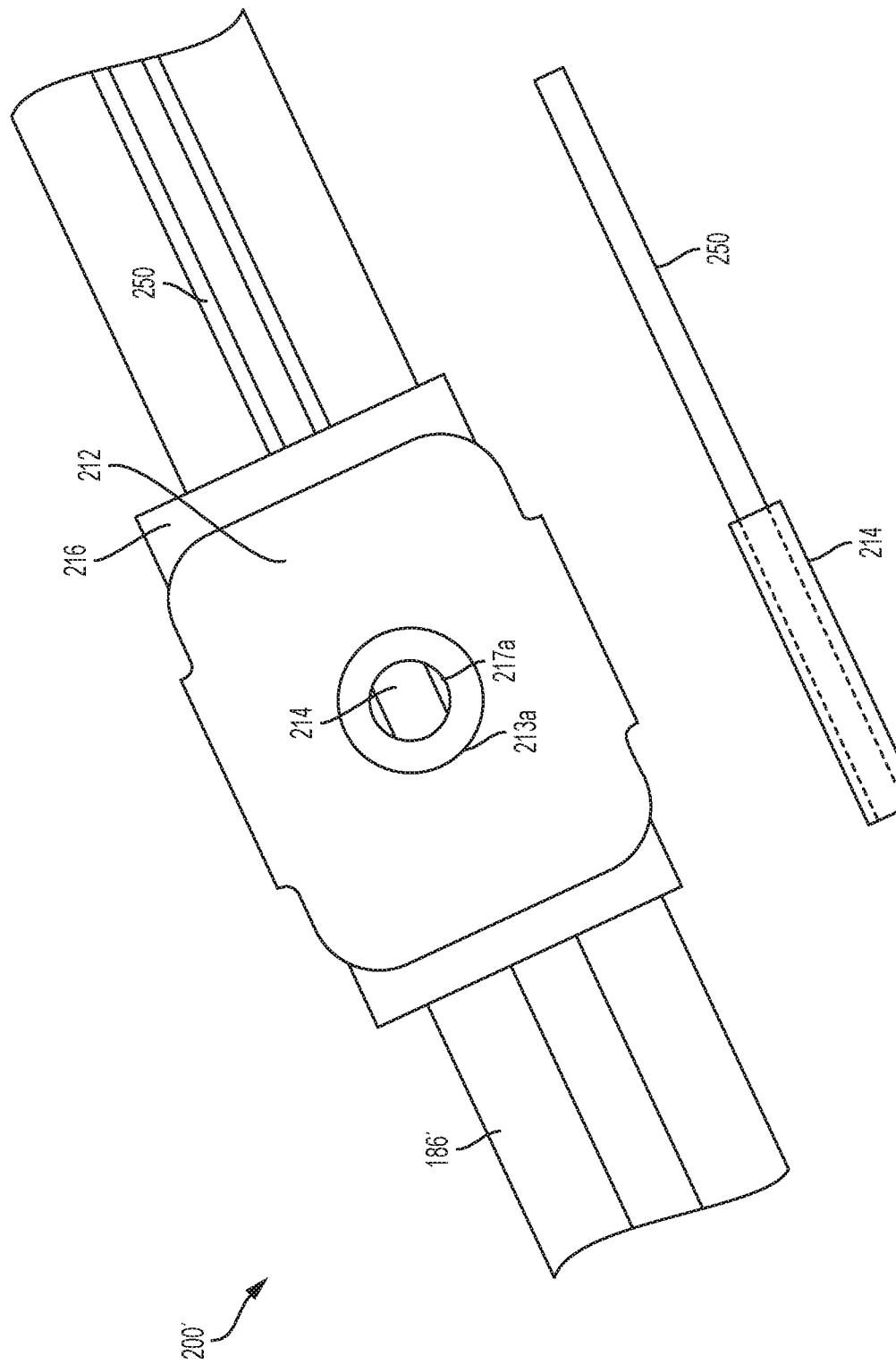
FIG. 1D is a top view of another variation of an electrode assembly for inclusion in an electrode catheter that can be in the electrically-induced pressure wave emitting catheter sheath system of FIGS. 1, 1A and 1B.

Referring to FIG. 1D, there is depicted an alternative version of an electrode assembly 200' coupled to the electrode catheter 186'. The electrode assembly 200' depicted in this figure is a low-profile electrode configuration. The electrode assembly 200' may include a first inner electrode 214, an inner insulating layer or sheath 216 disposed over the first inner electrode 214 and circumferentially wrapped around an elongate member 186' (for example, a catheter with a guidewire lumen), and an outer electrode sheath 212 disposed over the inner insulating sheath 216. The inner insulating sheath 216 of the electrode assembly 200' may have a first opening 217*a* that is coaxially aligned over the first inner electrode 214, and the outer electrode sheath 212 may have a first opening 213*a* that is coaxially aligned over the first opening 217*a* of the inner insulating sheath. The electrode assembly 200' may also include a second inner electrode that is circumferentially opposite (or otherwise circumferentially and/or axially displaced from) the first inner electrode (and therefore not depicted in the view of FIG. 1D). The inner insulating sheath may have a second opening that is coaxially aligned over the second inner electrode, and the outer electrode sheath may have a second opening that is coaxially aligned over the second opening of the inner insulating sheath. A high voltage source can supply a high voltage pulse across the inner electrodes to generate two shock waves on either side of the assembly. More specifically, an electrical arc will be created across one inner electrode to the outer electrode and across the outer electrode and the remaining inner electrode on the opposite side of the electrode assembly 200'. A more detailed description of this low-profile variation of the electrode assemblies is included in U.S. Publication No. 20150039002 which is hereby incorporated herein by reference in its entirety for all that it teaches and for all purposes.

Figure 1E:
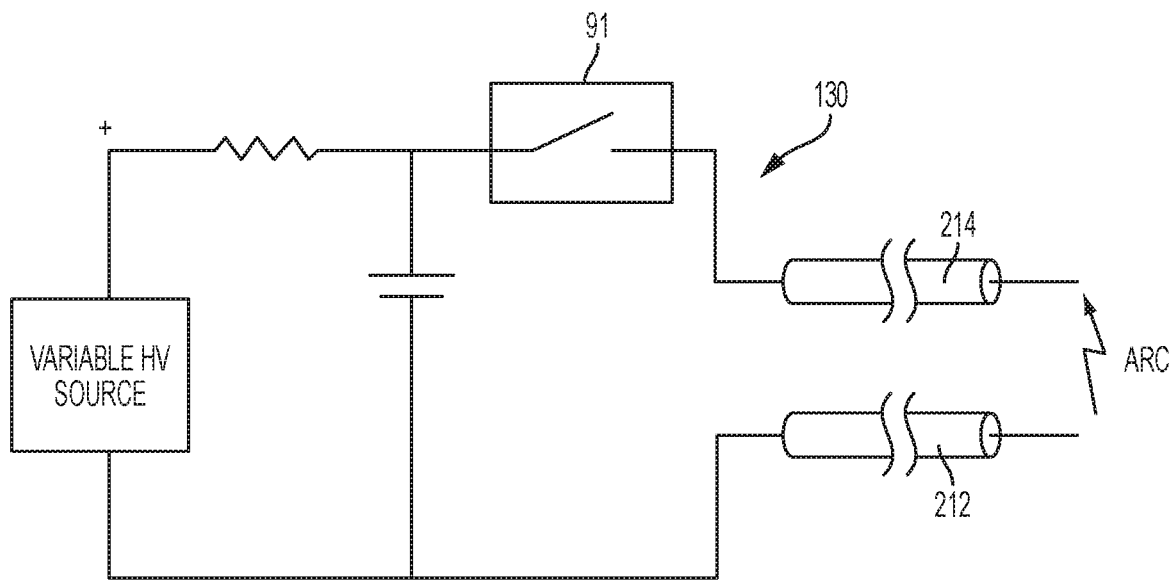
FIG. 1E is a schematic of a high voltage pulse generator connected to the electrodes, which create the arc.
Figure 1F:
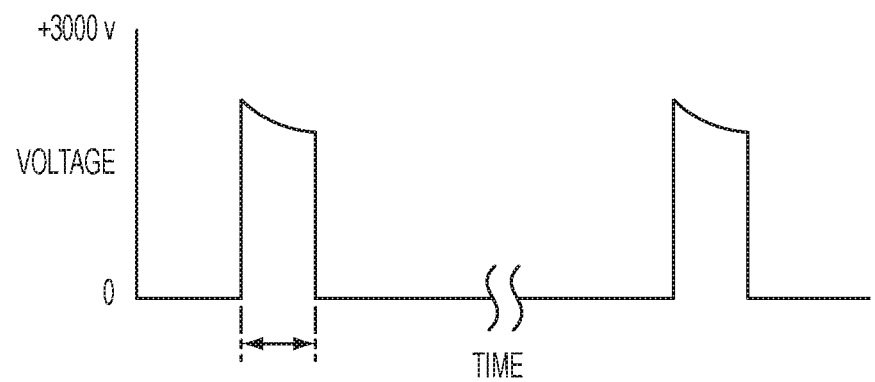
FIG. 1F depicts voltage pulses that may be produced by the high voltage pulse generator of FIG. 1E.

Referring to FIG. 1E, there is depicted a schematic of the high voltage pulse generator 130. And FIG. 1F shows a resulting waveform produced by the generator 130. The voltage needed will depend on the gap between the electrodes and is generally 100 to 3000 volts. A high voltage switch 91 can be set to control the duration of the pulse. The pulse duration will depend on the surface area of the positive and negative electrodes 212, 214 and needs to be sufficient to generate a gas bubble at the surface of the electrode causing a plasma arc of electric current to jump the bubble and create a rapidly expanding and collapsing bubble, which creates the mechanical pressure wave in the sheath. Such pressure waves can be as short as a few microseconds. Since both the rapid expansion and the collapse create pressure waves, the pulse duration can be adjusted to favor one over the other. A large steam bubble will generate a stronger pressure wave than a small one. However, more power is needed in the system to generate this large steam bubble. Traditional lithotripters try to generate a large steam bubble to maximize the collapsing bubble's pressure wave. By adjusting the pulse width to a narrow pulse less than two microseconds or even less than one microsecond a rapidly expanding steam bubble and pressure wave can be generated while at the same time the final size of the steam bubble can be minimized. The short pulse width also reduces the amount of heat in the balloon to improve tissue safety.

FIG. 1E only depicts one electrode assembly comprising positive and negative electrodes 212, 214, and FIG. 1E only depicts one variable high voltage source coupled to the electrode assembly. But it shall be understood that multiple electrode assemblies may be coupled to the high voltage pulse generator 130. In the event that multiple electrode assemblies are coupled to the same high voltage pulse generator 130, the electrode assemblies and the high voltage pulse generator 130 may be configured such that the high voltage pulse generator 130 provides power to the electrode assemblies so that the electrode assemblies produce and/or emits electrical pulses simultaneously, serially or according to another firing sequence. Additionally, it shall also be understood that each multiple electrode assembly may be coupled to an independent high voltage pulse generator 130 such that each electrode assembly is independently controlled, and each electrode assembly produces and/or emits separate electrical pulses. A more detailed description of how the high voltage pulse generator and/or the electrode assemblies are controlled is included in U.S. Pat. Nos. 8,728,091 and 8,747,416 and 9,011,463 and 9,138,249 which are hereby incorporated herein by reference in its entirety for all that they teach and for all purposes.

As discussed above, the electrode catheter may include a coaxial electrode assembly configuration, such as that depicted in FIG. 1C at the distal end of the electrode catheter. Alternatively, the electrode catheter may include a low-profiled configured electrode assembly 200', such as that depicted in FIG. 1E. It may also be advantageous to include the low-profiled configured electrode assembly 200' when incorporating multiple electrode assemblies 200' to the electrode catheter. An example of such an electrode catheter is depicted in FIG. 1G.

Figure 1G:
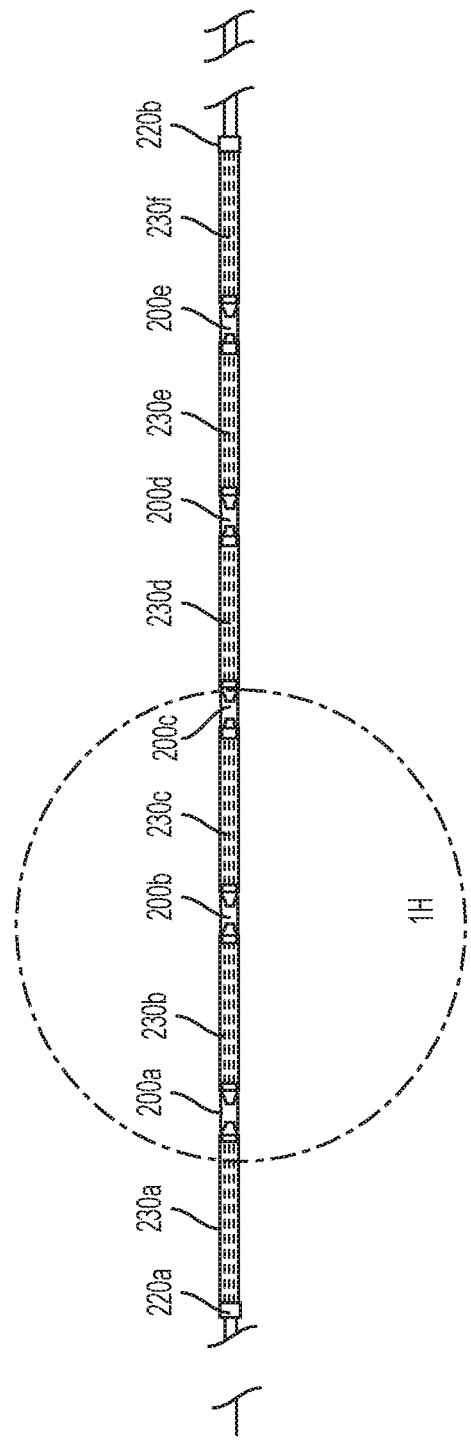
FIG. 1G is an elevation view of a version of an electrode catheter that can be included within the electrically-induced pressure wave emitting catheter sheath system of FIGS. 1, 1A and 1B.
Figure 1H:
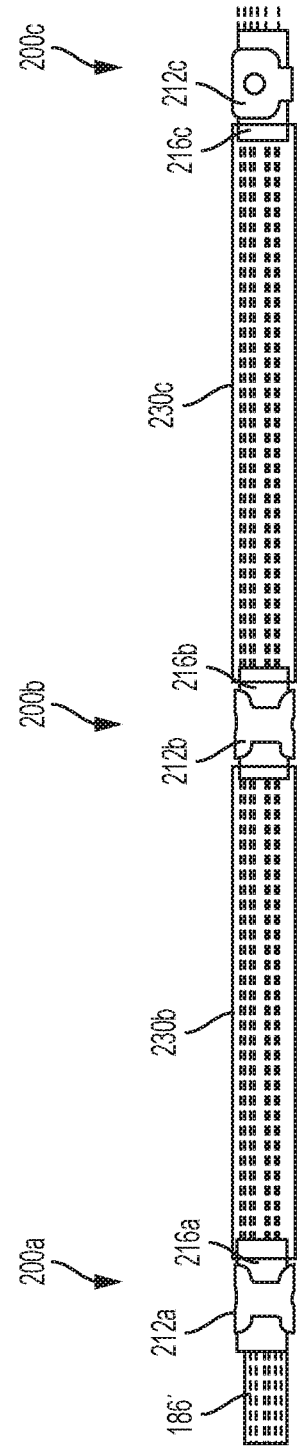
FIG. 1H is an elevation view of an enlarged portion the electrode catheter depicted in FIG. 1G.

Referring to FIGS. 1G and 1H, there is depicted an elongated member 186" and a series of electrode assemblies separated by a series of tubular sleeves disposes over the elongated member. Specifically, a first electrode assembly 200*a*, a second electrode assembly 200*b*, a third electrode assembly 200*c*, a fourth electrode assembly 200*d*, and a fifth electrode assembly 200*e*, are separated by a series of tubular sleeves 230*b*, 230*c*, 230*d* and 230*e*. The electrode catheter may also include two radiopaque markers 220*a* and 220*b* beyond the axial position of the electrode assemblies. If so, one or more of the tubular sleeves 230*a*, 230*f* may be placed between a radiopaque marker 220*a*, 220*b* and an adjacent or neighboring electrode assembly neighboring electrode assembly 200*a*, 200*f*. The device may include any suitable number of electrode assemblies, marker bands, and tubular sleeves. In some variations, the tubular sleeve having an end that is adjacent to either electrode assemblies or the radiopaque markers may be tapered or flared to accommodate an electrode assembly's or the radiopaque marker's outer diameter that is smaller or larger, respectively, than the outer diameter of a neighboring electrode assembly or the radiopaque marker. For example, if a tubular sleeve has a tapering outer profile, one sleeve end may overlap an inner electrode sheath of an electrode assembly, and the other sleeve end may overlap the radiopaque marker. Similarly, if a tubular sleeve has a tapering outer profile, one sleeve end may overlap an inner electrode sheath of an electrode assembly, and the other sleeve end may overlap an inner electrode sheath of another electrode assembly. The radiopaque marker's outer diameter may be less than the diameter of an outer electrode sheath, and a tubular sleeve may have an outer profile that tapers from the electrode assembly to the radiopaque marker. In other variations, the tubular sleeve maintains a consistent diameter throughout its length regardless of whether it is placed between two electrode assemblies or between an electrode assembly and a marker band. A more detailed description of the low-profile version is included in U.S. Publication No. 2015-0039002 A1 which is hereby incorporated herein by reference in its entirety for all that it teaches and for all purposes.

Referring to FIG. 1I, there is depicted a portion of the electrode catheter illustrated in FIG. 1G, including a modification thereto. Specifically, the portion illustrated in FIG. 1I includes the portion of the electrode catheter between the electrode assembly 200e and the radiopaque marker 220b. As shown in FIG. 1G, the electrode assembly 200e includes an insulating sheath 212e and an outer electrode sheath 216e. The electrode catheter also includes a tubular sleeve 230f axially disposed between the electrode assembly 200e and the radiopaque marker 220b. The diameter of the electrode assembly 200e is substantially the same or equal to the diameter of the tubular sleeve 230f. The electrode catheter also includes a shield or deflector 604 that is capable of deflecting the pressure wave(s) toward the guidewire and/or guidewire lumen of the electrode catheter 200e in order to vibrate the guidewire passing therethrough.

It may also be desirable to excite and vibrate the guidewire to increase the guidewire's ability to pierce and cross the occlusion. Accordingly, the present disclosure also contemplates directing the pressure waves caused by creating an electrical spark across the electrodes in the liquid medium to propagate pressure waves toward the guidewire lumen and/or guidewire such that the pressure waves excite and vibrate the guidewire. One end 606 of the deflector 604 depicted in FIG. 1I is coupled to the tubular sheath 230f, and the other end of the deflector 602 is disposed such that it is radially offset but axially aligned with at least a portion of the electrode assembly 200e. Upon creation of the pressure wave, the deflector deflects the pressure wave(s) toward the guidewire and/or guidewire lumen of the electrode catheter 200e in order to vibrate the guidewire passing therethrough. For example, the distal portion 602 of the deflector 604 is tapered such that the pressure wave will reflect off the deflector 604 and move radially inward away from the electrode assembly 200e. Although FIG. 1I depicts only a portion of the deflector 604 being axially aligned with a portion of the electrode assembly 200e, the present disclosure contemplates disposing the deflector 604 in a position with respect to the electrode assembly 200e such that it is axially aligned with the entire electrode assembly 200e. Additionally, although FIG. 1I depicts the deflector 604 being coupled to one tubular sheath 230f, the deflector may be coupled to another tubular sheath, namely the tubular sheath 200e, and/or the deflector may be coupled to both tubular sheaths 230e, 230f such that the deflector spans axially over the electrode assembly 200e.

Figure 2B:
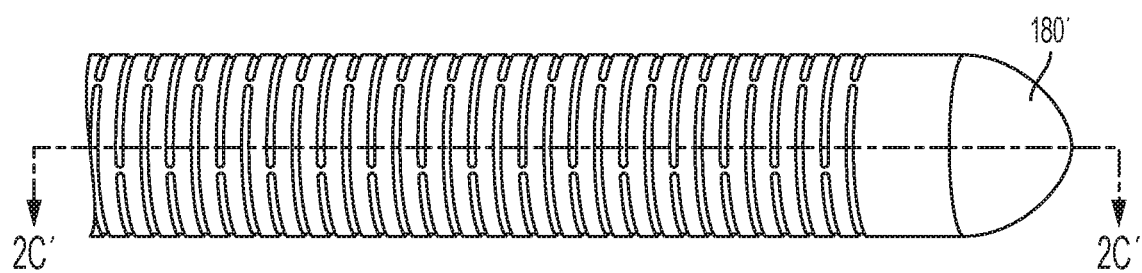
FIG. 2B is an elevation view of an embodiment of the distal portion of the electrically-induced pressure wave emitting catheter, according to one embodiment of the present disclosure.
Figure 2C:
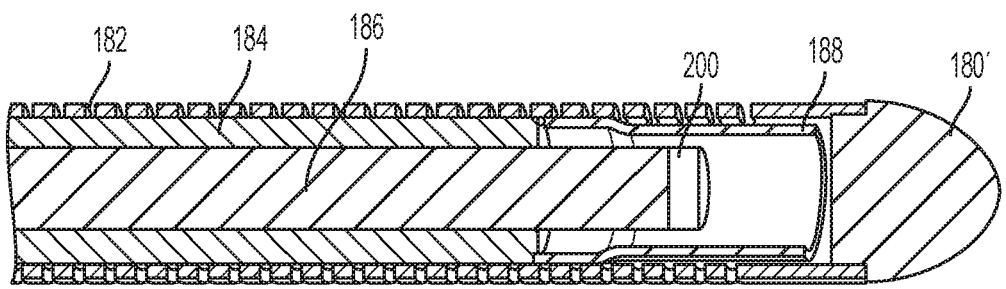
FIG. 2C is a cross-sectional view (along line 2C-2C in FIG. 2B) of the distal portion of the electrically-induced pressure wave emitting catheter.

Referring to FIGS. 2A, 2B and 2C, the catheter 170 of the present disclosure may include an outer sheath 182, an optional inner sheath 184, an electrode catheter 186 having one or more electrode assemblies 200, and a tip 180. The outer sheath 182, inner sheath 184, and the electrode catheter 186 generally span the length of the catheter 170, and each have a proximal end and a distal end. The inner sheath 184, if included, is disposed concentrically and/or radially within the outer sheath 182, and the electrode catheter 186 is disposed concentrically and/or radially within the outer sheath 182 and/or inner sheath 184. The electrode catheter 186 can be configured as shows in FIG. 1B, 1C, 1D, 1G, 1H or 1I.

As depicted in FIG. 2C, at the distal end 126 of the catheter 170, the distal end of the outer sheath 182 is directly coupled to the tip 180. The inner sheath 184 and the electrode catheter 186 are not directly coupled to the tip 180. Rather, the inner sheath 184 and the electrode catheter 186 are disposed proximate the tip 180, thereby forming a cavity among the outer sheath 182, the inner sheath 184, the electrode catheter 186, and the tip 180.

The inner sheath 184 (and/or outer sheath 182), which is constructed of a biocompatible polymer has one or more lumens 190, which are used to deliver a liquid medium to the cavity, thereby partially or completely filling the cavity with the liquid medium. The liquid medium is introduced to the catheter 170 through one or more liquid medium ports (not shown) in fluid communication with the one or more lumens 190 within the inner sheath 184 and disposed about the outer sheath 182. The liquid medium ports may also serve as a means for removing the liquid medium from the catheter 170. The liquid medium is configured to absorb electrical (or plasma) energy, produce pressure waves and create cavitation bubbles that produce additional resultant pressure waves that are transmitted to the tip 180 and/or the outer sheath 182 to disrupt a vascular obstruction. The liquid medium can include contrast medium, including for example, iodine-containing contrast medium or gadolinium contrast medium, as well as contrast solutions comprising dye(s) and/or particle(s). Additionally, any liquid medium can be used, as long as the liquid medium is coupled with an electrical source, such as one or more electrode assemblies coupled to the one or more cables. The electrode assemblies produce an electrical (or plasma) arch such that the liquid absorbs the electrical energy, produces pressure waves and creates cavitation bubbles the produce additional resultant pressure waves. In some cases, the liquid medium can be contrast medium (for example, iodine-containing contrast medium or gadolinium contrast medium) and/or the liquid medium can be a contrast solution comprising a biocompatible fluid (for example, saline) in which a contrast dye(s) or particle(s) have been mixed at various concentrations.

As mentioned above, one or more cables 250 are disposed within the electrode catheter 186 extending from a proximal portion of the electrode catheter 186 to the electrode assembly 200, which is depicted at the distal end of the electrode catheter 186 in FIG. 2C. The proximal end of the one or more cables 250 is coupled to the high voltage pulse generator 130. The distal end(s) of the one or more electrode assemblies 200 are proximate, at, or distal the distal end of the inner sheath 184 such that the electrode assembly 200 is disposed within the cavity of the catheter 170. Because the electrode assembly 200 is disposed within the cavity, which includes the liquid medium, the electrode assembly 200 is in direct contact with the liquid medium, such that when electrical energy is produced by the electrode assembly, the liquid medium absorbs the electrical energy, which in turn produces pressure waves and generates cavitation bubbles that produce additional pressure waves.

To treat a subject having a vascular occlusion, the tip 180 of the catheter 170 is positioned adjacent to the vascular occlusion. When the high voltage pulse generator 130 is activated, pulses of electrical energy travel along one or more cables 250 until the electrical energy reaches the electrode assembly 200 (or additional electrode assemblies), which is creates a pulsed arc across the electrodes. As the liquid medium absorbs the electrical energy, pressure waves are produced. Additionally, the liquid medium rapidly expands and contracts, creating vapor bubbles that propagate pressure waves through the liquid medium. The energy produced by the pressure waves is captured within the cavity and converted to mechanical energy via moving the tip 180 and/or transferred to the vascular occlusion through the tip 180. The transfer of the energy produced by the pressure waves to the vascular occlusion is sufficient to disrupt vascular obstructions, particularly the calcified and/or fibrous (for example, calcium deposits) portions of a total occlusion. It is desirable for the mechanical energy created at the tip 180 by the pressure waves to be transferred to the occlusion. Accordingly, when the energy produced by the pressure waves is captured within the cavity, it is desirable for the forces generated by the pressure waves to propagate longitudinally, including in a forward (such as, parallel with the vessel) direction, thereby increasing the tip's ability to disrupt, destroy and/or penetrate the vascular obstructions. That is, as the pressure waves are produced, the tip 180 of the catheter rapidly moves (translates) forwards and backwards towards and away from, respectively, the occlusion. Pressure waves produced in this manner can also be used to increase vessel compliance prior to performing another procedure, such as a traditional balloon angioplasty or drug eluting balloon treatment.

In order to facilitate the direction in which the forces that are produced by the pressure waves translate into the movement of the tip 180 in a forward/backward longitudinal direction, the outer sheath 182 is not only flexible, but the outer sheath 182 also has the ability to expand and contract in a longitudinal direction. One example of such an outer sheath 182 includes a slotted or laser-cut hypotube constructed of a biocompatible material, such as stainless steel, or a biocompatible polymer. The hypotube has spring-like characteristics, which allow it to expand and contract in a longitudinal direction. Specifically, the slotted or laser cut pattern in the hypotube allows it to expand and contract. Another example of the outer sheath 182 may include of one or more spirally wound wires, thereby creating a coiled sheath, which also has the ability to expand and contract in a longitudinal direction.

In order to further facilitate the movement of the tip 180 in a longitudinal direction, it may be desirable to include a shield 188 disposed axially between the distal end of the inner sheath 184 and the proximal end of the tip 180, and disposed radially between the electrode assembly 200 and the outer sheath 182. As illustrated in FIG. 2C, the shield 188, which is depicted as a generally cylindrical tube, may increase the pressure waves' resistance in the radial direction, thereby reducing the ability of the pressure waves to travel radially towards the outer sheath 182 and may concentrate the energy produced by the pressure waves in the longitudinal (axial) direction. The configuration of the cylindrically-shaped shield 188 may allow for a reduced resistance in the longitudinal direction, in comparison to the radial direction, thereby potentially increasing the energy produced by the pressure waves in the longitudinal direction and increasing the tip's ability to translate in a forward/backward direction. The cylindrically-shaped shield 188 may also be configured such that its diameter is greater at its proximal end in comparison to its distal end, thereby potentially concentrating the pressure waves towards the center of the tip 180. Or the cylindrically-shaped shield 188 may be configured such that its diameter is less its proximal end in comparison to its distal end, thereby potentially concentrating the pressure waves towards the center of the tip 180.

The tip 180 illustrated in FIGS. 2B & 2C has a closed configuration. However, the present disclosure contemplates that the tip can also have an open configuration. Additionally, the tip 180 illustrated in FIGS. 2B & 2C is a separate component from the distal end 126 of the electrically-induced pressure wave emitting catheter 170 and is coupled to the distal end 126. However, the present disclosure contemplates that the tip can also be integral with the distal end 126 of the electrically-induced pressure wave emitting catheter 170. The tip 180 illustrated in FIGS. 2B & 2C is generally tapered from a larger diameter to a smaller diameter as the tip progresses distally. Additionally, the shape of the tip 180 shown in FIGS. 2B & 2C is generally conical. Furthermore, the tip 180 has a completely solid configuration, but it may be also be partially solid. It is desirable for the tip to be constructed of a biocompatible material, such as stainless steel or a biopolymer.

Similar to the tip 180 illustrated in FIGS. 2B & 2C, the tip 180' in FIGS. 2B' & 2C' has a completely solid configuration, but the tip 180' in FIGS. 2B' & 2C' may alternatively have a partially solid configuration. Unlike the tip 180 illustrated in FIGS. 2B & 2C, the tip 180' in FIGS. 2B' & 2C' may have a generally convex, spherical shape. Although the present disclosure only depicts a generally conically-shaped tip 180 in FIGS. 2B & 2C and a generally spherically-shaped tip 180' in FIGS. 2B' & 2C', the tip may have alternative shapes, such as a flat shape, concave shape, triangular shape, a pyramid shape, chisel, etc.

Figure 3:
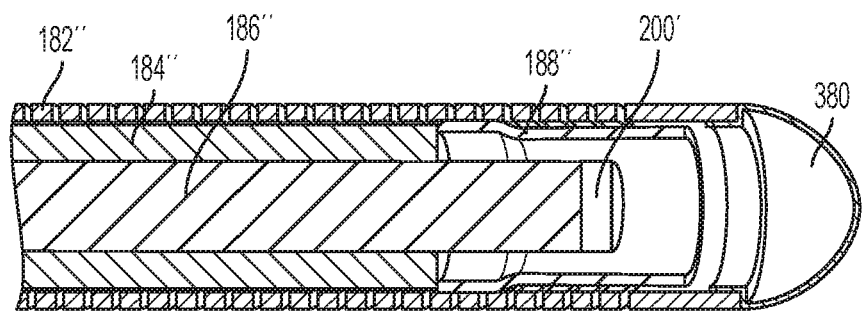
FIG. 3 is a cross-sectional view of the distal portion of the electrically-induced pressure wave emitting catheter, according to one embodiment of the present disclosure.

Referring to FIG. 3, there is depicted an alternative embodiment of the catheter of the present disclosure. Similar to the tip 180' in FIGS. 2B' & 2C', the tip 380 in FIG. 3 has a generally spherical shaped. However, unlike the tip 180' in FIGS. 2B' & 2C', which has a solid configuration, the tip 380 in FIG. 3 has a hollow or shell-type configuration. Also, the tip 280 in this embodiment, as well as the other embodiments, may be press fit and/or welded to the outer sheath 182".

Figure 4:
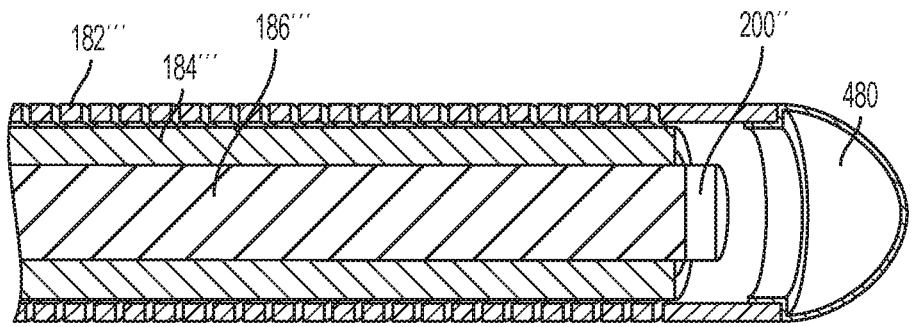
FIG. 4 is a cross-sectional view of the distal portion of the electrically-induced pressure wave emitting catheter, according to one embodiment of the present disclosure.

The embodiments of the catheter depicted in FIGS. 2B & 2C and FIGS. 2B' & 2C' and FIG. 3 include a shield 188. However, it may not be necessary to include a shield within the catheter. For example, FIG. 4 illustrates an embodiment of the catheter 170 in which the shield is omitted from the distal tip of the catheter. As depicted in this figure, in the event that a shield is omitted, it may be desirable for the outer sheath 182''' to include a solid portion between the distal end of the inner sheath 184''' and the proximal end of the tip 480 in order to create a non-porous cavity.

Figure 5:
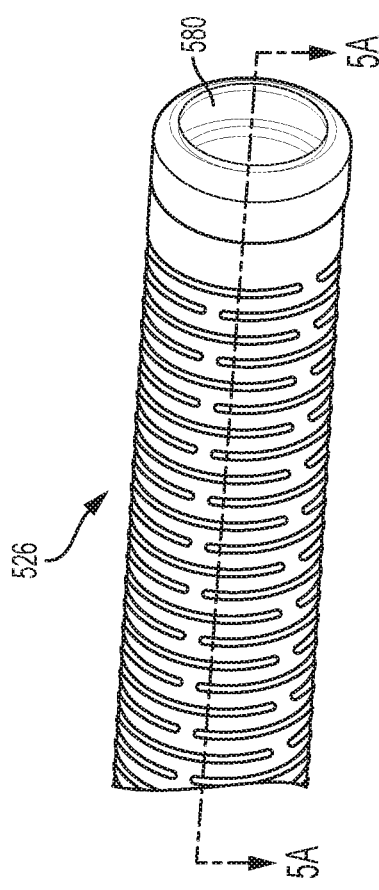
FIG. 5 is a perspective view of an embodiment of the distal portion of the electrically-induced pressure wave emitting catheter, according to one embodiment of the present disclosure.
Figure 5A:
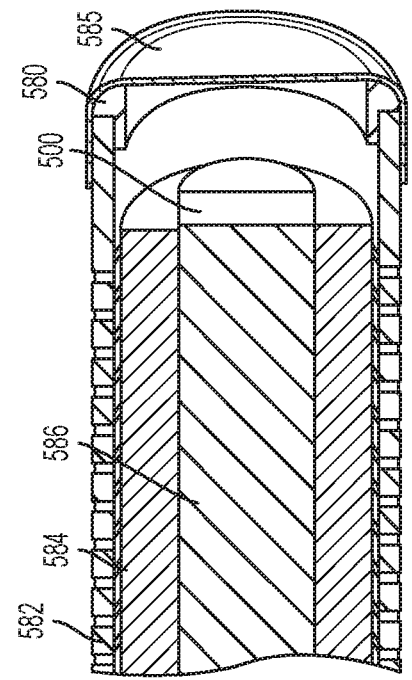
FIG. 5A is a cross-sectional view (along line 5A-5A in FIG. 5) of the distal portion of the electrically-induced pressure wave emitting catheter, according to one embodiment of the present disclosure.
Figure 5A:
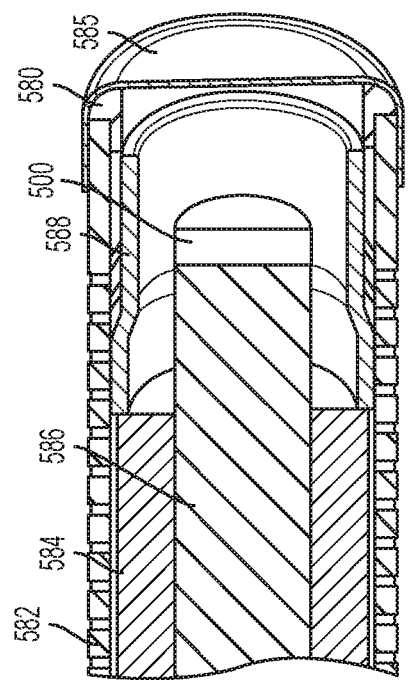

Referring to FIGS. 5, 5A and 5A', the distal end 526 of the electrically-induced pressure wave emitting catheter may include a tip 580 that comprises a non-metallic component in lieu of a metallic (for example, stainless steel) solid or hollow construction. Referring to FIG. 5A, the catheter includes an outer sheath 582, an optional inner sheath 584 disposed concentrically and/or radially within the outer sheath 582, and an electrode catheter 586 having one or more electrode assemblies 500 disposed concentrically and/or radially within the inner sheath 584 and/or outer sheath 586. The distal end of the outer sheath 582 is directly coupled (via a press fit and/or a weld) to the tip 580. The inner sheath 584 and the electrode catheter 586 are not directly coupled to the tip 580. Rather, the inner sheath 584 and the electrode catheter 586, particularly the one or more electrode assemblies 500, are disposed proximate the tip 580, thereby forming a cavity among the outer sheath 582, the inner sheath 584, electrode catheter 586, particularly the one or more electrode assemblies 500, and the tip 580.

Continuing to refer to FIG. 5A, the catheter may include a shield 588 disposed axially between the distal end of the inner sheath 584 and the proximal end of the tip 580, and disposed radially between the one or more electrode assemblies 500 and the outer sheath 582. As illustrated in FIG. 5A, the shield 588, which is depicted as a generally cylindrical tube, increases the pressure waves' resistance in the radial direction, thereby reducing the ability of the pressure waves to travel radially towards the outer sheath 582. The configuration of the cylindrically-shaped shield 588 allows for a reduced resistance in the longitudinal direction, in comparison to the radial direction, thereby increasing the tip's ability to translate in a forward/backward direction. The cylindrically-shaped shield 588 may also be configured such that its diameter is greater (or less) at its proximal end in comparison to its distal end, thereby potentially tapering in either the proximal or distal direction and concentrating the pressure waves towards the center of the tip 580. The shield 588 may also serve to create a sealed cavity at the distal end of the catheter, thereby preventing the leakage of the liquid medium through the outer sheath 582 because a portion of the shield overlaps with a portion of the outer sheath 582 that may be porous. Referring to FIG. 5A', if the shield is omitted, it may be desirable for the outer sheath 582 to include a solid or non-porous sheath portion between the distal end of the inner sheath 584 and the proximal end of the tip 580 in order to create a non-porous cavity.

The inner sheath 584 may also include one or more lumens for passage of liquid medium into the cavity. The distal end(s) of the electrode catheter 586, particularly the one or more electrode assemblies 500 are proximate, at, or distal the distal end of the inner sheath 584. Again, one or more electrode assemblies 500 may be disposed at the distal end of the electrode catheter 586. The one or more electrode assemblies are in direct contact with the liquid medium, such that when electrical energy is produced by the electrode assembly 500, the liquid medium absorbs the electrical energy, thereby producing produces pressure waves and/or cavitation bubbles that produce additional pressure waves.

As depicted in FIGS. 5A and 5A', the tip 580 has a circular construction, thereby creating a collar for the distal end of the outer sheath 582. The tip 580 also includes a flexible membrane 585 at its distal end. For example, the membrane 585 may be constructed of Mylar and be adhesively bonded to the distal end of the tip 580 in an orientation perpendicular to the longitudinal axis. In addition the membrane may be compliant in order to form against and engage the shape of the calcified cap, total occlusion or lesion.

To treat a subject having a vascular occlusion, the distal end of the catheter, particularly the tip 580 is positioned adjacent to the vascular obstruction with the membrane adjacent the vascular occlusion. The liquid medium is delivered to the cavity from the one more lumens within the inner sheath 584 through one or more liquid medium ports or between the outer sheath and the inner sheath or electrode catheter. When the high voltage pulse generator 130 is activated, electrical energy pulses travel along one or more cables until the electrical energy pulses are released by the electrode assemblies 500 on the electrode catheter 586. As the liquid medium absorbs the electrical (plasma) energy, the liquid medium rapidly expands and contracts, creating a pressure wave and/or a vapor bubbles that propagate pressure waves through the liquid medium. The energy produced by the pressure waves is captured within the closed system provided by the cavity and transferred to the vascular occlusion through the flexible membrane 585 of the tip 580. The transfer of the energy produced by the pressure waves to the vascular occlusion is sufficient to disrupt calcium deposits and/or fibrous tissue within the vascular occlusion. The forces generated by the pressure waves can propagate longitudinally in forward (such as, parallel to the vessel). Pressure waves produced in this manner can also be used to increase vessel compliance prior to performing another procedure, such as a traditional balloon angioplasty.

Figure 6:
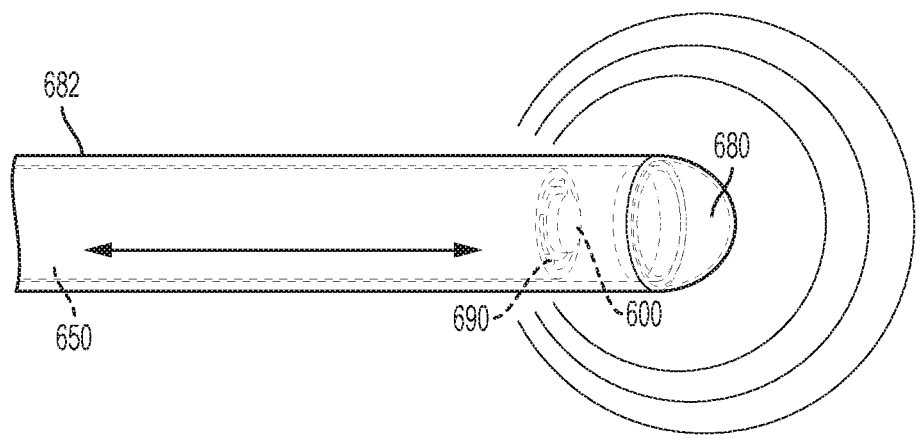
FIG. 6 is a partially transparent elevation view of the distal portion of an electrode catheter disposed at one location within the distal portion of a catheter sheath.
Figure 6A:
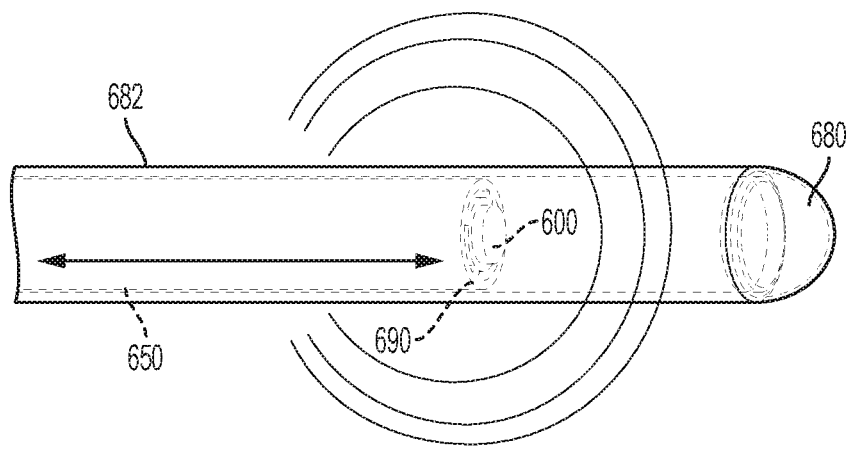
FIG. 6A is a partially transparent elevation view of the distal portion of the electrode catheter disposed at an alternative location within the distal portion of the catheter sheath, in comparison to the position of the electrode catheter in FIG. 6.

The embodiments of the catheters discussed hereinabove with respect to FIGS. 2-5 may be integral electrically-induced pressure wave emitting catheters, such that the electrode catheter is integrated within the design of a single catheter. The present disclosure, however, also encompasses a two-piece catheter system or kit. Referring to FIGS. 6 and 6A, the catheter system may include an electrode catheter 650 and a tubular sheath 682 having a lumen therein and/or therethrough and configured to surround the electrode catheter 650. Depending upon whether the tubular sheath 682 has an open or closed distal end, the tubular sheath 682 may be coupled to a tip 680. An electrode catheter 650, including one or more electrode assemblies 600, can be inserted within the lumen, thereby allowing a clinician to translate the electrode catheter 650 within sheath 682 along the longitudinal axis of the sheath in a forward (distal) and backwards (proximal) direction. For the purposes of this disclosure, the electrode catheter 650 may include one or more one more lumens 690 to deliver the liquid medium from the one or more liquid medium ports. When the high voltage pulse generator system 130 is activated, electrical energy pulses travel along one or more cables until the pulses of electrical energy are released from the electrode assembly 500 if the electrode catheter 600 includes an electrode assembly at the distal end of an electrode catheter similar to that illustrated in FIGS. 1B and 1C and/or from the one or more electrode assemblies 200a, 200b, 200c, 200d and 200e of an electrode catheter similar to that illustrated in FIGS. 1D, 1G, 1H and 1I. That is, either the electrode catheter illustrated in FIGS. 1B and 1C or the electrode catheter illustrated in FIGS. 1D, 1G, 1H and 1I or a combination of both may be used with the two-piece catheter system or kit. As the liquid medium absorbs the electrical energy, the liquid medium rapidly expands and contracts, thereby creating a pressure wave and/or vapor bubbles that propagate pressure waves through the liquid medium. The energy produced by the pressure waves is captured within the closed system provided by the cavity and transferred to the vascular occlusion through the walls of the sheath 682 and/or the tip 680. The transfer of the energy produced by the pressure waves to the vascular occlusion is sufficient to disrupt calcium deposits and/or fibrous tissue within the vascular occlusion. Depending upon the location of the electrode assemblies within lumen of the sheath 682, a smaller or larger cavity is created among the distal end of the electrode catheter 650, the tip 680, and the sheath 682. It may desirable for the distal end of the electrode catheter 650 to be disposed proximal of the tip 680 or translated inside of the outer sheath to create a cavity with which the forces generated by the pressure waves can propagate radially from multiple axial positions along the longitudinal axis of the outer sheath.

Depending upon the location of the electrode assemblies within lumen of the sheath 682, the forces generated by the pressure waves may propagate radially, including in forward (such as, parallel to the vessel), upward (such as, perpendicular to the vessel), and backward (such as, proximally) directions. As depicted in FIG. 6, when the electrode catheter 650 is disposed proximate the tip 680, the pressure waves may propagate radially from the sheath 650 and forward (such as, parallel to the vessel) from the tip. As depicted in FIG. 6A, upon the electrode catheter 650 translating proximally along the longitudinal axis of the lumen within the sheath 682 in comparison to the position of the electrode catheter 650 in FIG. 6, the pressure waves may propagate in a direction radially from the sheath 650, forward (such as, parallel to the vessel), upward (such as, perpendicular to the vessel), and/or backward (such as, proximally). Accordingly, after the tip 680 of the sheath 682 destroys the calcified and/or fibrous tissue within the vascular occlusion, the sheath 682 may penetrate and cross the occlusion, and the electrode catheter 650 can slide in proximal and/or distal direction to destroy additional portions of the occlusion.

Referring to FIG. 6B, the electrode catheter 650' may also include a deflector 692 attached to its distal end via at least one, and possibly a plurality of, support member(s) 698. The purpose of the deflector is to direct the pressure waves generated by the interaction between the liquid medium and the electrical energy produced from one or more electrode assemblies 600' within the liquid medium in a particular direction. In this figure, the deflector 692 is positioned along the longitudinal axis of the electrode catheter 650', but the shape of the deflector 692 is oriented in a radial direction that is perpendicular to longitudinal axis of the electrode catheter 650'. Accordingly, as the pressure waves are produced from the interaction between the liquid medium and the electrical energy produced by the electrode assembly 600', the deflector 692 may direct the pressure waves in a radial direction, such as 360 degrees about the circumference of the electrode catheter 650 and/or sheath 682. The deflector 692 may be constructed of a non-metallic material or a metallic material, such as stainless steel. The deflector 692 may also have a solid or porous construction. Regardless of the construction of the deflector 692, the deflector 692 shall direct the pressure waves in a particular direction that is in an advantageous direction, such as toward the vascular occlusion, which may be on the side of the sheath 682.

Figure 7:
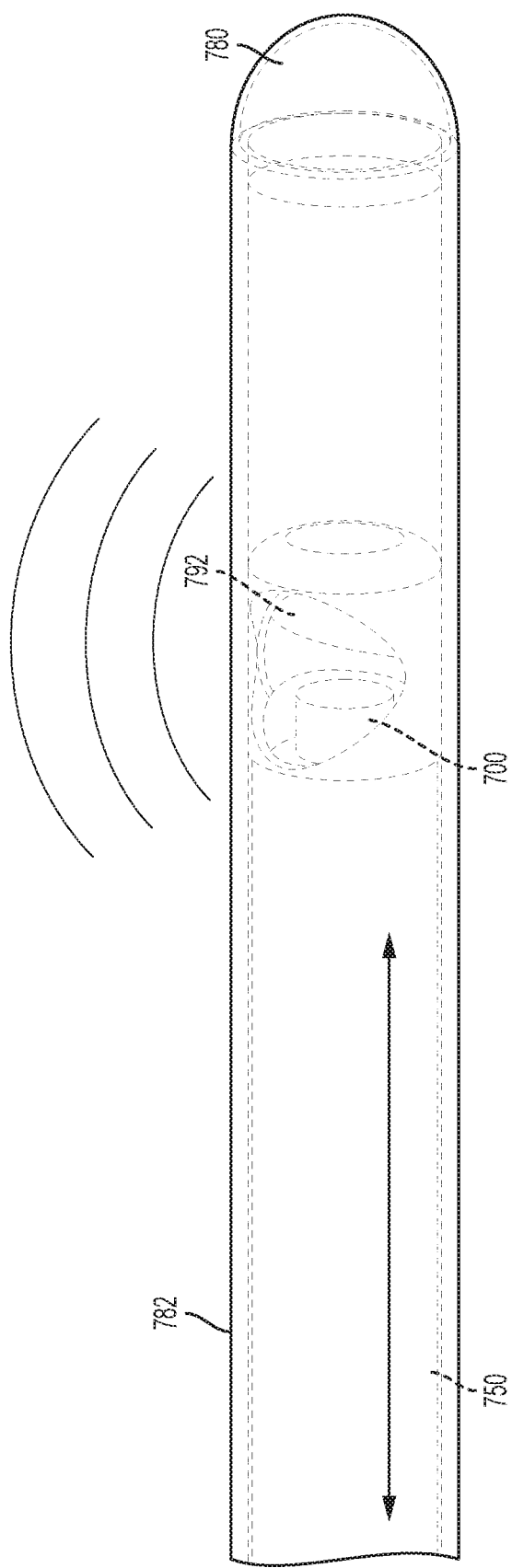
FIG. 7 is a perspective view of an electrode catheter including a shield or deflector as the distal end thereof, according to one embodiment of the present disclosure, wherein the electrode catheter is disposed at one location within the distal portion of a catheter sheath.
Figure 9:
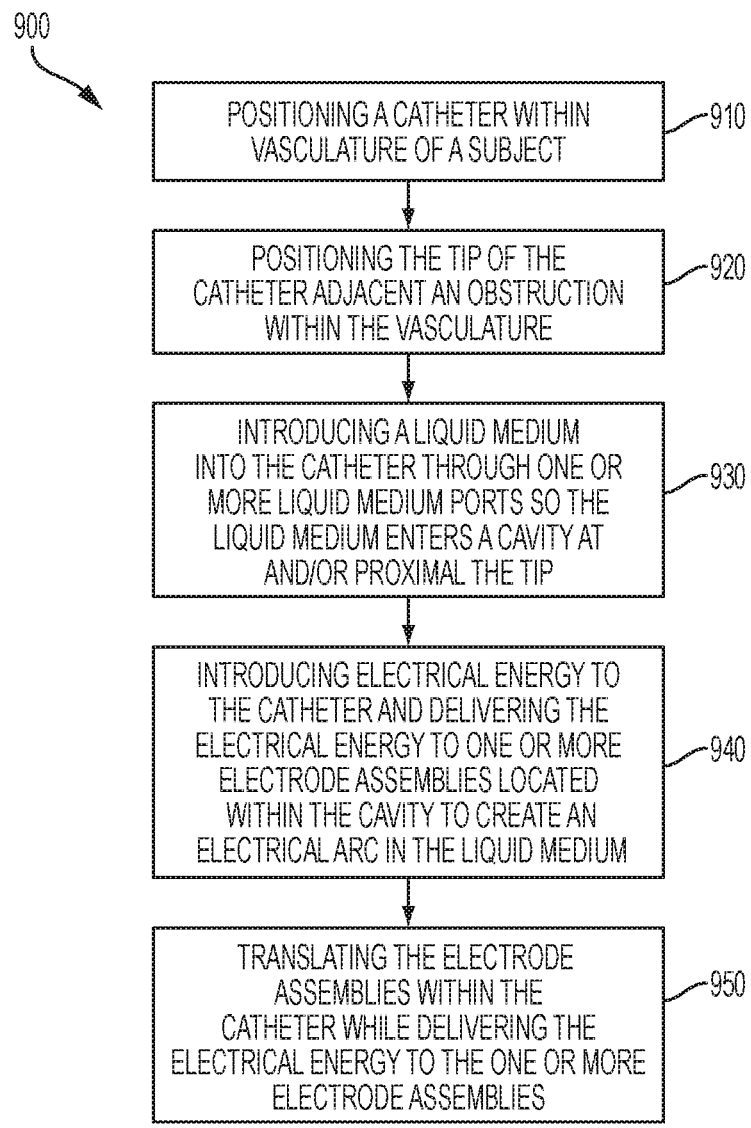
FIG. 9 is a representative flow diagram of a method of treating a subject using an electrically-induced pressure wave emitting catheter, according to one embodiment of the present disclosure.

Various shapes and configurations of deflectors are envisioned. For example, referring to FIG. 7, the electrode catheter 750 may include a deflector 792 disposed distally from the one or more electrode assemblies 786 of the electrode catheter 750, may be configured to direct the pressure waves in a radial direction less than 360 degrees (for example, 5 degrees, 10 degrees, 15 degrees, . . . , 30 degrees, . . . , 45 degrees, . . . , 60 degrees, . . . , 75 degrees, . . . , 90 degrees, . . . , 105 degrees, . . . , 120 degrees, . . . , 135 degrees, . . . , 150 degrees, . . . , 165 degrees, . . . , 180 degrees, etc.) about the circumference of the electrode catheter 750 and/or sheath 782. For example, the deflector 792 may have a solid construction with an opening facing a particular direction. And the shape and size of the opening within the deflector may dictate the direction that the pressure waves may travel. As depicted in FIG. 7, the electrode catheter 750 may translate axially within the sheath 782 along the longitudinal axis of the electrode catheter 750 and/or sheath 782. The present disclosure also contemplates that the electrode catheter 750 may rotate within the sheath 782 about the longitudinal axis of the electrode catheter 750 and/or sheath 782, thereby directing not only directing the pressure waves along a longitudinal direction but also about a radial direction.

The transfer of the energy produced by the creating a pressure wave to the vascular obstruction and/or to the walls of the vessel is sufficient to disrupt intraluminal as well as intimal and/or medial (within the tissue layer of the vascular wall) vascular obstructions (for example, calcium deposits). The forces generated by the pressure waves can propagate radially, including in forward (such as, parallel to the vessel), upward (such as, perpendicular to the vessel), and backward (such as, proximally) directions. Pressure waves produced in this manner can also be used to increase vessel compliance prior to performing another procedure, such as a traditional balloon angioplasty, drug-eluting balloon angioplasty and/or stent placement. That is, the pressure wave disruption of the intraluminal layer and/or medial layer and the vascular obstructions, can improve the vasculature's ability to absorb drugs, particularly when such drugs are applied with a drug eluting balloon.

Referring again to FIGS. 6 and 6A, the catheter system includes the electrode catheter 650 disposed within the sheath 682 and proximate the tip 680, thereby allowing the pressure waves to propagate radially from the sheath 650 and forward (such as, parallel to the vessel) from the tip. In order to ensure that the electrode catheter 650 is proximate the tip 680 to create a cavity between the distal end of the electrode catheter 650, the sheath 682 and the tip 680, the electrode catheter 650 and/or the sheath 682 may include stops and/or matingly engageable springs and/or recesses to maintain the electrode catheter 650 at the desirable distance proximate the tip 680. The stops and/or matingly engageable springs and/or recesses shall also be configured to allow the clinician to easily disengage the electrode catheter 650 from the sheath 682 so the electrode catheter 650 may translate within the sheath 682.

Referring to FIGS. 8 and 8A, if it is not desirable to slide the electrode catheter within the sheath, then the electrically-induced pressure wave emitting catheter sheath system may include electrode catheter 850 that is engageable with and removable from a cap 870. The cap 870 may include a relatively short sheath attached to a tip 880 and an optional shield 888. Similar to the embodiment in FIGS. 6 and 6A, the embodiment in FIGS. 8 and 8A may include matingly engageable springs and/or recesses that are configured to allow the clinician to easily engage and disengage the electrode catheter 850 from the cap 870.

The electrode catheter 850 may include an optional inner lumen, which may be used to insert a guidewire and/or the liquid medium. Or the electrode catheter 850 may include one or more additional lumens to serve independent purposes. Again, the proximal end of the electrode catheter is coupled to a high voltage pulse generator, and the distal end of the electrode catheter (or any position between the proximal and distal end of the electrode catheter) may include one or more electrode assemblies 800. Electrical cables within the electrode catheter couple the high voltage pulse generator to the one or more electrode assemblies. The liquid medium travels through the lumen 852 until being introduced from one or more liquid medium ports (not shown) into the cavity. The electrode assembly 800 is in direct contact with the liquid medium such that when electrical energy is produced by the electrode assembly 800, the liquid medium absorbs the pulsed electrical energy, which in turn generates a pressure wave and/or cavitation bubbles that produce additional pressure waves, thereby converting the pressure waves to mechanical energy via moving the tip 880 and/or transferring the pressure to the vascular occlusion through the tip 880.

Figure 10A:
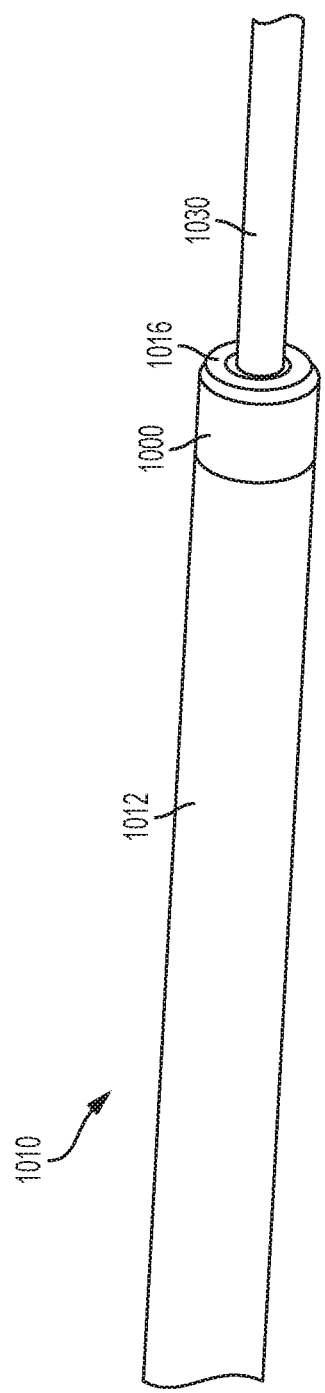
FIG. 10A is a perspective view of an electrode catheter and a guidewire, according to one embodiment of the present disclosure.

Referring to FIG. 10, there is depicted an electrode catheter 1010 and a guidewire 1020 extending through the lumen of the electrode 1010. The electrode catheter 1010 includes one or more electrode assemblies 1000 at its distal end. The electrode catheter 1010 may include a radiopaque marker.

Again, the present disclosure envisions a two-piece electrically-induced pressure wave emitting catheter sheath system or kit. Referring to FIG. 11A, the system 1110 may include an electrode catheter 1010 radially disposed within a sheath 1140. The system may optionally include a guidewire 1150 disposed within a lumen of the electrode catheter 1010. As discussed above, a liquid medium is introduced into the sheath 1120 distal to the electrode catheter 1010, particularly along the length of the electrode catheter that includes the electrode assemblies such that when the electrode assemblies are activated, the liquid absorbs the pulse of electrical energy and creates pressure waves and/or cavitation bubbles and additional resultant pressure waves. Although the liquid is not shown in this figure, the liquid may be introduced through a lumen in the electrode catheter 1010, a lumen in the sheath 1120 and/or the lumen or space between the electrode catheter 1010 and the sheath 1120. Regardless of which of these locations is used, one or more liquid medium ports located at or toward the proximal end of the catheter system will be also be used.

Figure 12:
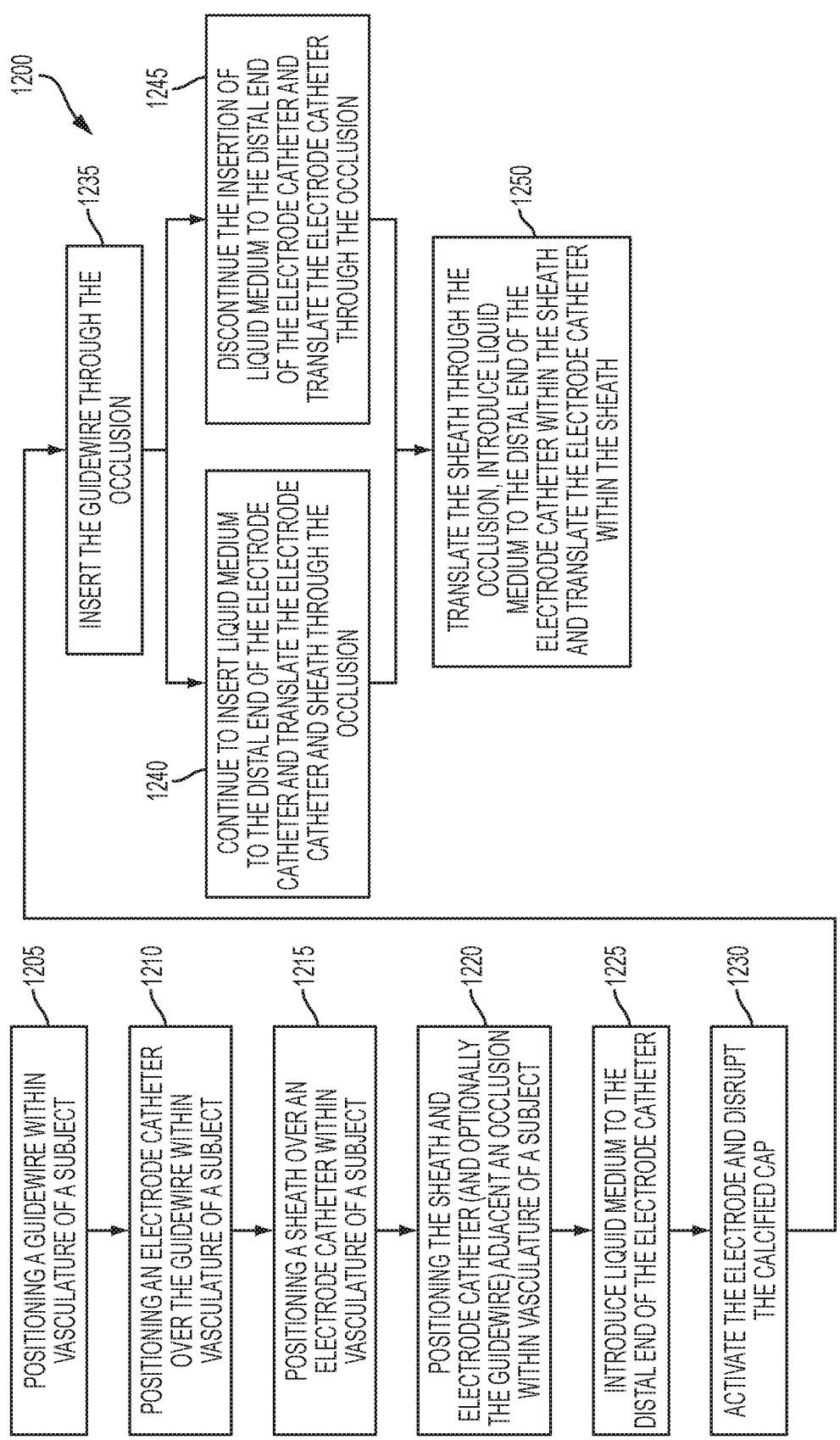
FIG. 12 is a representative flow diagram of a method of treating a subject using an electrode catheter and sheath, according to one embodiment of the present disclosure.

Referring to FIG. 12, there is depicted a representative flow diagram of a method 1200 of removing an occlusion using an electrode catheter 1010 in the presence of a liquid medium and disrupt a portion of the occlusion, and/or using the electrode catheter 1010 in conjunction with the sheath 1120 to create pressure waves in the presence of a liquid medium and disrupt a portion of the occlusion. The method 1200 may include the step 1205 of positioning a guidewire 1130 within the vasculature 1140 of a subject, the step 1210 of positioning an electrode catheter 1010 over the guidewire 1130 within the vasculature, the step 1215 of positioning a sheath 1120 over the electrode catheter 1010 within the vasculature, the step 1220 of positioning the sheath 1120 and electrode catheter 1010 (and optionally the guidewire 1130) adjacent an occlusion 1150 within the vasculature 1140 of a subject, and the step 1225 of introducing liquid medium to the distal end of the electrode catheter. Although the method illustrated in FIG. 12 depicts steps 1210, 1215, 1220 and 1225 in a particular order, steps 1210, 1215, 1220 and 1225 may be performed in any order.

Referring again to FIG. 11A, positioning the sheath 1120 and electrode catheter 1010 adjacent the occlusion 1150 creates a cavity for the liquid medium to collect distally of the electrode catheter 1010, particularly distally of the electrode assembly of the electrode catheter 1010. Specifically, FIG. 11A depicts the distal end of the electrode catheter 1010 proximal of the distal end of the sheath 1120. However, it is envisioned that the distal end of the electrode catheter 1010 may be disposed at or distally of the distal end of the sheath 1120, as long as there is liquid medium between the electrode assembly of the electrode catheter 1010 and the occlusion 1150. The axial locations of the electrode catheter 1010 and the sheath 1120 may be adjusted be translating either or both components with respect to one another. In order to visualize the respective locations of the electrode catheter 1010 and the sheath 1120 under fluoroscopy, the electrode catheter 1010 and the sheath 1120 may include radiopaque markers at any corresponding locations along their lengths.

Continuing to refer to FIG. 11A, once the sheath 1120 and electrode catheter 1010 are disposed adjacent the occlusion 1150, the liquid medium may be introduced to the distal end of the electrode catheter as set forth in step 1225 of FIG. 12. Continuing to refer to FIG. 12, step 1230 includes activating the electrode assemblies to create pressure waves in the presence of the liquid medium and disrupting a portion of the occlusion, particularly the calcified cap of the occlusion. The electrode catheter 1010 and sheath 1120 may be used to traverse the entire occlusion 1150, as set forth in step 1240 of FIG. 12 (and optionally step 1235 of FIG. 12), or only disrupt a portion of the occlusion 1150. If the electrode catheter 1010 and sheath 1120 are only used to disrupt a portion of the occlusion 1150, then the guidewire 1130 may penetrate and traverse the occlusion 1150. For example, FIG. 11B depicts the guidewire 1130 penetrating and traversing the occlusion 1150.

Figure 11:
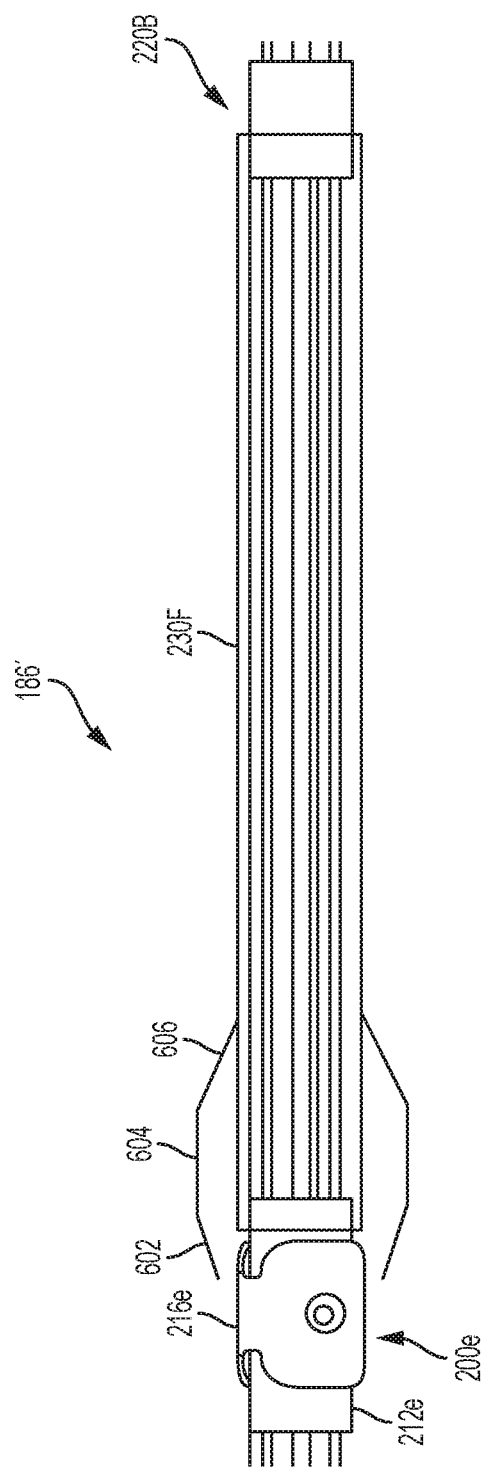
FIG. 11A is a perspective view of a kit within the vasculature of a patient, wherein the kit includes an electrode catheter radially disposed within a sheath and over a guidewire, according to one embodiment of the present disclosure, wherein the kit and guidewire are located proximally of an occlusion.
FIG. 11B is a perspective view of a kit within the vasculature of a patient, wherein the kit includes an electrode catheter radially disposed within a sheath and over a guidewire, according to one embodiment of the present disclosure, wherein the kit is located proximally of an occlusion, and the guidewire has penetrated the occlusion.
FIG. 11C is a perspective view of a kit within the vasculature of a patient, wherein the kit includes an electrode catheter radially disposed within a sheath and over a guidewire, according to one embodiment of the present disclosure, wherein the sheath is located proximally of an occlusion, and the electrode catheter and guidewire have penetrated the occlusion.
FIG. 11D is a perspective view of a kit within the vasculature of a patient, wherein the kit includes an electrode catheter radially disposed within a sheath and over a guidewire, according to one embodiment of the present disclosure, wherein the kit and guidewire have penetrated the occlusion.
Figure 11A:
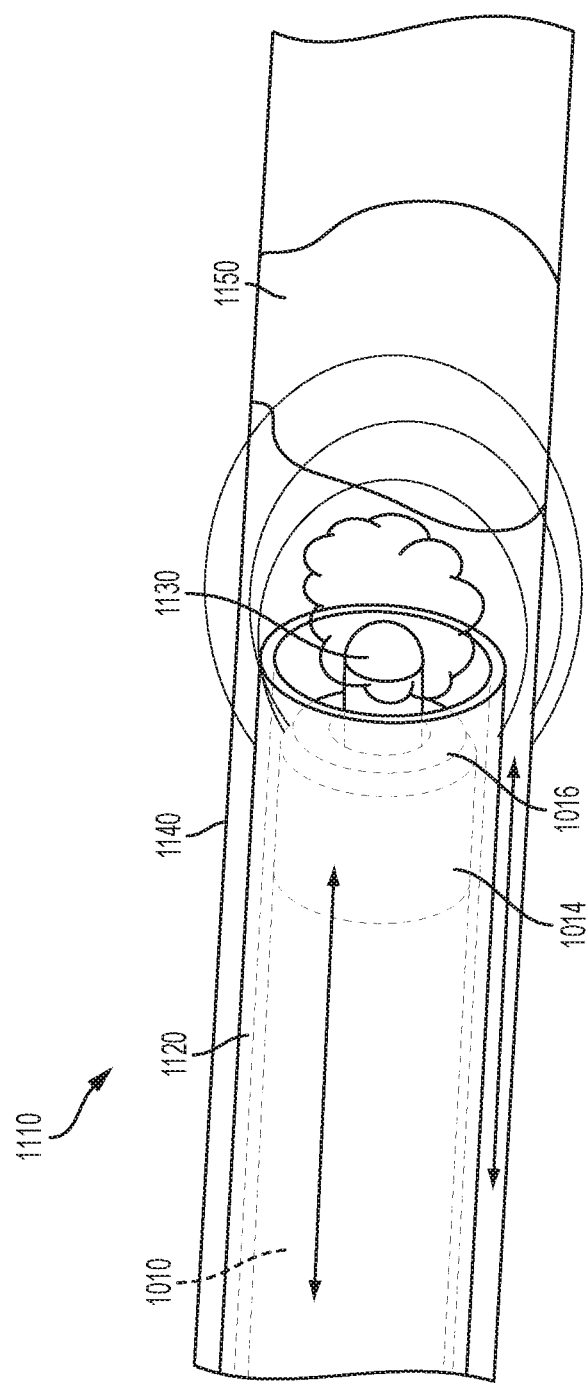

Referring to FIG. 11C, assuming that the electrode catheter 1010 and sheath 1120 are only used to disrupt a portion of the occlusion 1150', the electrode catheter 1120 may be used to traverse the occlusion 1150 without the sheath 1120. Referring to step 1245 of FIG. 12, the insertion of the liquid medium may be discontinued and the electrode catheter 1010 may be used to disrupt occlusion as the electrode catheter 1150 passes over the guidewire 1130 through the occlusion 1150' while the sheath 1120 remains proximal of the occlusion.

Figure 11D:
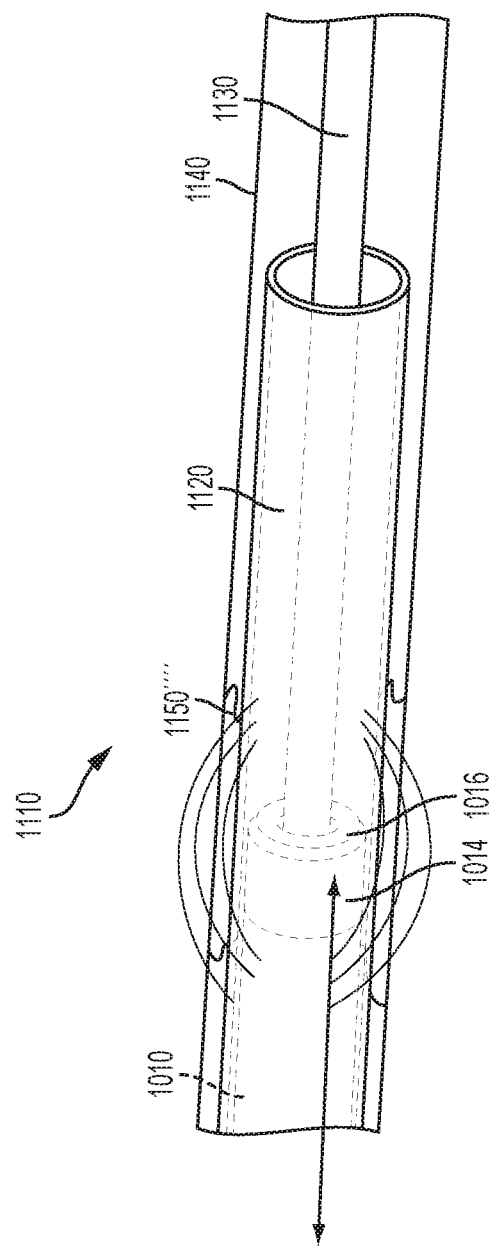

Once the entire occlusion has been traversed by the electrode catheter 1010, the opening created by the electrode catheter 1010 may be large enough to translate the sheath 1120 distally and through the occlusion. At this point, both the distal end of the sheath 1120 and the distal end of the electrode catheter 1010 should be distally of the occlusion. At this point, referring to FIG. 11D, the electrode catheter 1010 is able to translate proximally while the sheath 1120 remains stationary within the occlusion. Upon introducing the liquid medium into the sheath 1120 in front of the electrode catheter 1010, the high voltage pulse generator may be activated, thereby creating pressure waves in the presence of the liquid medium. At least a portion of the pressure waves are directed radially from the electrode assemblies, and as the electrode catheter 1010 translate proximally within the sheath 1120, the pressure waves transmit through the sheath 1120 and/or the sheath 1120 itself expands and contracts, thereby disrupting the remainder of the occlusion 1150'''.

To ensure that the majority of the remainder of the occlusion 1150''' is disrupted, and if desired, disrupt the intraluminal layer and/or medial layer and the vascular obstructions, the electrode catheter 1010 may be repeatedly translated distally and proximally within the sheath 1120. As discussed above, disruption of the intraluminal layer and/or medial layer and the vascular obstructions, can improve the vasculature's ability to absorb drugs, particularly when such drugs are applied with a drug eluting balloon. Also, it is contemplated that prior to, during and/or after any step in the process outlined in FIG. 12, the electrode catheter 1010 may be used individually to disrupt a portion of the occlusion, or the electrode catheter 1010 may be used in conjunction with the sheath 1120.

Figure 13:
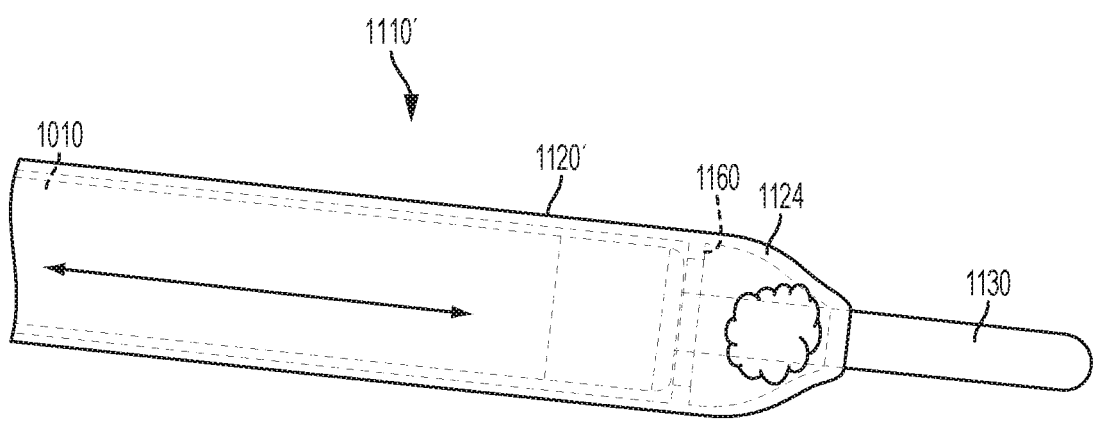
FIG. 13 is an elevation view of a kit that includes an electrode catheter radially disposed within a sheath and over a guidewire, according to one embodiment of the present disclosure.

FIGS. 11A-11D illustrate the catheter system as having a sheath 1120 with an open distal end or tip 1124. Referring to FIG. 13, the sheath 1120' may have a tip 1124 that is fully or partially closed. For example, if it is desirable to have a guidewire 1130 pass through the electrode catheter 1010 and the sheath 1120', the tip 1124 will only be partially closed, but if it is not necessary to utilize a guidewire, then the tip 1124 may be fully closed.

Similar to FIGS. 11A-11D, the electrode catheter 1010 may translate distally and/or proximally within the sheath 1120'. In order to ensure that a cavity remains between the distal end of the electrode catheter 1010 and the proximal end of the tip of the sheath 1120', the sheath 1120' may include one or more internal stops 1160. The shape of the tip 1124 may be configured similar to the tips 180 illustrated and described with respect to FIGS. 2-6 such that the catheter system 1110', including the electrode catheter 1010 tip 1124, is configured such that the energy produced by the pressure waves is captured within the cavity and the forces generated by the pressure waves propagate longitudinally, including in a forward (such as, parallel with the vessel) direction, thereby increasing the tip's ability to disrupt, destroy and/or penetrate the vascular obstructions.

Figure 14A:
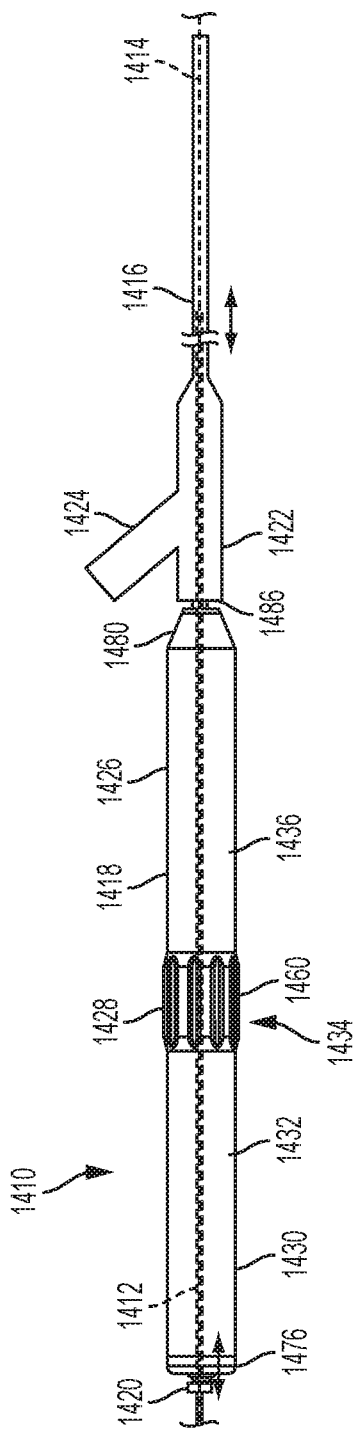
FIG. 14A is an elevation view of a kit that includes an electrode catheter radially disposed within a handle and a sheath and over a guidewire, according to one embodiment of the present disclosure.
Figure 14B:
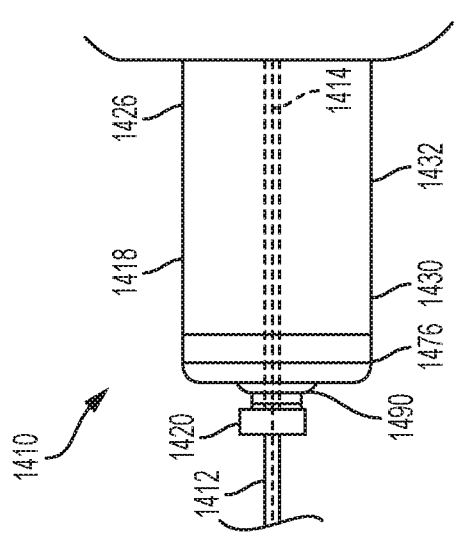
FIG. 14B is a detail elevation view of the electrode catheter and the handle of FIG. 14A at a proximal end of the handle.

Referring to FIGS. 14A and 14B, an electrically-induced angioplasty catheter sheath system 1410 generally includes an electrically-induced pressure wave emitting catheter 1412, such as an electrode catheter, a guidewire 1414, a sheath 1416, and a handle 1418 that translatably couples the electrode catheter 1412 to the sheath 1416. The electrode catheter 1412, the guidewire 1414, and the sheath 1416 may be similar to, for example, the components of the two-piece catheter systems or kits described herein. As a specific example, the electrode catheter 1412, the guidewire 1414, and the sheath 1416 may be similar to the components described above in connection with FIGS. 11A-11D. The electrode catheter 1412 is disposed within a lumen of the sheath 1416 and the handle 1418, and the electrode catheter 1412 includes a proximal coupling 1420 for coupling to the handle 1418. The guidewire 1414 is disposed within a lumen of the electrode catheter 1412. The sheath 1416 includes a proximal coupling 1422 for coupling to the handle 1418.

A liquid medium is introduced into the sheath 1416 distal to the electrode catheter 1412, particularly distal to the electrode assemblies of the electrode catheter 1412 such that when the high voltage pulse generator and electrode assemblies are activated, the liquid absorbs the electrical energy and creates pressure waves and/or cavitation bubbles and resultant pressure waves. The liquid is introduced via the lumen or space between the electrode catheter 1412 and the sheath 1416, which in turn receives the liquid from a proximal port 1424 coupled to the sheath 1416.

Referring now to FIGS. 14A, 14B, 15A-15G, the handle 1418 generally includes a base 1426 that couples to the sheath 1416 and a drive mechanism 1428 that couples to the electrode catheter 1412. As described in further detail below, a portion of the drive mechanism 1428 is translatably coupled to the base 1426 to facilitate translating the electrode catheter 1412 within the lumen of the sheath 1416 (for example, to the various positions shown in FIGS. 11A-11D). The drive mechanism 1428 may be translated to a proximal position relative to the base 1426 (see FIGS. 15A-15C), a distal position relative to the base 1426 (see FIGS. 15E and 15F), and an infinite number of intermediate positions therebetween (see FIGS. 15D and 15G). As a result, the electrode catheter 1412 may be translated to corresponding positions relative to the sheath 1416.

Figure 16A:
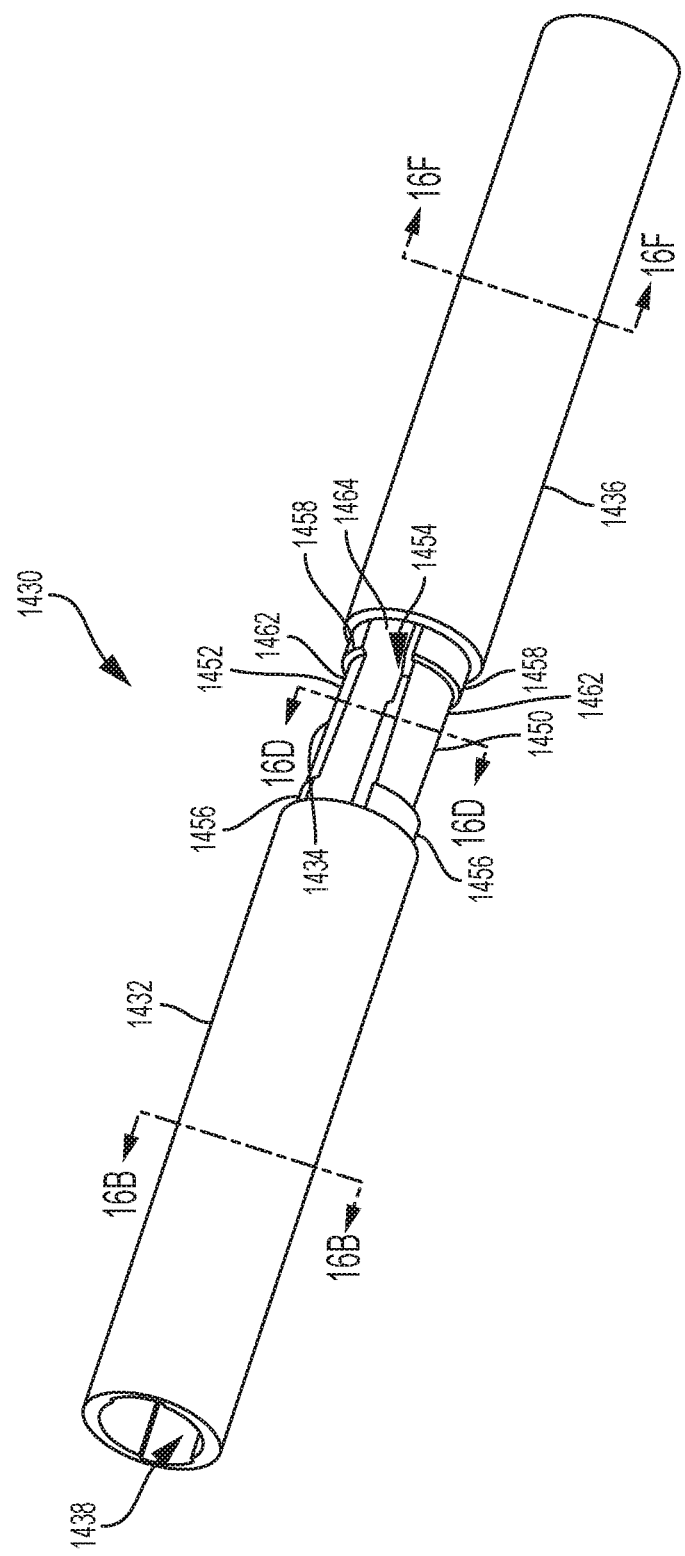
FIG. 16A is a perspective view of a frame of the handle of FIG. 14A.
Figure 17:
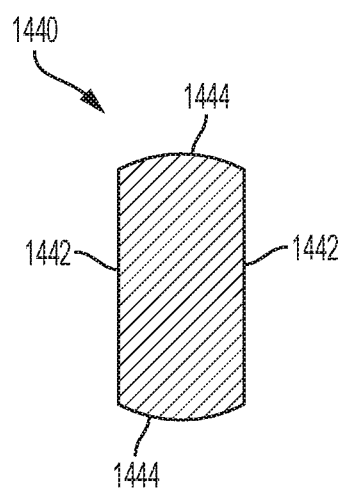
FIG. 17 is an elevation cross-sectional view of the shaft of the handle of FIG. 14A.

Referring now to FIGS. 14A-17, the base 1426 includes an elongated, hollow frame 1430 that movably couples to the drive mechanism 1428. The frame 1430 includes a proximal portion 1432, an intermediate portion 1434, and a distal portion 1436. The proximal portion 1432 defines a proximal passageway 1438 for translatably receiving a shaft 1440 of the drive mechanism 1428 therein. Referring specifically to FIGS. 16B, 16C, and 17, the proximal passageway 1438 may include a first key feature that, by coupling to a second key feature of the shaft 1440, inhibits rotation of the shaft 1440 relative to the frame 1430. For example, the second key feature of the shaft 1440 may be a non-circular cross-sectional area, and the first key feature of the proximal passageway 1438 may be a cross-sectional area that is approximately identical (that is, permitting sufficient clearance to permit relative longitudinal translation, but inhibit relative rotation and transverse translation) to the cross-sectional area of the shaft 1440, or a cross-sectional area that is approximately identical to a portion of the cross-sectional area of the shaft 1440. As a more specific example and as shown in FIGS. 16B, 16C, and 17, the shaft 1440 includes rectangle-like cross-sectional shape, with two opposing flat side surfaces 1442 and two opposing arcuate side surfaces 1444. The proximal passageway 1438 includes a cross-sectional area that is approximately identical to a portion of the cross-sectional area of the shaft 1440. Specifically, the proximal passageway 1438 is defined by four opposing flat side surfaces 1446 and two opposing arcuate side surfaces 1448. The flat side surfaces 1446 and the arcuate side surfaces 1448 engage the flat side surfaces 1442 and the arcuate side surfaces 1444 of the shaft 1440, respectively, to permit relative longitudinal translation, but inhibit relative rotation and transverse translation of the shaft 1440 relative to the frame 1430. In the present example, the proximal passageway 1438 is also defined by two additional opposing arcuate side surfaces 1449 that extend between the flat side surfaces 1446. The arcuate side surfaces 1449 are disposed apart from the shaft 1440 to reduce sliding friction between the shaft 1440 and the frame 1430.

Referring specifically to FIGS. 16A, 16D, and 16E, the intermediate portion 1434 of the frame 1430 includes a first bearing portion 1450, a second bearing portion 1452, and an opening 1454 extending therebetween and aligned with the proximal passageway 1438. Each of the first and second bearing portions 1450, 1452 includes first and second bearing surfaces 1456, 1458. The first and second bearing surfaces 1456, 1458 rotatably support a control element 1460 of the drive mechanism 1428. Each of the first and second bearing portions 1450, 1452 also includes a clearance surface 1462 between the bearing surfaces 1456, 1458. The clearance surface 1462 is also disposed radially inwardly relative to the bearing surfaces 1456, 1458. The clearance surface 1462, together with the opening 1454, facilitates driving engagement of the control element 1460 with the shaft 1440, as described in further detail below. Within the opening 1454, each of the first and second bearing portions 1450, 1452 includes a guide surface 1464. The guide surface 1464s translatably couple to the shaft 1440 and inhibit the shaft 1440 from rotating within the frame 1430.

Figure 15C:
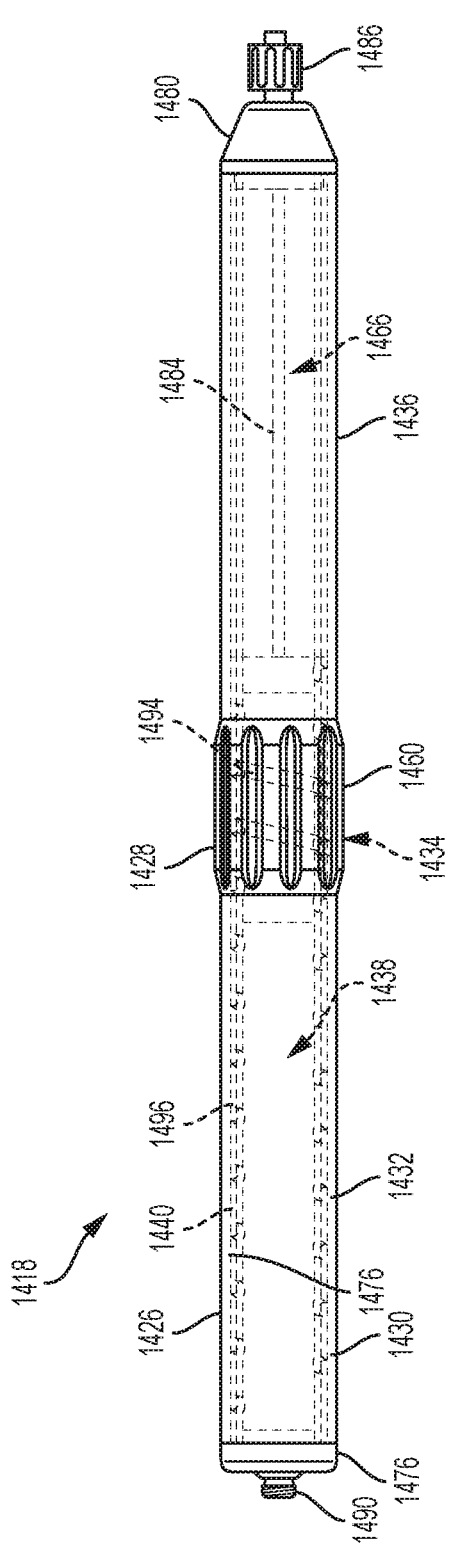
FIG. 15C is an elevation view of the handle of FIG. 14A, wherein several external components are partially transparent to illustrate internal components, and the shaft is shown in the proximal position.
Figure 15D:
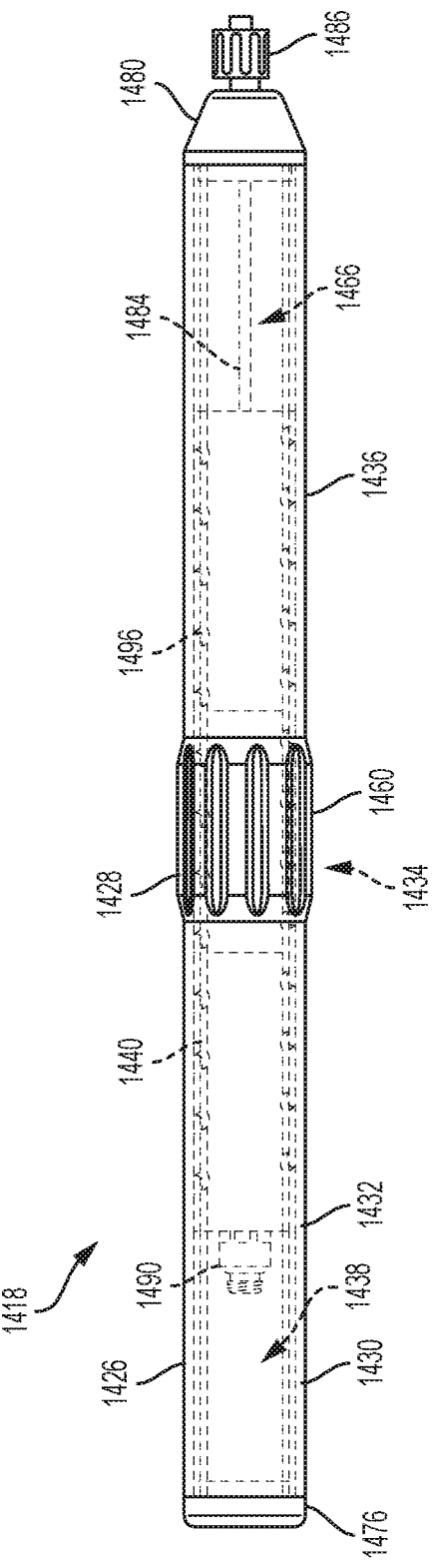
FIG. 15D is an elevation view of the handle of FIG. 14A, wherein several external components are partially transparent to illustrate internal components, and the shaft is shown in an intermediate position.
Figure 15I:
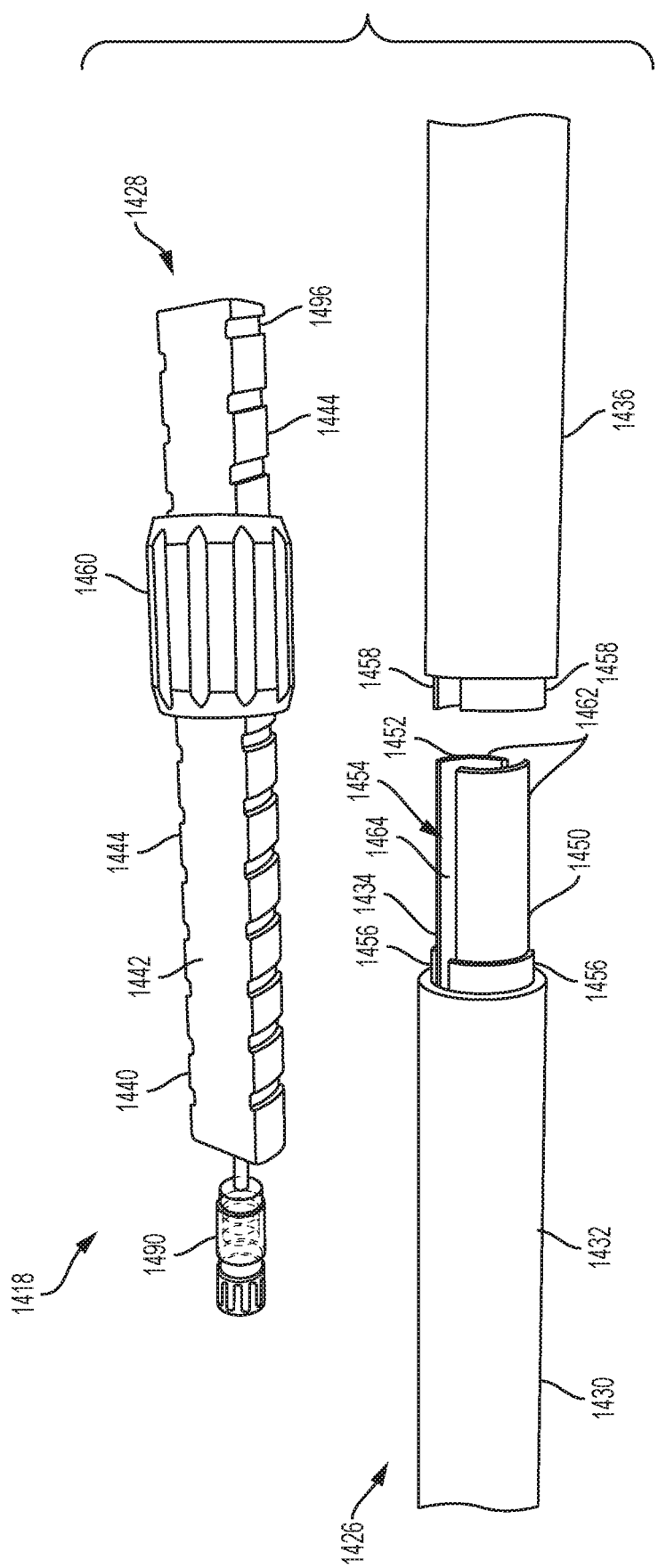
FIG. 15I is a detail exploded view of the handle of FIG. 14A.
Figure 15J:
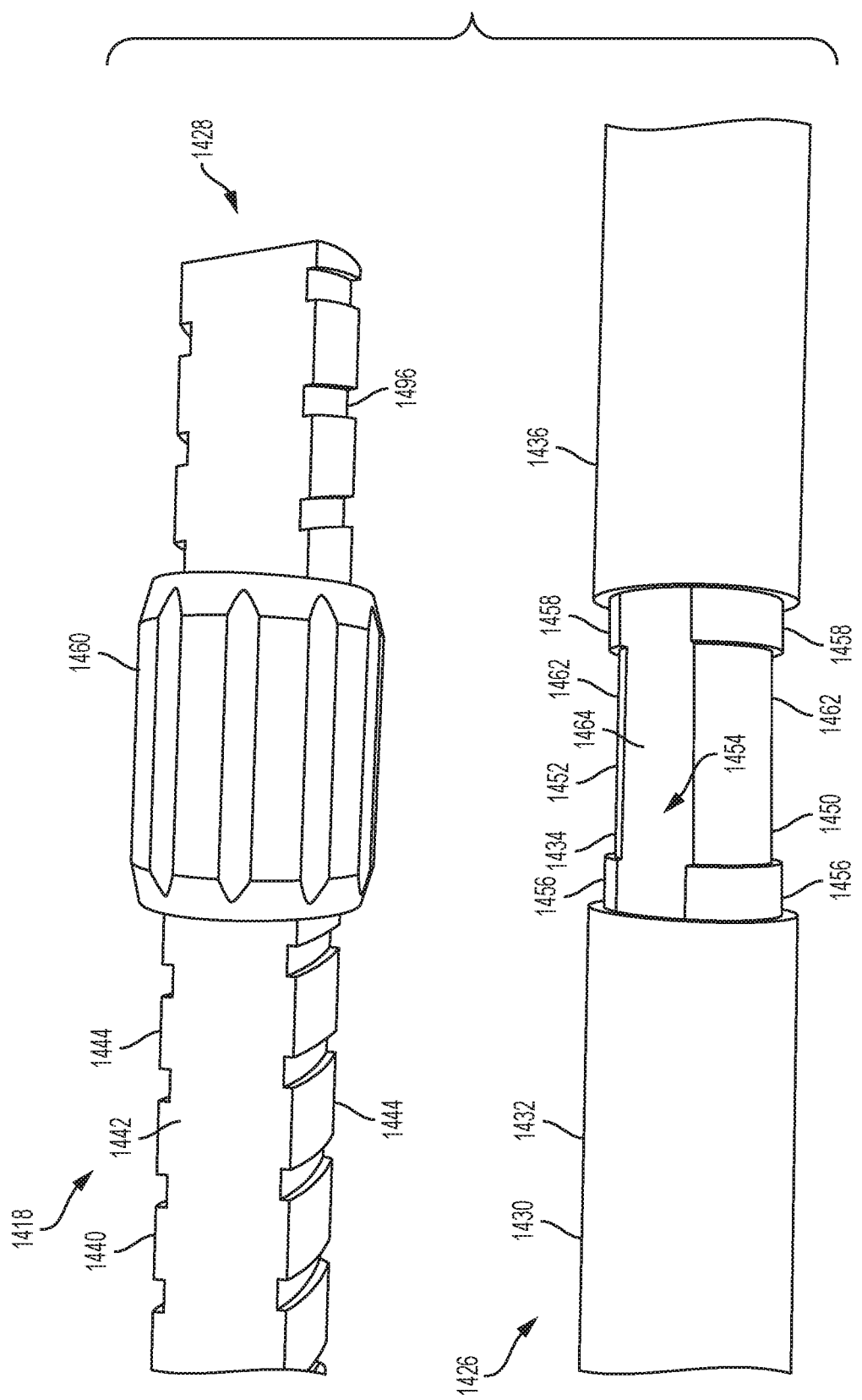
FIG. 15J is another detail exploded view of the handle of FIG. 14A.

Referring briefly to FIGS. 15H-15J, to facilitate assembly of the base 1426, each clearance surface 1462 may be monolithically coupled with the first bearing surface 1456, 1458. After positioning the shaft 1440 within the frame 1430 and the control element 1460 over the first bearing surface 1456, 1458 and the clearance surface 1462, each clearance surface 1462 may couple to the second bearing surface 1456, 1458 via, for example, press fit, one or more adhesives, snap connectors (not shown), or the like.

Referring to FIGS. 16A, 16F, and 16G, the distal portion 1436 of the frame 1430 may be similar to the proximal portion 1432 of the frame 1430. That is, the distal portion 1436 defines a distal passageway 1466 aligned with the opening 1454 for translatably receiving the shaft 1440. Referring specifically to FIGS. 16F, 16G, and 17 and in a similar manner to the proximal passageway 1438, the distal passageway 1466 may include a first key feature that, by coupling to the second key feature of the shaft 1440, inhibits rotation of the shaft 1440 relative to the frame 1430. For example, the second key feature of the shaft 1440 may be a non-circular cross-sectional area, and the first key feature of the distal passageway 1466 may be a cross-sectional area that is approximately identical to the cross-sectional area of the shaft 1440, or a cross-sectional area that is approximately identical to a portion of the cross-sectional area of the shaft 1440. In accordance with the specific example described above and as shown in FIGS. 16F, 16G, and 17, the distal passageway 1466 includes a cross-sectional area that is approximately identical to a portion of the cross-sectional area of the shaft 1440. Specifically, the distal passageway 1466 is defined by four opposing flat side surfaces 1468 and two opposing arcuate side surfaces 1470. The flat side surfaces 1468 and the arcuate side surfaces 1470 engage the flat side surfaces 1442 and the arcuate side surfaces 1444 of the shaft 1440, respectively, to permit relative longitudinal translation, but inhibit relative rotation and transverse translation of the shaft 1440 relative to the frame 1430. In the present example, the distal passageway 1466 is also defined by two additional opposing arcuate side surfaces 1472 that extend between the flat side surfaces 1468. The arcuate side surfaces 1472 are disposed apart from the shaft 1440 to reduce sliding friction between the shaft 1440 and the frame 1430.

Referring again to FIGS. 14A-16G, at its proximal end, the frame 1430 couples to a proximal cover 1476 (for example, via press fit, one or more adhesives, or the like). The proximal cover 1476 includes a proximal aperture 1478 (see FIGS. 15F and 15G) for permitting the electrode catheter 1412 to extend into the frame 1430. At its distal end, the frame 1430 couples to a distal cover 1480 (for example, via press fit, one or more adhesives, or the like). The distal cover 1480 includes a distal aperture 1482 (see FIGS. 15F and 15G) for permitting the electrode catheter 1412 to extend out of the frame 1430 and into the sheath 1416. The distal aperture 1482 press-fittingly receives a tube 1484 (for example, a hypotube 1484) that extends into the shaft 1440 and receives the electrode catheter 1412. The distal aperture 1482 also press-fittingly receives a distal coupling 1486 that detachably and sealingly couples to the proximal coupling 1422 of the sheath 1416.

Referring now to FIGS. 14A & 15A-15J, the drive mechanism 1428 generally including the shaft 1440 and the control element 1460. Referring specifically to FIGS. 15F-15J, the shaft 1440 includes a shaft 1440 passageway 1488 for permitting the electrode catheter 1412 to extend through the shaft 1440 and for receiving the tube 1484. The shaft 1440 passageway 1488 press-fittingly receives a proximal coupling 1490 that detachably and sealingly couples to the proximal coupling 1420 of the electrode catheter 1412. As such, movement of the control element 1460 relative to the base 1426 causes the shaft 1440 to translate within the base 1426, the electrode catheter 1412 thereby translates within the lumen of the sheath 1416.

The shaft 1440 passageway 1488 also receives a seal 1492, for example, an O-ring, which translatably engages the outer surface of the tube 1484. As such, the seal 1492 inhibits the liquid in the shaft 1440 passageway 1488 (received from the sheath 1416 via the distal coupling 1486 and the hypotube 1484) from exiting the shaft 1440 by flowing between the shaft 1440 and the tube 1484.

As described briefly above, the control element 1460 is rotatably supported by the frame 1430. The control element 1460 includes a first engagement feature that couples to a second engagement feature of the shaft 1440 such that rotation of the control element 1460 relative to the base 1426 causes translation of the shaft 1440 relative the base 1426 (and translation of the electrode catheter 1412 within the lumen of the sheath 1416). For example and as shown in the Figures, the first engagement feature may be a first threaded surface 1494 within the control element 1460, and the second engagement feature may be a second threaded surface 1496 formed on the arcuate side surfaces 1444 of the shaft 1440. Stated differently, the shaft 1440 may include a second, interrupted threaded surface that extends from the opening 1454 in the frame 1430 to engage the first threaded surface 1494 of the control element 1460. In any case, rotation of the control element 1460 and the first threaded surface 1494, together with the shaft 1440 being rotatably fixed within the frame 1430, causes translation of the second threaded surface 1496 and the shaft 1440 relative to the frame 1430 (and translation of the electrode catheter 1412 within the lumen of the sheath 1416).

The degree of force generated by the pressure waves depends in part on the degree of absorption of the electrical energy by the liquid medium as well as total energy produced by the electrode assemblies. Generally, the greater the absorption of the electrical energy by the liquid medium 160, the greater the force generated by the pressure waves. Also, the greater the amount of the electrical energy delivered to the liquid medium 160, the greater the force generated by the pressure waves. In some cases, the liquid medium can be contrast medium (for example, iodine-containing contrast medium or gadolinium contrast medium) and/or the liquid medium can be a contrast solution comprising a biocompatible fluid (for example, saline) in which a contrast dye(s) or particle(s) have been mixed at various concentrations.

The total number of pulses administered during a particular treatment period depends on a variety of factors, including patient characteristics, the type of condition being treated, and the specific characteristics of the vascular obstruction, as one of ordinary skill in the art would readily appreciate based on the present disclosure. In some cases, the total number of pulses administered during a treatment period can range from a single pulse to any number of pulses generated in a 10 second treatment period, a 15 second treatment period, a 20 second treatment period, a 25 second treatment period, a 30 second treatment period, up to a 1 minute treatment period. Treatment periods can be repeated depending on the extent of the vascular obstruction remaining after initial treatment.

Additionally or alternatively, methods of the present disclosure also include activating at least one proximal electrode assembly enclosed within the sheath assembly to send pulses of electrical energy through the liquid medium and propagating pressure waves to assist in stent deployment. Pressure waves generated from cavitation bubbles can assist in seating or expanding the stent to its full diameter as part of a medical procedure.

As discussed above, activating one or more electrode assemblies and transmitting pulses of electrical energy into the liquid medium produces cavitation bubbles. Upon producing pulses of electrical energy from an electrode assembly, such as an electrode catheter, within a sheath that contain a liquid medium, the cavitation bubbles may be produced within the interior of the sheath and/or exterior to the sheath. Assuming that the cavitation bubbles are created on the interior of the sheath, it may be desirable to limit some or all of the potential expansion of the relevant portion of the sheath caused by the cavitation bubbles. That is, it may be desirable to reduce or prevent the sheath's ability to expand and contract upon creation of the cavitation bubbles therein so as to reduce or prevent the sheath from applying a hydraulic force or pressure to the vascular occlusion and/or to the walls of the vessel. Also, assuming that the cavitation bubbles are created on exterior of the sheath within the vessel wall, it may be desirable to reduce or prevent the formation of such cavitation bubbles so as to reduce or prevent the cavitation bubbles themselves from applying a hydraulic force or pressure to the vascular occlusion and/or to the walls of the vessel.

Figure 18:
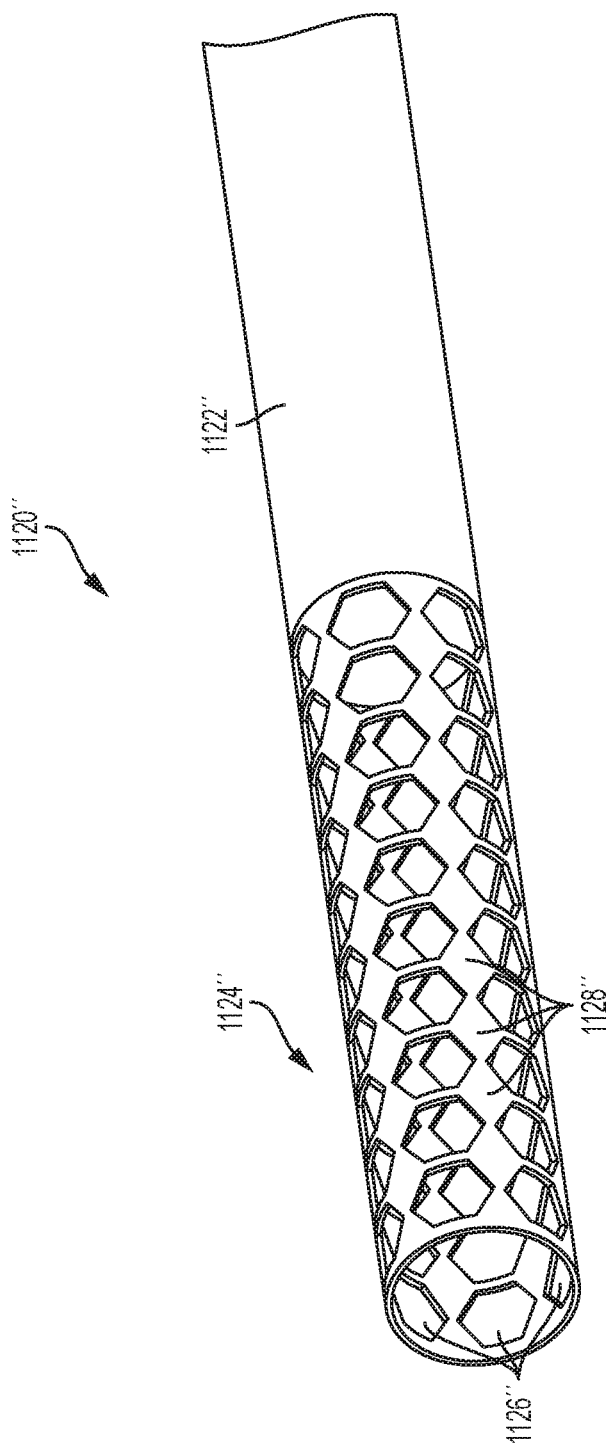
FIG. 18 is a perspective view of an outer sheath comprising a porous attenuating member, according to one embodiment of the present disclosure.

Referring to FIG. 18, there is depicted a perspective view of biocompatible sheath 1120" that can be used in conjunction with an electrode catheter or any of the earlier embodiments to perform a method of treating a subject, such as removing or treating a vascular occlusion. The sheath 1120" may include a sleeve or jacket 1122" and a porous attenuating member 1124". FIG. 18 illustrates the porous attenuating member 1124" as being exposed and coupled to the distal end of the sleeve 1122" via an adhesive. The porous attenuating member 1124", however, can alternatively be integrally disposed within the sleeve 1122", disposed on the exterior of the sleeve 1122" and/or disposed on the interior of the sleeve 1122". Additionally, if the porous attenuating member 1124" is coupled to the distal end of the sleeve 1122" or the porous attenuating member 1124" is integrally disposed within the sleeve 1122" or disposed on the interior of the sleeve 1122", the entire porous attenuating member 1124" may be covered (unexposed) by the sleeve 1122", the entire porous attenuating member 1124" may be exposed, or a portion (for example, distal portion) of the porous attenuating member 1124" may be exposed and another portion (for example, proximal portion) may be covered.

FIG. 18 also illustrates the porous attenuating member 1124" as being disposed at the distal end of the sheath 1120". The porous attenuating member 1124", however, may alternatively and/or additionally as be disposed at the proximal end of the sheath 1120", the central portion of the sheath 1120", any location or multiple locations between the proximal end and distal end of the sheath 1120", or in the entire length or substantially the entire length of the sheath 1120".

The porous attenuating member 1124" has two purposes. One purpose is to reinforce the sleeve 1122" and/or the sheath 1120", and the other purpose is to reduce or prevent the formation of cavitation bubbles exterior of the attenuating member 1124", the sleeve 1122" and/or the sheath 1120". Regarding the reinforcing the sleeve 1122", coupling the porous attenuating member 1124" with the sleeve 1122" may reduce or prevent the sheath's ability to expand and contract upon creation of the cavitation bubbles therein so as to reduce or prevent the sleeve 1122" from applying a hydraulic force or pressure to the vascular occlusion and/or to the walls of the vessel. Both the attenuating member 1124" and the sleeve 1122" are constructed of biocompatible materials. Coupling the porous attenuating member 1124" with the sleeve 1122" forms a rigid or semi-rigid structure within the sheath 1120" such that it applies a small hydraulic force or it does not apply a hydraulic force to the vascular occlusion and/or to the walls of the vessel upon formation of cavitation bubbles therein. It may be desirable that the majority or only force(s) applied to the vascular occlusion and/or to the walls of the vessel are a result of the pressure waves that pass through the 1120", thereby allowing more precise control over the pressure waves.

Regarding the other purpose of the attenuating member 1124", which is to reduce or prevent the formation of cavitation bubbles exterior of the attenuating member 1124", the sleeve 1122" and/or the sheath 1120" and continuing to refer to FIG. 18, the openings 1126" within the attenuating member 1124" may prevent the formation of large sized cavitation bubbles on the sheath 1120". The openings 1126" not only allow the pressure waves to pass therethrough, but the quantity and size of the openings 1126", particularly with respect to the remainder of the structural mass (or portions thereof 1128") of the sleeve 1122", may also limit the size of the cavitation bubbles that can form on the exterior of the sheath 1120". The relationship between the open area and the closed area (or the ratio of the open area to the overall area) within the attenuating member 1124" should be such that a sufficient amount of the pressure waves pass through the attenuating member 1124". And the size of the openings 1126" should allow the pressure waves to pass therethrough, while also limiting the size of the cavitation bubbles that can form on the exterior of the sheath 1120". Accordingly, it may be desirable for the ratio of the open area to the overall area of the attenuating member 1124" to be between 1 percent-99 percent, including any increment therebetween such as 2 percent, 3 percent, 4 percent, 5 percent, 6 percent, 7 percent, 8 percent, 9 percent, 10 percent, . . . , 15 percent . . . 20 percent, . . . 25 percent, . . . , 30 percent, . . . , 35 percent, . . . , 40 percent, . . . , 45 percent, . . . , 50 percent, . . . , 55 percent, . . . , 60 percent, . . . , 65 percent, . . . , 70 percent, . . . , 75 percent, . . . , 80 percent, . . . , 85 percent, . . . , 90 percent, 91 percent, 92 percent, 93 percent, 94 percent, 95 percent, 96 percent, 97 percent, and 98 percent. It may also be desirable for the ratio of the open area to the overall area of the attenuating member 1124" to be within a particular range such as between 5 percent to 95 percent, 10 percent to 90 percent, 15 percent to 85 percent, 20 percent to 80 percent, 25 percent to 75 percent, 30 percent to 70 percent, 35 percent to 65 percent, 40 percent to 60 percent, and 45 percent to 55 percent. Additionally, for any of the above listed ratios it may be desirable for each opening to have a particular size, such as between 50 microns to 1000 microns (1 millimeter), including any increment therebetween such as 100 microns, . . . 125 microns, . . . , 150 microns, 175 microns, . . . , 200 microns, . . . , 225 microns, . . . , 250 microns, . . . , 300 microns, . . . , 325 microns, . . . , 350 microns, . . . , 400 microns, . . . 425 microns, . . . , 450 microns, . . . , 475 microns, . . . , 500 microns, . . . , 525 microns, . . . , 550 microns, . . . , 575 microns, . . . , 600 microns, . . . , 625 microns, . . . , 650 microns, . . . , 675 microns, . . . , 700 microns, . . . , 725 microns, . . . , 750 microns, . . . , 775 microns, . . . , 800 microns, . . . , 825 microns, . . . , 850 microns, . . . , 875 microns, . . . and 950 microns. It may also be desirable for the size openings within the attenuating member 1124" to be within a particular range such as between 100 to 900 microns, 150 to 850 microns, 200 to 800 microns, 250 to 750 microns, 300 to 700 microns, 350 to 650 microns, 400 to 600 microns, and 450 to 550 microns.

Figure 18A:
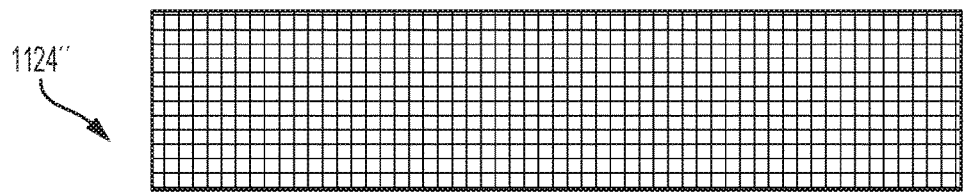
FIG. 18A is a side elevation view of a porous attenuating member comprising a plurality of square-shaped openings, according to one embodiment of the present disclosure.
Figure 18B:
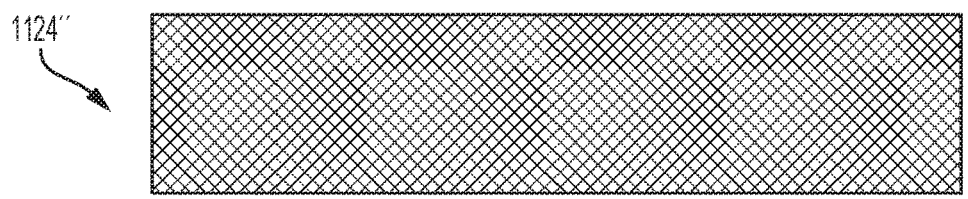
FIG. 18B is a side elevation view of a porous attenuating member comprising a plurality of diamond-shaped openings, according to one embodiment of the present disclosure.
Figure 18C:
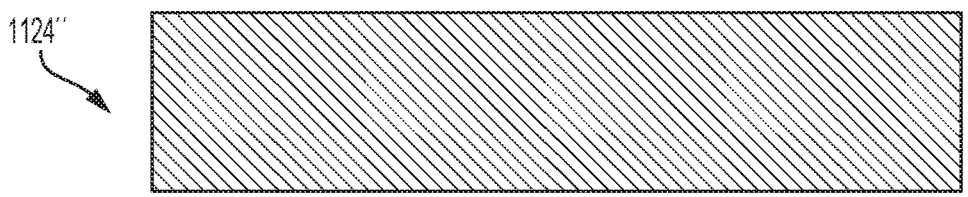
FIG. 18C is a side elevation view of a porous attenuating member comprising a plurality of openings formed by a helical structure wound in a particular direction, according to one embodiment of the present disclosure.
Figure 18D:
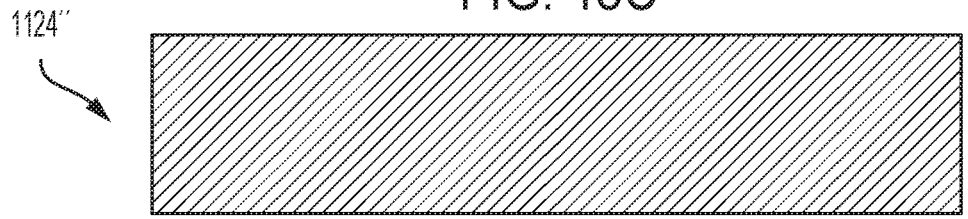
FIG. 18D is a side elevation view of a porous attenuating member comprising a plurality of openings formed by a helical structure wound in a particular direction, according to one embodiment of the present disclosure.
Figure 18E:
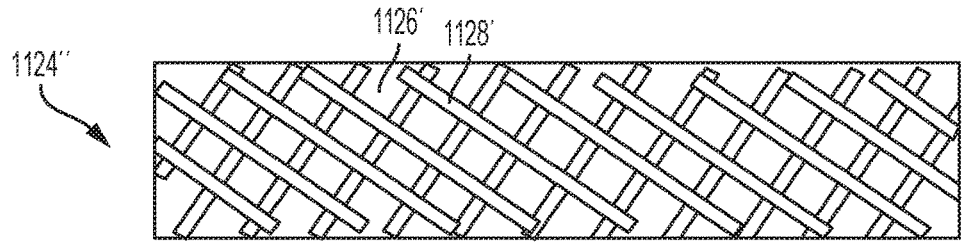
FIG. 18E is a side elevation view of a porous attenuating member comprising a plurality of openings formed by a helical wound ribbons, according to one embodiment of the present disclosure.
Figure 18F:
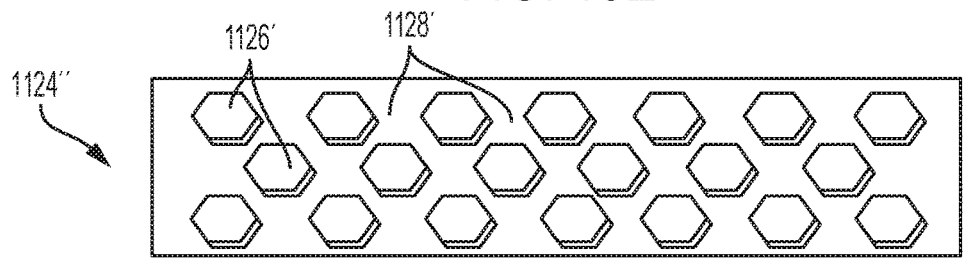
FIG. 18F is a side elevation view of a porous attenuating member comprising a plurality of openings, according to one embodiment of the present disclosure.

The openings 1126" in the attenuating member 1124" depicted in FIG. 18 are shown as hexagons, which are disposed around the circumference of the attenuating member 1124", as well as along its length. Although the openings 1126" in the attenuating member 1124" are illustrated as hexagons, the openings may have an alternate shape, such as a circle, oval, triangle, square, rectangle, polygon, diamond, pentagon, heptagon, octagon, nonagon, and decagon. For example, FIG. 18A illustrates a side view of a porous attenuating member 1124" comprising a plurality of square-shaped openings; FIG. 18B is a side view of a porous attenuating member 1124" comprising a plurality of diamond-shaped openings, FIG. 18C is a side view of a porous attenuating member 1124" comprising a plurality of openings formed by a helical structure wound in a particular direction (for example, clockwise or left to right) while FIG. 18D is a side view of a porous attenuating member 1124" comprising a plurality of openings formed by a helical structure wound in an alternate direction (for example, counter-clockwise or right to left). Additionally, the two helically formed porous attenuating members 1124" may be combined to form the porous attenuating member 1124" depicted in FIG. 18E. The porous attenuating member 1124" depicted in FIG. 18E is similar to the porous attenuating member 1124" depicted in FIG. 18B, but the porous attenuating member 1124" depicted in FIG. 18B is braided and the porous attenuating member 1124" depicted in FIG. 18E is wound or formed by one or two hypotubes. Additionally, the structural mass (or portions thereof 1128") of the porous attenuating member 1124" depicted in FIG. 18E is larger than the structural mass (or portions thereof 1128") of the porous attenuating member 1124" depicted in FIG. 18E because braided materials are generally smaller in size.

Figure 19:
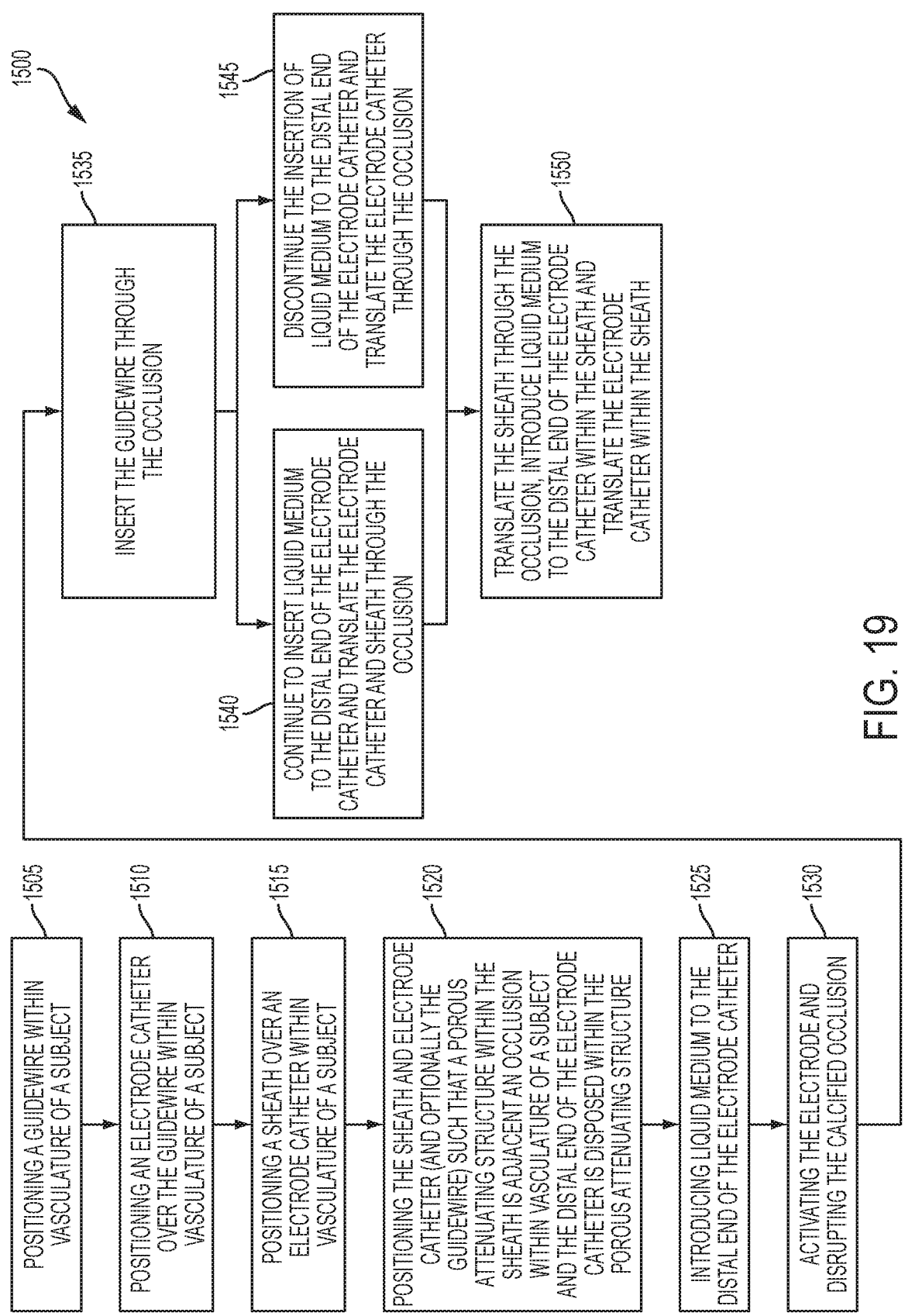
FIG. 19 is a representative flow diagram of a method of treating a subject using an electrode catheter and sheath, according to one embodiment of the present disclosure.

Referring to FIG. 19, there is depicted a representative flow diagram of a method 1500 of treating a subject using an electrode catheter 1010 (such as the electrode catheter depicted in FIG. 10 or an electrode catheter the same or similar to the one depicted in FIGS. 1D, 1G, 1H and 1I) and the sheath 1120" (depicted in FIG. 18) in the presence of a liquid medium to disrupt a portion of an occlusion, and/or, and/or using the electrode catheter 1010 in conjunction with the sheath 1120 in the presence of a liquid medium to disrupt an occlusion and/or create pressure waves in the presence of a liquid medium and disrupt a portion of the occlusion as depicted in FIGS. 11A-11D. The method 1500 may include the step 1505 of positioning a guidewire 1130 within the vasculature 1140 of a subject, the step 1510 of positioning an electrode catheter 1010 over the guidewire 1130 within the vasculature 1515, the step 1515 of positioning a sheath 1120 over the electrode catheter 1010 within the vasculature, the step 1520 of positioning the sheath 1120 and electrode catheter 1010 (and optionally the guidewire 1130) adjacent an occlusion 1150 within the vasculature 1140 of a subject, and the step 1525 of introducing of introducing liquid medium to the distal end of the electrode catheter. Although the method illustrated in FIG. 19 depicts steps 1510, 1515, 1520 and 1525 in a particular order, steps 1210, 1215, 1220 and 1225 may be performed in any order.

Referring again to FIG. 11A, positioning the sheath 1120 and electrode catheter 1010 adjacent the occlusion 1150 creates a cavity for the liquid medium to collect distally of the electrode catheter 1010, particularly proximally, at and/or distally of the electrode assemblies of the electrode catheter 1010. Specifically, FIG. 11A depicts the distal end of the electrode catheter 1010 proximal of the distal end of the sheath 1120. However, it is envisioned that the distal end of the electrode catheter 1010 may be disposed at or distally of the distal end of the sheath 1120, as long as there is liquid medium between the electrode assembly of the electrode catheter 1010 and the occlusion 1150. The axial locations of the electrode catheter 1010 and the sheath 1120 may be adjusted be translating either or both components with respect to one another. In order to visualize the respective locations of the electrode catheter 1010 and the sheath 1120 under fluoroscopy, the electrode catheter 1010 and the sheath 1120 may include radiopaque markers at any corresponding locations along their lengths.

Continuing to refer to FIG. 11A, once the sheath 1120 and electrode catheter 1010 are disposed adjacent the occlusion 1150, the liquid medium may be introduced to the distal end of the electrode catheter as set forth in step 1525 of FIG. 19. Continuing to refer to FIG. 19, step 1530 includes providing electrical pulses to the electrode assemblies to create pressure waves in the presence of the liquid medium and disrupting a portion of the occlusion, particularly the calcified cap of the occlusion. The electrode catheter 1010 and sheath 1120 may be used to traverse the entire occlusion 1150, as set forth in step 1540 of FIG. 19 (and optionally step 1535 of FIG. 19), or only disrupt a portion of the occlusion 1150. If the electrode catheter 1010 and sheath 1120 are only used to disrupt a portion of the occlusion 1150, then the guidewire 1130 may penetrate and traverse the occlusion 1150. For example, FIG. 11B depicts the guidewire 1130 penetrating and traversing the occlusion 1150.

Referring to FIG. 11C, assuming that the electrode catheter 1010 and sheath 1120 are only used to disrupt a portion of the occlusion 1150', the electrode catheter 1120 may be used to traverse the occlusion 1150 without the sheath 1120. Referring to step 1545 of FIG. 19, the insertion of the liquid medium may be discontinued and the electrode catheter 1010 may be used to disrupt the occlusion as the electrode catheter 1150 passes over the guidewire 1130 through the occlusion 1150' while the sheath 1120 remains proximal of the occlusion.

Referring to step 1550 of FIG. 19 and once the entire occlusion has been traversed by the electrode catheter 1010, the opening created by the electrode catheter 1010 should be large enough to translate the sheath 1120 distally and through the occlusion. At this point, both the distal end of the sheath 1120 and the distal end of the electrode catheter 1010 should be distally of the occlusion. At this point, referring to FIG. 11D, the electrode catheter 1010 is able to translate proximally while the sheath 1120 remains stationary within the occlusion. Upon introducing the liquid medium into the sheath 1120 in front of the electrode catheter 1010, the electrode may be activated, thereby creating pressure waves in the presence of the liquid medium. At least a portion of the pressure waves are directed radially, and as the electrode catheter 1010 translate proximally within the sheath 1120, the pressure waves transmit through the sheath 1120 and/or the sheath 1120 itself expands and contracts, thereby disrupting the remainder of the occlusion 1150'''.

To ensure that the majority of the remainder of the occlusion 1150''' is disrupted, and if desired, disrupt the intraluminal layer and/or medial layer and the vascular obstructions, the electrode catheter 1010 may be repeatedly translated distally and proximally within the sheath 1120. As discussed above, disruption of the intraluminal layer and/or medial layer and the vascular obstructions, can improve the vasculature's ability to absorb drugs, particularly when such drugs are applied with a drug eluting balloon. Also, it is contemplated that prior to, during and/or after any step in the process outlined in FIG. 19, an electrode catheter may be used individually to disrupt a portion of the occlusion.

As discussed above, producing pulses of electrical energy from an electrode assembly in a liquid medium creates pressure waves and/or cavitation bubbles and additional resultant pressure waves that disrupt at least a portion of a vascular obstruction. The catheter may include a guidewire lumen through which a guidewire can pass and cross the occlusion. It may also be desirable to excite and vibrate the guidewire to increase the guidewire's ability to pierce and cross the occlusion. Accordingly, the present disclosure also contemplates directing the electrical energy produced by the electrode assemblies into the liquid medium in a direction which causes the liquid medium to propagate pressure waves toward the guidewire lumen and/or guidewire such that the pressure waves excite and vibrate the guidewire.

Figure 20:
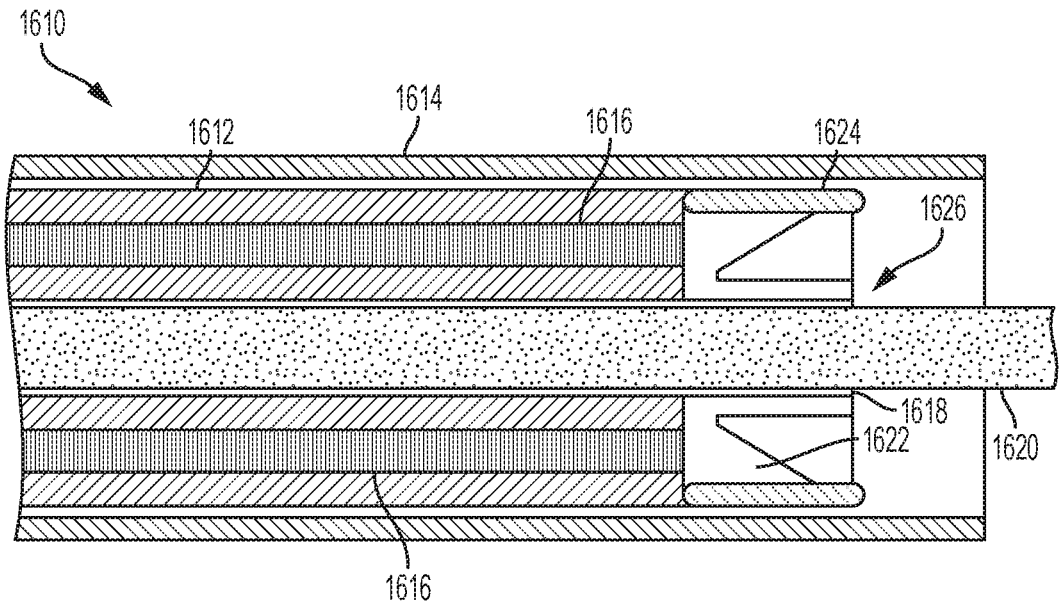
FIG. 20 is a representative cross-sectional view of the distal end of a catheter, according to one embodiment of the present disclosure.
Figure 20:
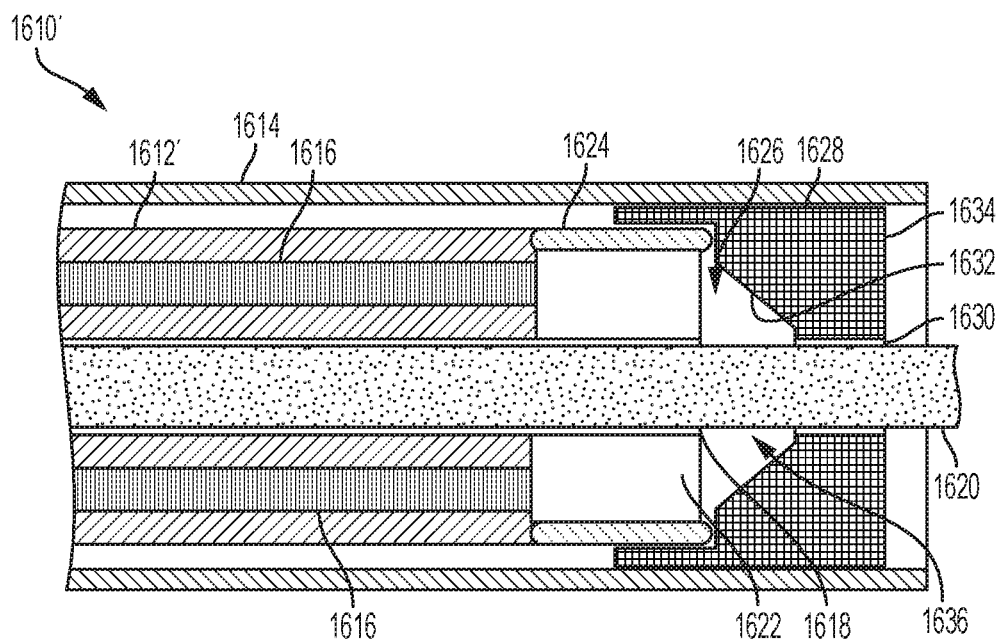
Figure 20:
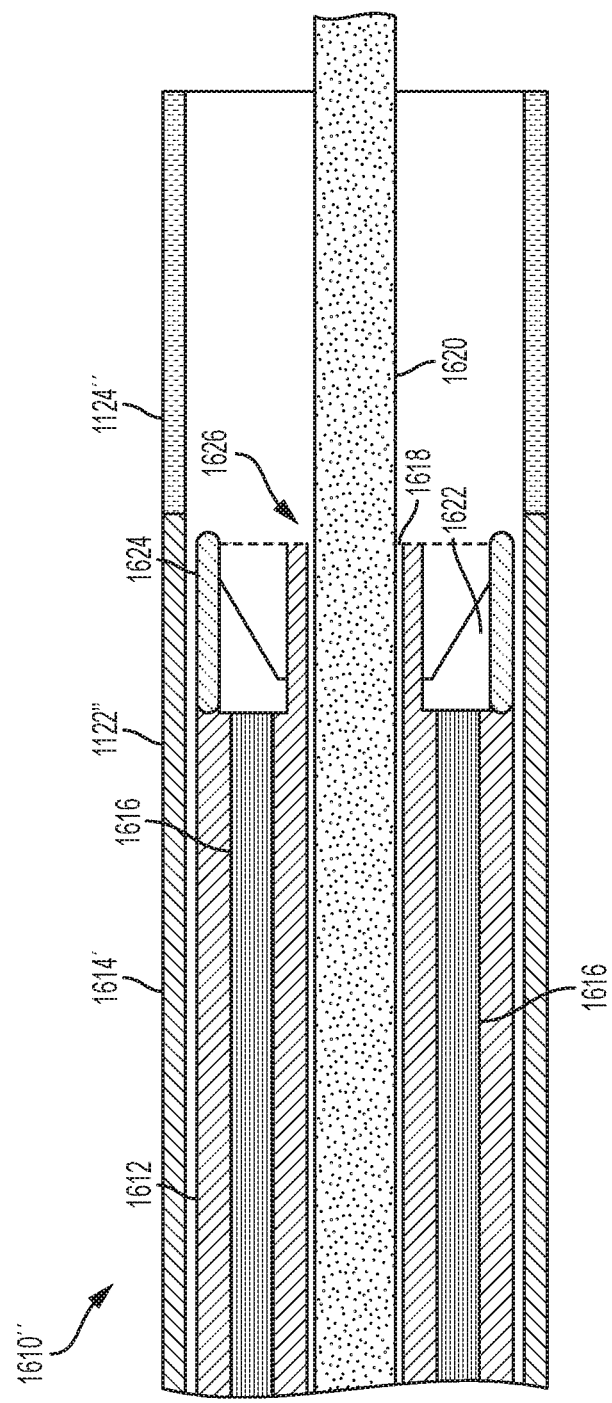

Referring to FIG. 20, there is depicted a cross-sectional view of the distal end of system 1610 including an electrode catheter 1612 radially disposed within a sheath 1614. As shown, the distal end of the catheter 1612 includes one or more electrical cables 1616 arranged circumferentially around an inner guidewire lumen 1618 that receives a guidewire 1620. The inner layer of electrical cables 1616 extends to the distal tip 1626 of the catheter 1612 and terminates at the electrode assembly 1622 within the catheter 1612. The liquid medium may be introduced distal to the catheter 1612 through a lumen in the catheter 1612 (for example, the guidewire lumen 1618), a lumen in the sheath 1614 (not shown), and/or the lumen or space between the electrode catheter 1612 and the sheath 1614.

Continuing to refer to FIG. 20, in addition to having a plurality of electrical cables 1616, at least one electrode assembly 1622 and a guidewire lumen 1618, the catheter 1612 may also include an outer band 1624 that surrounds the distal tip 1626, thereby increasing the strength and rigidity of the distal tip 1626. As mentioned above, the present disclosure contemplates directing the electrical energy, such as the arc created across the electrodes, produced by the electrode assembly 1622 into the liquid medium in a direction which causes the liquid medium to propagate pressure waves toward the guidewire lumen 1618 and/or the guidewire 1620 such that the pressure waves excite and vibrate the guidewire 1620. A means for directing electrical energy produced by the electrode assembly 1622 towards the guidewire lumen 1618 or the guidewire 1620 includes disposing the electrode assembly 1622 proximate the distal tip 1626 of the catheter 1612 and/or proximate the distal end of the outer band 1624 such that the electrode assembly 1622 is recessed from the distal tip 1626 of the catheter 1612 and/or proximate the distal end of the outer band 1624 along the longitudinal axis of the catheter 1612. By recessing the electrode assembly 1622 from the distal tip 1626 of the catheter 1612 and/or proximate the distal end of the outer band 1624, the pressure waves may be directed toward the guidewire lumen 1618 and/or the guidewire 1620.

An additional means for directing electrical energy produced by the electrode assembly 1622 towards the guidewire lumen 1618 and/or the guidewire 1620 includes directing the electrode assembly 1622 toward the guidewire lumen 1618 or the guidewire 1620. The electrode assembly 1622 is directed towards the guidewire lumen 1618 and/or the guidewire 1620 because the electrodes are tapered in a manner that the arc created by the electrodes to be directed radially inward towards the guidewire lumen 1618 and/or the guidewire 1620. As illustrated in FIG. 20, the guidewire lumen 1618 and/or guidewire 1620 may extend longitudinally distal of the electrode assembly 1622. Accordingly, as the electrical energy is produced by the electrode assembly 1622, the electrical arc interacts with the liquid medium, and the liquid medium absorbs the plasma energy, thereby creating pressure waves and/or cavitation bubbles and additional resultant pressure waves that cause the guidewire lumen 1618 and/or guidewire 1620 to excite and/or vibrate.

Referring to FIG. 20', there is depicted an alternate embodiment of the present disclosure, particularly an alternate embodiment of a means for directing electrical energy produced from the electrode assembly 1622 towards the guidewire lumen 1618 and/or the guidewire 1620. Similar to the embodiment discussed above with respect to FIG. 20, the system 1610' in FIG. 20' includes a catheter 1612' having a one or more cables coupled to an electrode assembly 1622, a guidewire lumen 1618, and an optional outer band 1624 that surrounds the distal tip 1626. This embodiment also includes a cap 1628 having a guidewire lumen 1630 extending therethrough.

The cap 1628 can be either removably coupled to the catheter 1612', particularly removably coupled to the outer band 1624, or the cap 1628 can be permanently affixed to the catheter 1612', particularly permanently affixed to the outer band 1624. The cap 1628 includes a proximal (for example, interior) side 1632 and a distal (for example, exterior) side 1634. The interior side 1632 is tapered such that a cavity 1636 forms between the distal end of the catheter 1612' and the interior side 1632 of the cap 1628, thereby allowing the liquid medium to enter and collect within the cavity 1636.

Although FIG. 20' is depicted as having a catheter 1612' with a flush distal end and a tapered, recessed cap 1628 to create the cavity 1636 between the catheter 1612' and the cap 1628 for the liquid medium to collect, the present disclosure also contemplates having a catheter with a recessed distal end, as depicted in FIG. 20, that could be used in conjunction with a cap 1628 having a flush or recessed interior side 1632 to create a cavity for the liquid medium to collect. Accordingly, as the electrical energy is produced by the electrode assembly 1622, the electrical interacts with the liquid medium within the cavity, and the liquid medium absorbs the electrical energy, thereby creating pressure waves and/or cavitation bubbles and additional resultant pressure waves that cause the guidewire lumen 1618 and/or guidewire 1620 to excite and/or vibrate.

The sheath 1614 may be, for example, any of the sheaths described herein. In some embodiments, the sheath 1614 may be the sheath 1140 shown in FIGS. 11A-11D, and the catheter 1612 or 1612' may be translatably carried therein. Referring now to FIG. 20", system 1610" may include electrode catheter 1612. The system 1610" may also include a sheath 1614' that translatably carries the catheter 1612. The sheath 1614' may be the sheath 1120" shown in FIGS. 18-18E. That is, the sheath 1614' includes a sleeve or jacket 1122" and a porous attenuating member 1124", which may be any of the attenuating members described herein.

The porous attenuating member 1124" has multiple purposes, as follows: (1) reinforcing the sleeve 1122" and/or the sheath 1614; (2) reducing or preventing the formation of cavitation bubbles exterior of the attenuating member 1124", the sleeve 1122" and/or the sheath 1614; (3) redirecting at least a portion of the pressure waves toward the guidewire lumen 1618 and/or guidewire 1620 to excite and/or vibrate the guidewire 1620. Accordingly, the attenuating member 1124" acts as (1) a means for reinforcing the sleeve 1122" and/or the sheath 1614'; (2) a means for reducing or preventing the formation of cavitation bubbles exterior of the attenuating member 1124", the sleeve 1122" and/or the sheath 1614'; (3) a means for redirecting at least a portion of the pressure waves toward the guidewire lumen 1618 and/or guidewire 1620 to excite and/or vibrate the guidewire 1620.

Further details regarding the first and second purposes of the attenuating member 1124" are described in connection with FIG. 18. Regarding the ability of the attenuating member 1124" to redirect at least a portion of the pressure waves toward the guidewire lumen 1618 and/or guidewire 1620 to excite and/or vibrate the guidewire 1620, the pressure waves or portion of the pressure wave(s) that do not pass through the attenuating member 1124" may be redirected by the attenuating member 1124" toward the guidewire lumen 1618 and/or guidewire 1620 to excite and/or vibrate the guidewire 1620. The sizes of the openings 1126" of the attenuating member 1124" (see FIG. 18) may be selected to control the amount of pressure waves that are reflected toward the guidewire lumen 1618 and/or guidewire 1620.

Also, similar to the discussion included above with respect to FIG. 18 the porous attenuating member 1124" depicted in FIGS. 20" and 20''' is shown at the distal end of the sheath 1614'. The porous attenuating member 1124", however, may alternatively and/or additionally as be disposed at the proximal end of the sheath 1614', the central portion of the sheath 1614', any location or multiple locations between the proximal end and distal end of the sheath 1614', or in the entire length or substantially the entire length of the sheath 1614'. Therefore, as the catheter 1612 or 1612' translates within the sheath 1614', the guidewire 1620 will continue to excite and/or vibrate.

Figure 21:
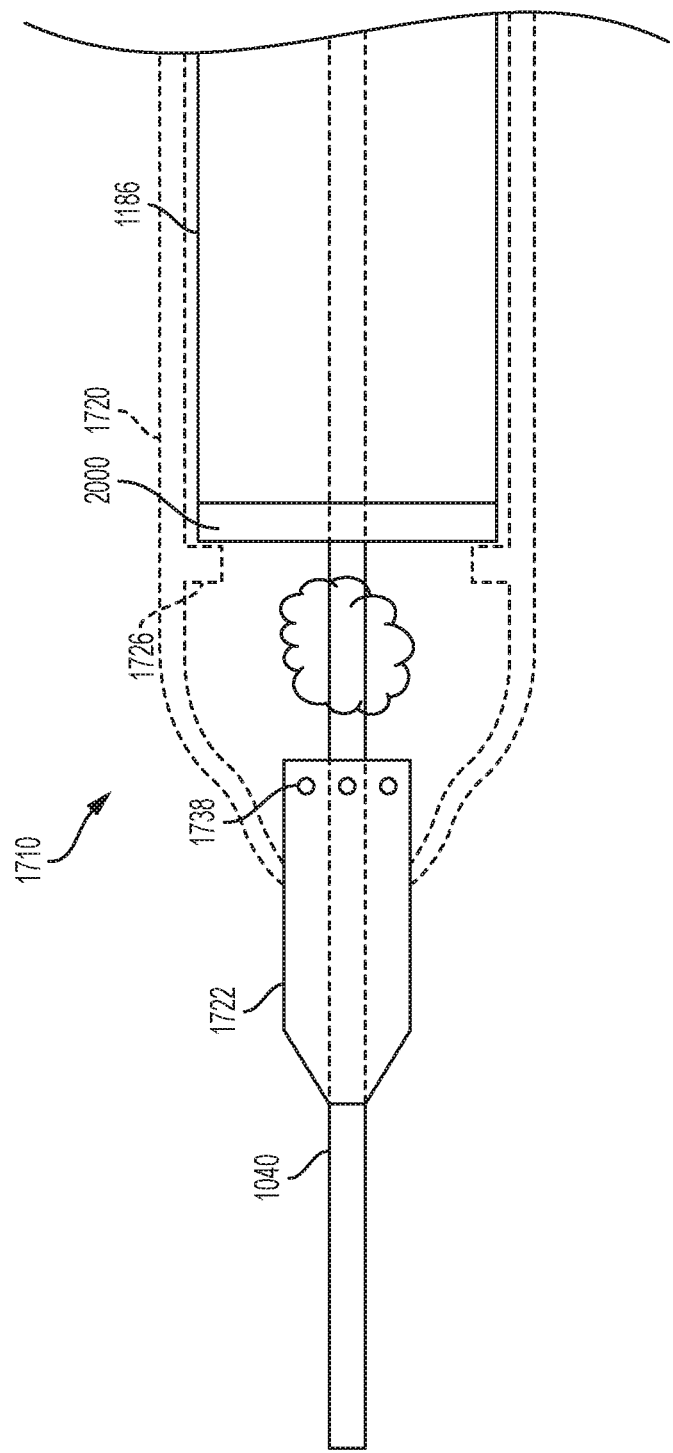
FIG. 21 is a representative side view of a catheter system including an electrode catheter and a sheath having a sealable valve, according to an embodiment of the present disclosure.
Figure 22:
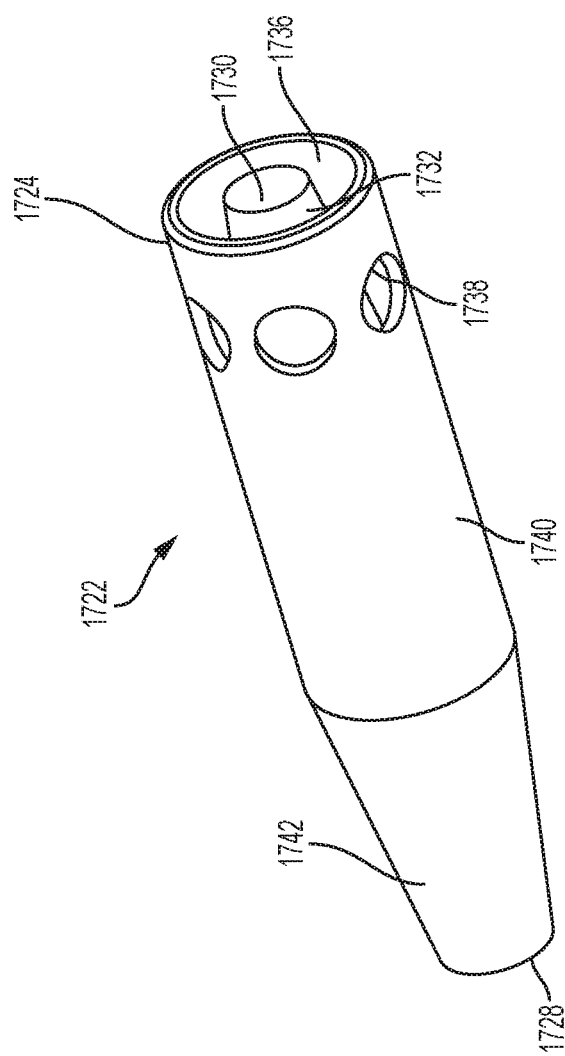
FIG. 22 is an enlarged representative perspective view of the sealable valve of the catheter system depicted in FIG. 21.

As described above, for example, with reference to FIG. 13, catheter systems according to embodiments of the present disclosure may have distal tips that are fully or partially closed. In some of these embodiments, it may be desirable to seal the sheath with the guidewire upon introduction of the liquid medium to the closed distal tip. FIGS. 21-22B illustrate a catheter system 1710 according to such an embodiment. That is, the catheter system 1710 includes a sheath 1720 (which is hidden in FIG. 21 to illustrate internal components of the catheter system 1710) that has a partially-closed tip 1722. The sheath 1720 carries an electrode catheter, such as the electrode catheter 1010 described herein, and the electrode catheter 1010 may translate distally and/or proximally within the sheath 1720. As shown in FIG. 21, the sheath 1720 may taper proceeding distally toward the tip 1722. Alternatively, the sheath 1720 may include a flat surface that receives the tip 1722. As another alternative, the tip 1722 may have a similar size to the lumen of the sheath 1720 and be press-fittingly received in the lumen. In order to ensure that a cavity remains between the distal end of the electrode catheter 1010 and the proximal end 1724 of the tip 1722 of the sheath 1720, the sheath 1720 may include one or more internal stops 1726. The shape of the tip 1722 may be configured similar to the tips 180 illustrated and described with respect to FIGS. 2-6 such that the catheter system 1710, including the electrode catheter tip 1722, is configured such that the energy produced by the pressure waves is captured within the cavity and the forces generated by the pressure waves propagate longitudinally, including in a forward (such as, parallel with the vessel) direction, thereby increasing the tip's ability to disrupt, destroy and/or penetrate the vascular obstructions.

The tip 1722 includes the proximal end 1724, a distal end 1728, and a lumen 1730 extending therethrough from its proximal end 1724 to its distal end 1728. The tip 1722 also includes a valve that seals the intersection of the tip 1722 and the guidewire 1040 as the guidewire 1040 passes through the guidewire lumen 1730. One example of a valve is that which is depicted in FIGS. 22-22B which illustrate a flange 1732 that is disposed at and/or toward the proximal end 1724 of the tip 1722.

Figure 22A:
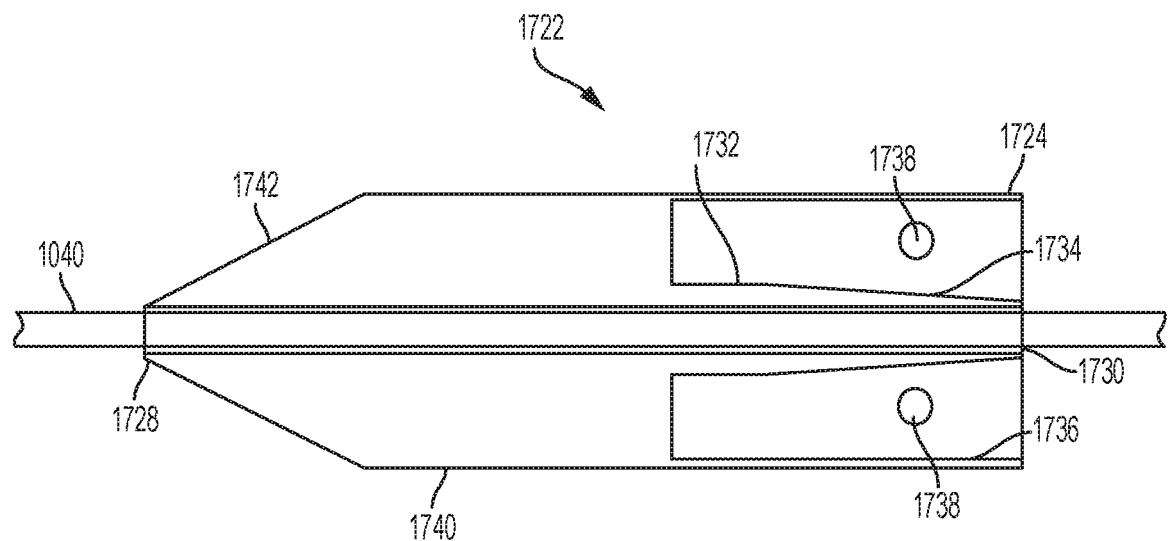
FIG. 22A is an enlarged representative cross-sectional side view of the sealable valve of the catheter system depicted in FIG. 21 in an unsealed configuration with respect to a guidewire.
Figure 22B:
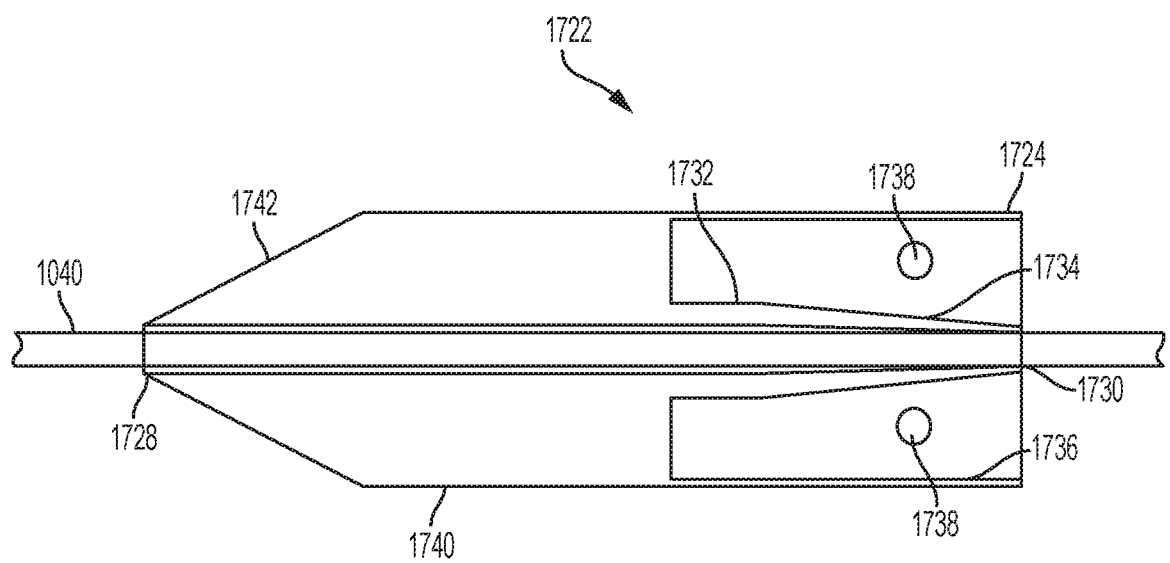
FIG. 22B is an enlarged representative cross-sectional side view of the sealable valve of the catheter system depicted in FIG. 21 in a sealed configuration with respect to a guidewire.

Referring back to FIGS. 21-22B, upon introducing the guidewire 1040 through the lumen 1730 of the electrode catheter 1010 and into the guidewire lumen 1730 of the tip 1722, the guidewire 1040 and tip 1722 are slidably coupled such that the tip 1722 can slide over the guidewire 1040 (or the guidewire 1040 can slide through a lumen 1730 of the tip 1722), as depicted in FIG. 22A. As illustrated in this figure, there is a gap (or opening) caused by the guidewire lumen 1730 between the flange 1732 and the guidewire 1040. If the gap is maintained during introduction of the liquid medium into the distal end of the catheter system 1710 (via, for example, the opening or gap between the electrode catheter 1010 and the sheath 1720), the liquid medium would travel through the guidewire lumen 1730 and into the patient's vasculature, which may be undesirable. The flange 1732, which may include a tapered portion 1734 that tapers from the tip's distal end 1728 toward its proximal end 1724, is configured to radially collapse upon introduction of the liquid medium into the distal end of the catheter system 1710 due to the increased fluid pressure on the flange 1732. The increased fluid pressure on the flange 1732 actuates the flange 1732 and moves it radially inward toward the guidewire lumen 1730 such that the gap between flange 1732 and the guidewire 1040 closes, thereby creating a seal between the between flange 1732 and the guidewire 1040, as depicted in FIG. 22B. The reduced thickness of the tapered portion 1734 of the flange 1732 as the flange 1732 tapers radially inward towards the guidewire lumen 1730 as the flange 1732 progresses from the distal end 1728 toward the proximal end 1724 increases the flange's ability to flex upon exposure to the pressure created upon introduction of the liquid medium. Upon removal of the liquid medium from the distal end of the catheter system 1710, the pressure within the catheter system 1710, the pressure on the flange 1732 decreases, and the flange 1732 naturally retracts to its original position as depicted in FIG. 22A, thereby reestablishing the gap between the tip 1722 and the guidewire 1040 so that the two components may slide with respect to one another. Accordingly, the flange 1732 acts as sealable valve within the tip 1722, and the flange 1732 is actuated with the introduction and removal of the liquid medium into and from the distal end of the catheter system 1710.

Although the tapered portion 1734 illustrated in FIGS. 22A and 22B tapers from the tip's distal end 1728 toward its proximal end 1724, the direction of the taper may be reversed such that the tapered portion 1734 tapers from the tip's proximal end 1724 toward its distal end 1728. Additionally, the flange 1732 may taper towards any portion along its length such that a portion of the flange 1732 is thinner at one or more locations along its length in comparison to other locations along its length. Accordingly, upon an increased fluid pressure being imparted on the flange 1732, thinner portion of the flange 1732 actuates and moves radially inward toward the guidewire lumen 1730 such that the gap between flange 1732 and the guidewire 1040 closes, thereby creating a seal between the between flange 1732 and the guidewire 1040.

The tip 1722 may be constructed from any type of compressible or compliant biopolymers, such as silicones or flouro-polymers, compliant adhesives, etc. The configuration of the tip 1722 depicted in these figures includes an exterior wall 1736 and the flange 1732 disposed radially therein, to create a gap therebetween for the liquid medium to enter and actuate the flange 1732. The flange 1732 is also depicted as being disposed toward the proximal end 1724 of the tip 1722, which itself is depicted as tubular, and its distal end 1728 has an inward taper that tapers distally from the exterior wall 1736 towards the guidewire lumen 1730. Although the tip 1722 is depicted as including particular components and shapes, the present disclosure shall include other shapes and components known to one of skill in the art. Moreover, the tip 1722 may alternatively include a self-sealing tube constructed of any type of compressible or compliant biopolymers, such as silicones or flouro-polymers, compliant adhesives, etc. For example, the tip 1722 may include a tube that has a lumen 1730 passing therethrough such that upon insertion of a guidewire, the lumen expands, and upon removable of the guidewire, the lumen contracts, thereby appearing as a slit.

Continuing to refer to FIGS. 21-22B, the tip 1722 may include one or more openings 1738 through its exterior wall 1736. The openings 1738 allow the inflation liquid to reach the flange 1732 not only from the gap between the flange 1732 and the exterior wall 1736 at the proximal end 1724 of the tip 1722 but also at a location distal the proximal end 1724 of the tip 1722. Allowing the inflation liquid to reach the flange 1732 at or toward its distal portion, potentially increases the likelihood and effectiveness of actuating the flange 1732. Although the tip 1722 is illustrated as having a tubular section 1740 from its proximal end 1724 and a tapered section 1742 from the end of its tubular section 1740 toward the tip's distal end 1728, the scope of this disclosure shall include other shapes for the tip 1722.

As discussed herein, as the electrical energy is produced by the electrode assembly 2000, particularly an arc is created across the electrodes, the electrical energy interacts with the liquid medium, and the liquid medium absorbs the electrical energy, thereby creating cavitation bubbles within the catheter system 1710. The openings 1738 within the tip 1722 may reduce the size of the bubble formed within the catheter system 1710 and/or reduce the likelihood that the bubble will expand toward the distal end of the catheter system 1710.

Although a large portion of this disclosure includes a discussion of an electrically-induced pressure wave emitting catheter sheath system used in conjunction with a sheath assembly to perform CAD and PAD procedures, the same or other electrically-induced pressure wave emitting catheter sheath systems may be used to perform other types of medical and/or surgical procedures. Electrode catheters typically transmit electrical energy via electrical cables housed in a relatively flexible tubular catheter inserted into a body lumen, such as a blood vessel, ureter, fallopian tube, cerebral artery and the like to remove obstructions in the lumen. Electrically-induced pressure wave emitting catheter sheath systems used for other procedures may have a central passageway or tube which receives a guide wire inserted into the body lumen (for example, vascular system) prior to catheter introduction. The guide wire facilitates the advancement and placement of the catheter to the selected portion(s) of the body lumen for disruption of tissue.

The present disclosure, in various aspects, embodiments, and configurations, includes components, methods, processes, systems and/or apparatus substantially as depicted and described herein, including various aspects, embodiments, configurations, sub combinations, and subsets thereof. Those of skill in the art will understand how to make and use the various aspects, aspects, embodiments, and configurations, after understanding the present disclosure. The present disclosure, in various aspects, embodiments, and configurations, includes providing devices and processes in the absence of items not depicted and/or described herein or in various aspects, embodiments, and configurations hereof, including in the absence of such items as may have been used in previous devices or processes, for example, for improving performance, achieving ease and\or reducing cost of implementation.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more, aspects, embodiments, and configurations for the purpose of streamlining the disclosure. The features of the aspects, embodiments, and configurations of the disclosure may be combined in alternate aspects, embodiments, and configurations other than those discussed above. This method of disclosure is not to be interpreted as reflecting an intention that the claimed disclosure requires more features than are expressly recited in each claim. Rather, as the following claims reflect, inventive aspects lie in less than all features of a single foregoing disclosed aspects, embodiments, and configurations. Thus, the following claims are hereby incorporated into this Detailed Description, with each claim standing on its own as a separate preferred embodiment of the disclosure.

Moreover, though the description of the disclosure has included description of one or more aspects, embodiments, or configurations and certain variations and modifications, other variations, combinations, and modifications are within the scope of the disclosure, for example, as may be within the skill and knowledge of those in the art, after understanding the present disclosure. It is intended to obtain rights which include alternative aspects, embodiments, and configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A catheter system comprising: a first sheath having a guidewire lumen, a proximal end, and a distal end; at least one electrode assembly disposed adjacent to the guidewire lumen of the first sheath, wherein the at least one electrode assembly produces electrical energy; and a second sheath configured to receive the first sheath, wherein the second sheath comprises a distal end, and wherein the first sheath is translatable within the second sheath; and a porous attenuating member having a substantially tubular shape and an open distal end, wherein the porous attenuating member is coupled to extend distal to the distal end of the first sheath within the second sheath, to thereby direct acoustic pressure waves resulting from the electrical energy produced by the at least one electrode assembly towards the guidewire lumen of the inner sheath and thereby vibrate a guidewire extending through the guidewire lumen.

2. The catheter system of claim 1, wherein the porous attenuating member has a generally uniform diameter along its length.

3. The catheter system of claim 2, wherein the porous attenuating member comprises an inner surface, an outer surface, and a plurality of openings extending from the inner surface to the outer surface.

4. The catheter system of claim 3, wherein the plurality of openings comprise at least one of the following shapes: circle; oval; triangle; square; rectangle; polygon; diamond; pentagon; hexagon; heptagon; octagon; nonagon; and decagon.

5. The catheter system of claim 1, wherein the porous attenuating member reinforces the second sheath.

6. A method for treating an obstruction within vasculature of a subject, the method comprising:
    positioning a catheter system within the vasculature of the subject, the catheter system comprising:
        a first sheath having a guidewire lumen, a proximal end, and a distal end;
        at least one electrode assembly coupled to the first sheath;
        a second sheath configured tot receive the first sheath so that the first sheath is translatable within the second sheath, wherein the second sheath comprises a distal end; and
        a porous attenuating member having a substantially tubular shape and an open distal end, wherein the porous attenuating member is coupled to extend distal to the distal end of the first sheath within the second sheath to thereby direct pressure waves produced by the at least one electrode assembly towards the guidewire lumen or a guidewire within the guidewire lumen;
    positioning the distal end of the second sheath adjacent the obstruction within the vasculature;
    delivering a liquid medium to the distal end of the second sheath;

activating the at least one electrode assembly to produces pulses of electrical energy in the liquid medium;

wherein producing the pulses of electrical energy from the at least one electrode in the liquid medium generates a plurality of propagating pressure waves that disrupt at least a portion of the obstruction; and wherein the porous attenuating member directs pressure waves produced by the at least one electrode assembly towards the guidewire lumen or a guidewire within the guidewire lumen and thereby induces vibrations within the guidewire.

7. The method of claim 6, wherein the porous attenuating member comprises an inner surface, an outer surface, and a plurality of openings extending from the inner surface to the outer surface, and wherein transmitting the pulses of electrical energy produced by the at least one electrode assembly in the liquid medium generates a plurality of propagating pressure waves that pass through the plurality of openings.

8. The method of claim 7, wherein the plurality of openings comprise at least one of the following shapes: circle; oval; triangle; square; rectangle; polygon; diamond; pentagon; hexagon; heptagon; octagon; nonagon; and decagon.

9. The method of claim 6, wherein the porous attenuating member reinforces the second sheath.

10. A catheter assembly comprising:
an inner sheath having a guidewire lumen, a proximal end, a distal end, and at least one electrode assembly disposed adjacent to the guidewire lumen, wherein the at least one electrode assembly produces electrical energy; and an outer sheath configured to receive the inner sheath so that the inner sheath is translatable within the outer sheath; and an attenuating member having a substantially tubular shape and an open distal end, wherein the attenuating member extends distal to the distal end of the inner sheath within the outer sheath to thereby direct acoustic pressure waves resulting from the electrical energy towards the guidewire lumen of the inner sheath and thereby vibrate a guidewire extending through the guidewire lumen.

11. The catheter assembly of claim 10 wherein the electrode assembly is tapered toward the guidewire lumen to thereby direct the electrical energy radially toward the guidewire extending through the guidewire lumen.

12. The catheter assembly of claim 10 wherein the attenuating member is coupled to the distal end of the inner sheath by an adhesive.

13. The catheter assembly of claim 10 wherein the attenuating member is integrally disposed within the outer sheath distal to the inner sheath to thereby reinforce the outer sheath.

14. The catheter assembly of claim 10 wherein the attenuating member is porous.

15. The catheter assembly of claim 10 wherein the attenuating member comprises a plurality of opening extending therethrough.

16. The catheter assembly of claim 10 wherein the attenuating member has a generally uniform diameter along its length.

* * * * *